United States Patent
Damborsky et al.

(10) Patent No.: US 9,969,741 B2
(45) Date of Patent: May 15, 2018

(54) PYRAZOLOTRIAZINES AS INHIBITORS OF NUCLEASES

(71) Applicant: MASARYKOVA UNIVERZITA, Brno (CZ)

(72) Inventors: Jiri Damborsky, Brno (CZ); Fedor Nikulenkov, St. Petersburg (RU); Alexandra Sisakova, Slanec (SK); Stepan Havel, Cernozice (CZ); Lumir Krejci, Brno (CZ); Benoit Carbain, Montigny-le-Bretonneux (FR); Jan Brezovsky, Brno (CZ); Lukas Daniel, Zlin (CZ); Kamil Paruch, Tisnov (CZ)

(73) Assignee: MASARYKOVA UNIVERZITA, Brno (CZ)

( * ) Notice: Subject to any disclaimer, the term of this patent is extended or adjusted under 35 U.S.C. 154(b) by 0 days. days.

(21) Appl. No.: 15/316,764

(22) PCT Filed: Jun. 17, 2015

(86) PCT No.: PCT/CZ2015/000063
§ 371 (c)(1),
(2) Date: Dec. 6, 2016

(87) PCT Pub. No.: WO2015/192817
PCT Pub. Date: Dec. 23, 2015

(65) Prior Publication Data
US 2017/0197966 A1    Jul. 13, 2017

(30) Foreign Application Priority Data
Jun. 20, 2014   (EP) ..................................... 14173242

(51) Int. Cl.
C07D 487/04    (2006.01)
A61K 31/53     (2006.01)
A61P 35/00     (2006.01)

(52) U.S. Cl.
CPC ............ *C07D 487/04* (2013.01); *A61K 31/53* (2013.01)

(58) Field of Classification Search
CPC ............................. C07D 487/04; A61K 31/53
USPC .......................................... 544/184; 514/243
See application file for complete search history.

(56) References Cited

U.S. PATENT DOCUMENTS
2009/0082354 A1* 3/2009 Berger ................. C07D 487/04
                                                        514/243

FOREIGN PATENT DOCUMENTS
WO    2009039387 A1    3/2009
WO    2014081820 A1    5/2014

OTHER PUBLICATIONS

Cecil Textbook of Medicine, edited by Bennet, J.C., and Plum F., 20th edition, vol. 1, 1004-1010, 1996.*
Freshney et al., Culture of Animal Cells, A Manual of Basic Technique, Alan R. Liss, Inc., 1983, New York, p. 4.*
Dermeret al., Bio/Technology, 1994, 12:320.*
Golub et al., Science, 286, 531-537, 1999.*
Slouka, et al., J. et al., "Reactions of 2-(benzimidazol-2-yl)acetonitrile and its N-ethoxycarbonyl derivative with some azol-3-diazonium salts",Collection of Czechoslovak Chemical Communications, vol. 49, No. 1, 1984, pp. 275-279.
Ledenyova, Irina, et al., Azo-coupling of pyrazole-3(5)-diazonium chlorides with cyanothioacetamide: a convenient synthesis of pyrazolo[5,1-c] [1,2,4]triazine-3-carbothio amides, Tetrahedron Letters, Pergamon, GB, vol. 55, No. 6, Jan. 8, 2014 (Jan. 8, 2014), pp. 1239-1242.
Didenko, V. V., et al., First example of an ANRORC rearrangement of apyrazolo[5,1-c][1,2,4]triazine involving a side chain,Chemistry of Heterocyclic Compounds, vol. 46, No. 6, 2010, pp. 770-772.
Elmoghayar, et al., "Activated Nitriles in Heterocyclic Synthesis, IV. Synthesis of 1,3,4-Thiadiazole Derivatives", Liebigs Annalen Der Chemie, Verlag Chemie GMBH. Weinheim, DE, vol. 1985, No. 10, Oct. 1985 (Oct. 1985), pp. 1962-1968.
Cankar, Petr, et al., "The Synthesis of 4-Amino-3-(2-pyridyl)pyrazolo[S,1-c] [1,2,4 ]triazine and Some of its Derivatives",Journal of Heterocyclic Chemistry,Wiley-Blackwell Publishing, Inc, US, vol. 40, No. 1, Jan. 2003 (Jan. 2003),pp. 71-75.
Padwa, Albert, et al., Higher Order Dipolar Cycloaddition Reactions of Diazoazoles with Electron-Rich Dipolarophiles, The Journal of Organic Chemistry, American Chemical Society, US, vol. 48, No. 14, Jul. 1983 (Jul. 1983), pp. 2330-2336.

* cited by examiner

*Primary Examiner* — Venkataraman Balasubramanian
(74) *Attorney, Agent, or Firm* — Notaro, Michalos & Zaccaria P.C.

(57) ABSTRACT

The invention provides compounds represented by the structural formula (1):

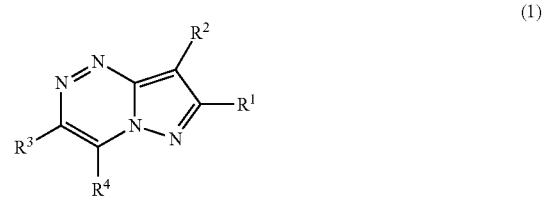

(1)

wherein $R^1$, $R^2$, $R^3$ and $R^4$ are as defined in the claims. The compounds are inhibitors of nucleases, and are useful in particular in a method of treatment and/or prevention of proliferative diseases, neurodegenerative diseases, and other genomic instability associated diseases.

5 Claims, No Drawings

PYRAZOLOTRIAZINES AS INHIBITORS OF NUCLEASES

FIELD OF THE INVENTION

The present invention relates to substituted pyrazolo[5,1-c][1,2,4]triazines as inhibitors of nucleases, regulators or modulators, pharmaceutical compositions containing the compounds, and methods of treatment using the compounds and compositions to treat diseases such as cancer and other genome instability associated diseases.

BACKGROUND ART

Despite intense development of new anticancer substances, the clinical treatment of most frequently diagnosed solid tumors needs to be improved and for some malignancies reasonably efficient therapies need to be developed, as they are practically non-existent. Early detection followed by surgery remains the main tool that enables significant expansion of life span for majority of patients. In most malignancies it may be necessary to modulate (preferably in a synergistic manner) several relevant biological pathways. Accordingly, the required phenotype (death of tumor cells) can be elicited by synthetic lethal modulation of properly chosen biological processes. Synthetic lethal interactions tend to form clusters; one significant network of such interactions encompasses the biological processes involved in the DNA damage/repair. Selective and efficient activity modulation of selected processes is therefore of significant importance and can lead to a new generation of modern anticancer drugs.

Maintenance of genomic integrity ensured by multifaceted cellular DNA damage response (DDR) is a fundamental biological phenomenon shared by all organisms. On one hand, the DDR network of genome surveillance, checkpoint and repair pathways counterbalances the potentially mutagenic effects of endogenous (oxidative and replicative lesions) and exogenous (e.g. ionizing or UV radiation, cigarette smoke) DNA damaging assaults. On the other hand, modulation of selected components can be exploited in efficient treatment of malignant diseases. It is likely that optimal synthetic lethal treatments will be different for particular tumor sub-populations; this approach is therefore compatible with the concept of personalized medicine.

Mammalian MUS81 protein with its partners EME1 or EME2 form a heterodimeric structure-specific endonuclease that preferentially cleaves 3' flaps and replication fork intermediates (*Genes Dev.* 2001, 15, 2730.). This endonuclease has been shown to facilitate restart of stalled DNA replication forks by generating DNA double-strand breaks (*EMBO J.* 2006, 25, 4921.). MUS81 also interacts with other DNA damage repair proteins including Rad54, BLM, as well as SLX4 (*Cell* 2009, 138, 78.; *Mol. Cell* 2009, 35, 116.; *Cell* 2009, 138, 63.). In addition, inactivation of MUS81 has been shown to result in chromosomal abnormalities and increased sensitivity to crosslinking agents (*Nucleic Acids Res.* 2006, 34, 880.; *Science* 2004, 304, 1822), indicating essential role of Mus81 in genome maintenance. Accordingly, decreased levels of MUS81 expression have been found in hepatic metastasis and correlated with poor cancer prognosis (*Cancer* 2008, 112, 2002). Furthermore, it has been recently shown that dual inactivation of CBX2 and MUS81 remarkably affect cancer cells (*PLoS Genet.* 2011, 7, e1001385.). These findings suggest that MUS81 is a good target for pharmacological intervention.

Amongst all DNA repair processing enzymes, the MRE11-RAD50-NBS1 (MRN) complex plays an important role in preserving genomic integrity by acting as a DNA damage sensor of double strand breaks (DSB) and by promoting repair through non-homologous end-joining (NHEJ) or homologous recombination (*Nature Reviews* 2002, 3, 317.; *Trends Biochem. Sciences* 2002, 27, 410.). In response to DSB, MRN activates and recruits ATM (belonging to the phosphatidylinositol-3' kinase-related kinases (PIKKs) family) to damaged DNA sites. ATM initiates a signaling cascade leading to cell cycle arrest and DNA repair. MRE11 is the subunit core of the MRN complex and displays 3'-5'exonuclease activity, single-stranded and DNA-hairpin endonuclease activity. The MRE11-RAD50 complex functions include DNA binding, bridging the ends of DSBs and their processing. NBS1 does not possess any enzymatic activity; its role lies in signaling and interacting with other proteins (*DNA Repair* 2010, 9, 1299.; *Cell* 2008, 135, 97.). The significance of MRN complex is underlined by the fact that germline mutations of MRE11, NBS1 and RAD50 cause ataxia-telangiectasia-like disease (ATLD), Nijmegen breakage syndrome (NBS) and NBS-like disorder (NBSLD), respectively (*Cell* 1998, 93, 477.; *Cell*, 1999, 99, 577.; *Am. J. Hum. Genet.* 2009, 84, 605). ATLD, NBS and NBSLD have similar features as does ataxia-telangiectasia (AT), caused by mutations in the ATM gene, which include hypersensitivity to DSB-inducing agents, chromosome fragility, DNA damage-dependent cell-cycle arrest and high predisposition to cancer (*Cell* 1998, 93, 477.; *Oncogene* 2007, 26, 7749; *Cell* 1999, 99, 577.; *Am. J. Hum. Genet.* 2009, 84, 605.). In addition, depletion of MRE11 leads to sensitization to poly(ADP-ribose) polymerase (PARP) inhibition (*Cancer Res.* 2011, 71, 2632.). Futhermore, MRE11-deficient cells are also sensitive to topoisomerase poisons, suggesting a role of MRE11 in removal of TOP1/TOP2-lessions and in stimulating an effect of topo inhibitors (*Mol. Cell. Biol.* 2004, 24, 9682.). Indeed, triapine (RNR inhibitor) was recently shown to block MRN-mediated recombination and sensitize ovarian cancer cells to PARP and topo inhibitors (*Mol. Cancer Res.* 2014, 12, 381.; *Cancer Res.* 2012, 72, 2814.). Therapeutic importance of MRE11 inhibitors in modern oncology is further supported by recently reported synthetically lethal genetic interactions for MRE11-FEN1 (*PLoS Genet.* 2013, 9, 1, e1003254.) and MRE11-BRCA2 (*Cancer Res.,* 2012, 72, 2814.).

DISCLOSURE OF THE INVENTION

The present invention provides substituted pyrazolo[5,1-c][1,2,4]triazine compounds, methods of preparing such compounds, pharmaceutical compositions comprising one or more of such compounds, methods of preparing pharmaceutical formulations comprising one or more of such compounds, and methods of treatment, prevention, inhibition or amelioration of one or more diseases associated with protein kinases using such compounds or pharmaceutical compositions.

The present invention provides compounds represented by the structural formula (1):

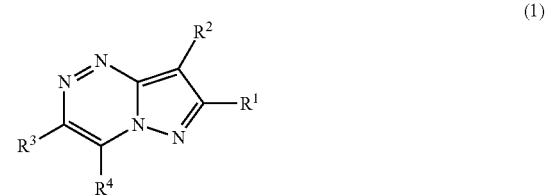

or a pharmaceutically acceptable salt, or solvate thereof, for use in a method of treatment of cancer, preferably MUS81-related and/or MRE11-related cancer, and/or Fen1-related cancer and/or Exo1-related cancer, wherein:

$R^1$ is selected from the group consisting of alkyl; aryl; cycloalkyl; heterocyclyl; and heteroaryl; wherein each of the alkyl, aryl, cycloalkyl, heterocyclyl, heteroaryl, can be unsubstituted or optionally substituted with one or more moieties which can be the same or different, each moiety being independently selected from the group consisting of F, Cl, Br, $C_1$-$C_6$-alkyl, O-phenyl, phenyl (alkyl, O-phenyl, phenyl being optionally substituted by F, Cl, Br, $C_1$-$C_6$-alkyl, OH, O—$C_1$-$C_6$-alkyl, SH, $SCH_3$, $S(O)C_1$-$C_6$-alkyl, $S(O)_2C_1$-$C_6$-alkyl, $CF_3$, $OCF_3$, $NH_2$, $NH(C_1$-$C_6$-alkyl), $N(C_1$-$C_6$-alkyl)$_2$ (such as $N(CH_3)_2$), $NO_2$, COOH, COO($C_1$-$C_6$-alkyl), $CONH_2$, CONH($C_1$-$C_6$-alkyl), CON($C_1$-$C_6$-alkyl)$_2$, NHC(O)$C_1$-$C_6$-alkyl, or NHC(O)$NH_2$), OH, O—$C_1$-$C_6$-alkyl, =O, SH, $SCH_3$, $S(O)C_1$-$C_6$-alkyl, $S(O)_2C_1$-$C_6$-alkyl, $CF_3$, $OCF_3$, $NH_2$, $NH(C_1$-$C_6$-alkyl), $N(C_1$-$C_6$-alkyl)$_2$ (such as $N(CH_3)_2$), $NO_2$, COOH, COO($C_1$-$C_6$-alkyl), $CONH_2$, CONH($C_1$-$C_6$-alkyl), CON($C_1$-$C_6$-alkyl)$_2$, NHC(O)$C_1$-$C_6$-alkyl, NHC(O)$NH_2$, $N_3$, $SO_2NH$ ($C_1$-$C_6$-alkyl), $SO_2N(C_1$-$C_6$-alkyl)$_2$;

$R^2$ is selected from the group consisting of H; alkyl; aryl; cycloalkyl; heterocyclyl; and heteroaryl; wherein each of the alkyl, aryl, cycloalkyl, heterocyclyl, heteroaryl, can be unsubstituted or optionally substituted with one or more moieties which can be the same or different, each moiety being independently selected from the group consisting of F, Cl, Br, $C_1$-$C_6$-alkyl, O-phenyl, phenyl (alkyl, O-phenyl, phenyl being optionally substituted by F, Cl, Br, $C_1$-$C_6$-alkyl, OH, O—$C_1$-$C_6$-alkyl, SH, $SCH_3$, $S(O)C_1$-$C_6$-alkyl, $S(O)_2C_1$-$C_6$-alkyl, $CF_3$, $OCF_3$, $NH_2$, $NH(C_1$-$C_6$-alkyl), $N(C_1$-$C_6$-alkyl)$_2$ (such as $N(CH_3)_2$), $NO_2$, COOH, COO($C_1$-$C_6$-alkyl), $CONH_2$, CONH($C_1$-$C_6$-alkyl), CON($C_1$-$C_6$-alkyl)$_2$, NHC(O)$C_1$-$C_6$-alkyl, or NHC(O)$NH_2$), OH, O—$C_1$-$C_6$-alkyl, =O, SH, $SCH_3$, $S(O)C_1$-$C_6$-alkyl, $S(O)_2C_1$-$C_6$-alkyl, $CF_3$, $OCF_3$, $NH_2$, $NH(C_1$-$C_6$-alkyl), $N(C_1$-$C_6$-alkyl)$_2$ (such as $N(CH_3)_2$), $NO_2$, COOH, COO($C_1$-$C_6$-alkyl), $CONH_2$, CONH($C_1$-$C_6$-alkyl), CON($C_1$-$C_6$-alkyl)$_2$, NHC(O)$C_1$-$C_6$-alkyl, NHC(O)$NH_2$, $N_3$, $SO_2NH$ ($C_1$-$C_6$-alkyl), $SO_2N(C_2$-$C_6$-alkyl)$_2$;

$R^3$ is selected from the group consisting of aryl and heteroaryl, wherein each of the aryl or heteroaryl can be unsubstituted or optionally substituted with one or more moieties which can be the same or different, each moiety being independently selected from the group consisting of F, Cl, Br, $C_1$-$C_6$-alkyl, O-phenyl, phenyl (alkyl, O-phenyl, phenyl being optionally substituted by F, Cl, Br, $C_1$-$C_6$-alkyl, OH, O—$C_1$-$C_6$-alkyl, SH, $SCH_3$, $S(O)C_1$-$C_6$-alkyl, $S(O)_2C_1$-$C_6$-alkyl, $CF_3$, $OCF_3$, $NH_2$, $NH(C_1$-$C_6$-alkyl), $N(C_1$-$C_6$-alkyl)$_2$ (such as $N(CH_3)_2$), $NO_2$, COOH, COO($C_1$-$C_6$-alkyl), $CONH_2$, CONH($C_1$-$C_6$-alkyl), CON($C_1$-$C_6$-alkyl)$_2$, NHC(O)$C_1$-$C_6$-alkyl, or NHC(O)$NH_2$), OH, O—$C_1$-$C_6$-alkyl, =O, SH, $SCH_3$, $S(O)C_1$-$C_6$-alkyl, $S(O)_2C_1$-$C_6$-alkyl, $CF_3$, $OCF_3$, $NH_2$, $NH(C_1$-$C_6$-alkyl), $N(C_1$-$C_6$-alkyl)$_2$ (such as $N(CH_3)_2$), $NO_2$, COOH, COO($C_1$-$C_6$-alkyl), $CONH_2$, CONH($C_1$-$C_6$-alkyl), CON($C_1$-$C_6$-alkyl)$_2$, NHC(O)$C_1$-$C_6$-alkyl, NHC(O)$NH_2$, $N_3$, $SO_2NH$ ($C_1$-$C_6$-alkyl), $SO_2N(C_1$-$C_6$-alkyl)$_2$;

$R^4$ is selected from the group consisting of H; OH; $NH_2$; $C_1$-$C_6$ alkyl;

provided that at least two, preferably at least three, of $R^1$, $R^2$, $R^3$, $R^4$ are other than hydrogen at the same time.

The present invention further provides compounds represented by the structural formula (1a):

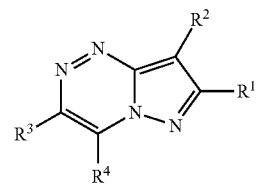

(1)

or a pharmaceutically acceptable salt, or solvate thereof, wherein:

$R^1$ is selected from the group consisting of alkyl; aryl; cycloalkyl; heterocyclyl; and heteroaryl; wherein each of the alkyl, aryl, cycloalkyl, heterocyclyl, heteroaryl, can be unsubstituted or optionally substituted with one or more moieties which can be the same or different, each moiety being independently selected from the group consisting of F, Cl, Br, $C_1$-$C_6$-alkyl, O-phenyl, phenyl (alkyl, O-phenyl, phenyl being optionally substituted by F, Cl, Br, $C_1$-$C_6$-alkyl, OH, O—$C_1$-$C_6$-alkyl, SH, $SCH_3$, $S(O)C_1$-$C_6$-alkyl, $S(O)_2C_1$-$C_6$-alkyl, $CF_3$, $OCF_3$, $NH_2$, $NH(C_1$-$C_6$-alkyl), $N(C_1$-$C_6$-alkyl)$_2$ (such as $N(CH_3)_2$), $NO_2$, COOH, COO($C_1$-$C_6$-alkyl), $CONH_2$, CONH($C_1$-$C_6$-alkyl), CON($C_1$-$C_6$-alkyl)$_2$, NHC(O)$C_1$-$C_6$-alkyl, or NHC(O)$NH_2$), OH, O—$C_1$-$C_6$-alkyl, =O, SH, $SCH_3$, $S(O)C_1$-$C_6$-alkyl, $S(O)_2C_1$-$C_6$-alkyl, $CF_3$, $OCF_3$, $NH_2$, $NH(C_1$-$C_6$-alkyl), $N(C_1$-$C_6$-alkyl)$_2$ (such as $N(CH_3)_2$), $NO_2$, COOH, COO($C_1$-$C_6$-alkyl), $CONH_2$, CONH($C_1$-$C_6$-alkyl), CON($C_1$-$C_6$-alkyl)$_2$, NHC(O)$C_1$-$C_6$-alkyl, NHC(O)$NH_2$, $N_3$, $SO_2NH$ ($C_1$-$C_6$-alkyl), $SO_2N(C_1$-$C_6$-alkyl)$_2$;

$R^2$ is selected from the group consisting of H; alkyl; aryl; cycloalkyl; heterocyclyl; and heteroaryl; wherein each of the alkyl, aryl, cycloalkyl, heterocyclyl, heteroaryl, can be unsubstituted or optionally substituted with one or more moieties which can be the same or different, each moiety being independently selected from the group consisting of F, Cl, Br, $C_1$-$C_6$-alkyl, O-phenyl, phenyl (alkyl, O-phenyl, phenyl being optionally substituted by F, Cl, Br, $C_1$-$C_6$-alkyl, OH, O—$C_1$-$C_6$-alkyl, SH, $SCH_3$, $S(O)C_1$-$C_6$-alkyl, $S(O)_2C_1$-$C_6$-alkyl, $CF_3$, $OCF_3$, $NH_2$, $NH(C_1$-$C_6$-alkyl), $N(C_1$-$C_6$-alkyl)$_2$ (such as $N(CH_3)_2$), $NO_2$, COOH, COO($C_1$-$C_6$-alkyl), $CONH_2$, CONH($C_1$-$C_6$-alkyl), CON($C_1$-$C_6$-alkyl)$_2$, NHC(O)$C_1$-$C_6$-alkyl, or NHC(O)$NH_2$), OH, O—$C_1$-$C_6$-alkyl, =O, SH, $SCH_3$, $S(O)C_1$-$C_6$-alkyl, $S(O)_2C_1$-$C_6$-alkyl, $CF_3$, $OCF_3$, $NH_2$, $NH(C_1$-$C_6$-alkyl), $N(C_1$-$C_6$-alkyl)$_2$ (such as $N(CH_3)_2$), $NO_2$, COOH, COO($C_1$-$C_6$-alkyl), $CONH_2$, CONH($C_1$-$C_6$-alkyl), CON($C_1$-$C_6$-alkyl)$_2$, NHC(O)$C_1$-$C_6$-alkyl, NHC(O)$NH_2$, $N_3$, $SO_2NH$ ($C_1$-$C_6$-alkyl), $SO_2N(C_1$-$C_6$-alkyl)$_2$;

$R^3$ is selected from the group consisting of benzimidazolyl and imidazolyl, wherein each of benzimidazolyl and imidazolyl can be unsubstituted or optionally substituted with one or more moieties which can be the same or different, each moiety being independently selected from the group consisting of F, Cl, Br, $C_1$-$C_6$-alkyl, O-phenyl, phenyl (alkyl, O-phenyl, phenyl being optionally substituted by F, Cl, Br, $C_1$-$C_6$-alkyl, OH, O—$C_1$-$C_6$-alkyl, SH, $SCH_3$, S(O) $C_1$-$C_6$-alkyl, $S(O)_2C_1$-$C_6$-alkyl, $CF_3$, $OCF_3$, $NH_2$, $NH(C_1$-$C_6$-alkyl), $N(C_1$-$C_6$-alkyl)$_2$ (such as $N(CH_3)_2$), $NO_2$, COOH, COO($C_1$-$C_6$-alkyl), $CONH_2$, CONH($C_1$-$C_6$-alkyl), CON ($C_1$-$C_6$-alkyl)$_2$, NHC(O)$C_1$-$C_6$-alkyl, or NHC(O)$NH_2$), OH, O—$C_1$-$C_6$-alkyl, =O, SH, $SCH_3$, $S(O)C_1$-$C_6$-alkyl, $S(O)_2C_1$-$C_6$-alkyl, $CF_3$, $OCF_3$, $NH_2$, $NH(C_1$-$C_6$-alkyl), $N(C_1$-$C_6$-alkyl)$_2$ (such as $N(CH_3)_2$), $NO_2$, COOH, COO($C_1$-$C_6$-alkyl), $CONH_2$, CONH($C_1$-$C_6$-alkyl), CON($C_1$-$C_6$- alkyl)$_2$, NHC(O)C$_1$-C$_6$-alkyl, NHC(O)NH$_2$, N$_3$, SO$_2$NH(C$_1$-C$_6$-alkyl), SO$_2$N(C$_1$-C$_6$-alkyl)$_2$;

R$^4$ is selected from the group consisting of H; OH; NH$_2$; C$_1$-C$_6$ alkyl;

provided that at least two, preferably at least three, of R$^1$, R$^2$, R$^3$, R$^4$ are other than hydrogen at the same time, and provided that if R$^1$ is phenyl, then it is substituted.

In this description and unless indicated otherwise, the generic substituent groups have the following meanings:

"alkyl" means an aliphatic hydrocarbon group which may be straight or branched and contains 1 to 8 carbon atoms, preferably 1 to 6 carbon atoms in the chain. Examples of suitable alkyls are methyl, ethyl, propyl, isopropyl, butyl, isobutyl, tert-butyl, pentyl, isopentyl, hexyl;

"aryl" means an aromatic monocyclic or polycyclic ring system containing 6 to 14 carbon atoms, preferably 6 to 10 carbon atoms. Examples of suitable aryls are phenyl, naphthyl, biphenyl, "cycloalkyl" means an aliphatic monocyclic or polycyclic ring system comprising 3 to 10 carbon atoms, preferably 5 to 7 carbon atoms. Suitable examples include cyclopentyl, cyclohexyl, cycloheptyl, 1-decalinyl, norbornyl, adamantyl;

"heterocyclyl" means an aliphatic monocyclic or polycyclic ring system containing 3 to 10 carbon atoms, preferably 4 to 8 carbon atoms, and at least one heteroatom selected from the group consisting of nitrogen, oxygen and sulfur. Suitable examples include piperazinyl and morpholinyl;

"heteroaryl" means an aromatic monocyclic or polycyclic ring system containing 3 to 14 carbon atoms, preferably 3 to 7 carbon atoms, and at least one heteroatom selected from the group consisting of nitrogen, oxygen and sulfur. Examples of suitable heteroaryls are pyridyl, pyrimidinyl, pyrazinyl, furanyl, thienyl, pyrazolyl, oxazolyl, thiazolyl, isothiazolyl, isoxazolyl, pyrrolyl, imidazolyl, benzimidazolyl, indolyl, indolinolyl or imidazopyridazinyl. Especially preferred are heteroaryls containing at least one nitrogen atom.

Preferably, R$^1$ is selected from alkyl, aryl, heteroaryl, optionally substituted by at least one moiety selected from F, Cl, Br, C$_1$-C$_6$-alkyl, O-phenyl, OH, O—C$_1$-C$_6$-alkyl, SH, SCH$_3$, CF$_3$, OCF$_3$, NH$_2$, or N(CH$_3$)$_2$. Even more preferably, R$^1$ is selected from ethyl, propyl, isopropyl, butyl, isobutyl, tert-butyl, phenyl, naphthyl, biphenyl, optionally substituted by at least one moiety selected from F, Cl, Br, C$_1$-C$_6$-alkyl, phenyl, OH, O—C$_1$-C$_6$-alkyl, SH, SCH$_3$, CF$_3$, OCF$_3$, NH$_2$, or N(CH$_3$)$_2$.

Preferably, R$^2$ is selected from H, alkyl, aryl, heteroaryl, optionally substituted by at least one moiety selected from F, Cl, Br, C$_1$-C$_6$-alkyl, OH, O—C$_1$-C$_6$-alkyl, COOH, COO(C$_1$-C$_6$-alkyl), S(O)$_2$(C$_1$-C$_6$-alkyl), NO$_2$, SH, SCH$_3$, CF$_3$, OCF$_3$, COO(C$_1$-C$_6$-alkyl), COOH, NH$_2$, or N(CH$_3$)$_2$. More preferably, R$^2$ is selected from H, methyl, ethyl, propyl, isopropyl, butyl, isobutyl, tert-butyl, phenyl, naphthyl, biphenyl, optionally substituted by at least one moiety selected from F, Cl, Br, C$_1$-C$_6$-alkyl, phenyl, OH, O—C$_1$-C$_6$-alkyl, SH, SCH$_3$, CF$_3$, OCF$_3$, NH$_2$, or N(CH$_3$)$_2$.

Preferably, R$^3$ is selected from aryl, heteroaryl, optionally substituted by at least one moiety selected from F, Cl, Br, C$_1$-C$_6$-alkyl, phenyl, OH, O—C$_1$-C$_6$-alkyl, SH, SCH$_3$, CF$_3$, OCF$_3$, NH$_2$, or N(CH$_3$)$_2$.

Preferably, R$^4$ is selected from OH, NH$_2$.

Preferably, R1 is not H.

Pharmaceutically acceptable salts are salts with acids or bases, or acid addition salts. The acids and bases can be inorganic or organic acids and bases commonly used in the art of formulation, such as hydrochloride, hydrobromide, sulfate, bisulfate, phosphate, hydrogen phosphate, acetate, benzoate, succinate, fumarate, maleate, lactate, citrate, tartrate, gluconate, methanesulfonate, benzenesulfonate, paratoluenesulfonate, primary, secondary and tertiary amides, ammonia. Solvates are structures containing molecules of a solvent, such as water (hydrates) or any other pharmaceutically acceptable solvent molecules.

In general, the compounds described in this invention can be prepared through the general routes described below in Schemes 1-7.

Reaction of nitrile 1 with ester 2 in the presence of a base provides intermediate 3, whose cyclization with hydrazine affords aminopyrazole 4; as shown in Scheme 1.

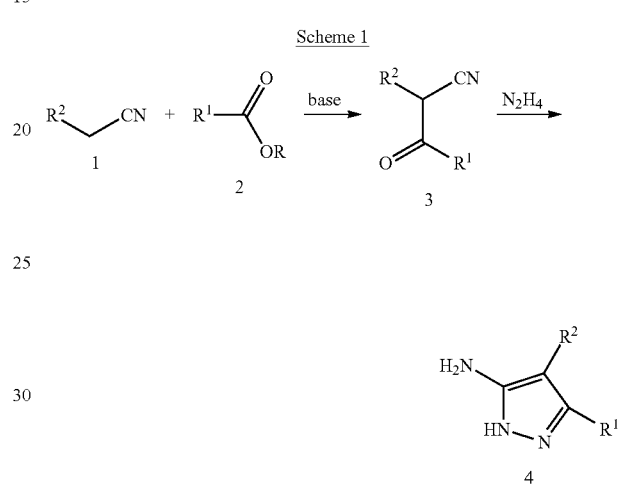

Alteratively, ketonitriles 3 (where R$^2$=aryl or heteroaryl) can be prepared by Pd-catalyzed arylation of unsubstituted 3 (where R$^2$=H); as shown in Scheme 2.

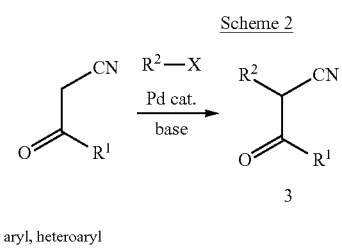

R$^2$ = aryl, heteroaryl
X = Cl, Br, I, OSO$_2$R

Diazotization of aminopyrazole 4 followed by reaction with nitride 5 yield the target pyrazolo[5,1-c][1,2,4]triazine; as depicted in Scheme 3.

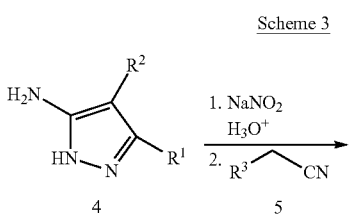

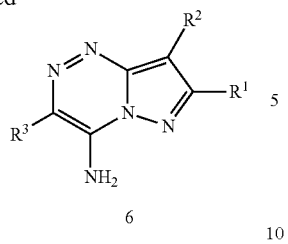

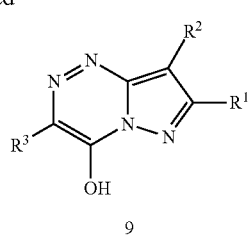

The position 2 in 6 (where $R^2$=H) can be selectively brominated, as shown in Scheme 4.

Compounds 9 (where $R^2$=H) can be selectively brominated and then further selectively functionalized, using palladium-catalyzed coupling reactions; as shown in Scheme 7.

Scheme 4

Scheme 7

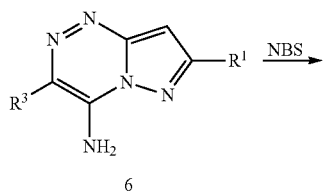

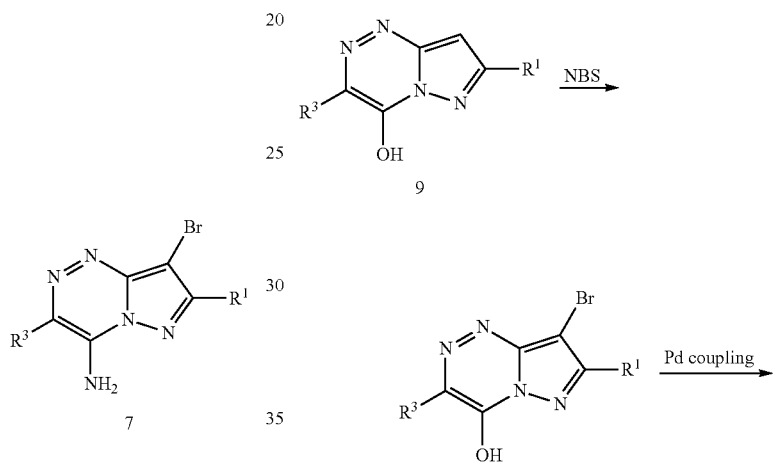

The amino group in 6 can be hydrolyzed or converted into chloride, as shown in Scheme 5.

Scheme 5

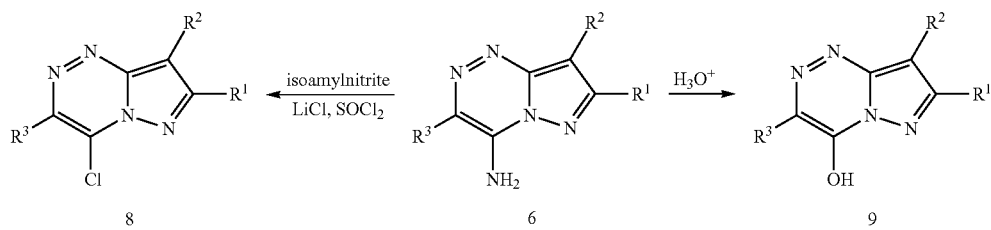

Alternatively, compounds 9 can be prepared by diazotization of aminopyrazole 4 followed by condensation with proper ester 10; as shown in Scheme 6.

-continued

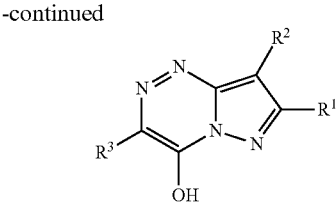

Scheme 6

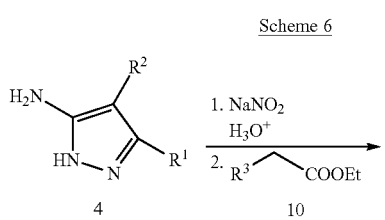

The compounds of Formula (1) act as nuclease inhibitors, in particular inhibitors of MUS81 and MRE11, and are useful in the treatment and prevention of proliferative diseases, e.g. cancer, in particular breast, colon, prostate, lung, head and neck, hepatic, ovarian, colorectal, gastric, melanoma cancers, leukemias, Nijmegen breakage syndrome and Nijmegen breakage-like syndrome, Ataxia-telangiectasia and Ataxia-telangiectasia-like disorder, and Fanconi anemia.

The present invention thus provides the compounds of formula (1) for use as medicaments. More specifically, it provides the compounds of formula (1) for use in the treatment and prevention of conditions selected from proliferative diseases, e.g. cancer, inflammation and arthritis, neurodegenerative diseases such as Alzheimer's disease, and other genomic instability associated diseases, in particular breast, colon, prostate, lung, head and neck, hepatic, ovarian, colorectal, gastric, melanoma cancers, leukemias, Nijmegen breakage syndrome and Nijmegen breakage-like syndrome, Ataxia-telangiectasia and Ataxia-telangiectasia-like disorder, and Fanconi anemia.

The present invention thus provides the compounds of formula (1) for use in combination with other chemo- and radiotherapy treatment and prevention of conditions selected from proliferative diseases, e.g. cancer, inflammation and arthritis, neurodegenerative diseases such as Alzheimer's disease, and other genomic instability associated diseases, in particular breast, colon, prostate, lung, head and neck, hepatic, ovarian, colorectal, gastric, melanoma cancers, leukemias, Nijmegen breakage syndrome and Nijmegen breakage-like syndrome, Ataxia-telangiectasia and Ataxia-telangiectasia-like disorder, and Fanconi anemia.

The present invention also provides a method for treatment, inhibition, amelioration or prevention of a condition selected from proliferative diseases, e.g. cancer, inflammation and arthritis, neurodegenerative diseases such as Alzheimer's disease, and other genomic instability associated diseases, in particular breast, colon, prostate, lung, head and neck, hepatic, ovarian, colorectal, gastric, melanoma cancers, leukemias, Nijmegen breakage syndrome and Nijmegen breakage-like syndrome, Ataxia-telangiectasia and Ataxia-telangiectasia-like disorder, and Fanconi anemia, in a patient suffering from such condition, comprising the step of administering at least one compound of formula (I) to said patient.

The present invention further includes pharmaceutical compositions comprising at least one compound of formula (I) and at least one pharmaceutically acceptable auxiliary compound. The auxiliary compounds may include, e.g., carriers, diluents, fillers, preservatives, stabilisers, binders, wetting agents, emulsifiers, buffers, etc. Suitable auxiliary compounds are well known to those skilled in the art of formulation. The pharmaceutical compositions are prepared by known methods, e.g., mixing, dissolving, etc.

EXAMPLES OF CARRYING OUT THE INVENTION

The present invention provides substituted pyrazolo[5,1-c][1,2,4]triazines which are represented by structural Formula (1), or pharmaceutically acceptable salts, solvates, esters or prodrugs thereof, wherein the various moieties are as described above.

Preparative Example A

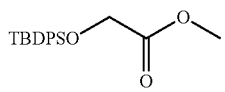

TBDPSCl (7.7 g, 28.27 mmol) was added under $N_2$ to a stirred solution of methyl 2-hydroxyacetate (2.3 g, 25.7 mmol), DMAP (1.7 g, 12.5 mmol) and $Et_3N$ (5.1 g, 51.4 mmol) in $CH_2Cl_2$ (30 mL). The reaction mixture was stirred at 25° C. for 16 hrs. The precipitate was removed by filtration and the filtrate was washed with 10% aqueous HCl (2×75 mL), then with water (2×50 mL), and dried over $MgSO_4$. The solvent was evaporated upon which the product was obtained as a colorless oil (8.2 g, 98%).

$^1$H NMR (500 MHz, CDCl$_3$): δ 1.11 (s, 9H), 3.70 (s, 3H), 4.26 (s, 2H), 7.43-7.38 (m, 41-1), 7.47-7.42 (m, 2H), 7.72-7.69 (m, 4H) ppm.

$^{13}$C NMR (125 MHz, CDCl$_3$): δ 19.5, 26.9, 51.5, 62.4, 128.0, 130.1, 135.8, 171.9 ppm.

HRMS calculated for $C_{10}H_7NO_2$ [M+H]$^+$ 174.0561, found 174.0565.

Preparative Example B

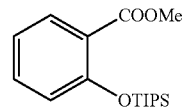

TIPSOTf (0.97 ml, 3.6 mmol) was added under $N_2$ to a stirred solution of methyl 2-hydroxybenzoate (0.5 g, 3.2 mmol), DMAP (0.2 g, 1.6 mmol) and $Et_3N$ (0.9 ml, 6.6 mmol) in anhydrous THF (10 mL). The mixture was stirred at 25° C. for 18 hrs, then poured into water (100 mL) and extracted with $Et_2O$ (3×50 mL). The organic extracts were dried over $MgSO_4$, filtered, and the solvent was evaporated. The residue was purified by chromatography on silica gel (hexane/EtOAc—10:1) to yield the product as a colorless oil (0.83 g, 82%).

$^1$H NMR (500 MHz, CDCl$_3$): δ 1.12 (d, 18H, J=7.4 Hz), 1.37-1.27 (m, 3H), 3.87 (s, 3H), 6.88 (dd, 1H, J=8.3, 0.8 Hz), 6.99-6.92 (m, 1H), 7.33 (tt, 1H, J=11.8, 3.2 Hz), 7.73 (dd, 1H, J=7.8, 1.8 Hz) ppm.

$^{13}$C NMR (125 MHz, CDCl$_3$): δ 13.3, 18.1, 52.0, 120.5, 120.6, 122.9, 131.7, 133.0, 155.7, 167.8 ppm.

HRMS calculated for $C_{17}H_{29}O_3Si$ [M+H]$^+$ 309.1880, found 309.1881.

Preparative Example C

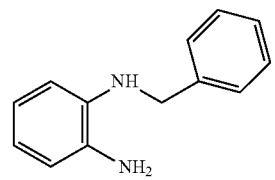 [SMILES: Nc1ccccc1NCc1ccccc1]

Benzyl bromide (2.7 g, 16.0 mmol) was added to a mixture o-diaminobenzene (8.0 g, 74.0 mmol) and $K_2CO_3$ (6.0 g, 44.0 mmol) in anhydrous MeOH (40 mL). The reaction mixture was stirred under $N_2$ at 25° C. for 20 hrs, then the solvent was evaporated and the residue was purified by column flash chromatography on silica gel (hexane/EtOAc—2:1) to afford the product as a dark-red liquid (2.58 g, 81%).

¹H NMR (500 MHz, CDCl₃): δ 3.44 (d, 3H), 4.34 (s, 2H), 6.73-6.69 (m, 2H), 6.78-6.73 (m, 2H), 6.83 (m, 1H), 7.35-7.28 (m, 2H), 7.38 (t, 2H, J=7.5 Hz), 7.43 (d, 1H, J=7.3 Hz) ppm.
¹³C NMR (500 MHz, CDCl₃): δ 48.9, 112.3, 116.8, 119.1, 121.0, 127.5, 128.0, 128.8, 134.4, 137.9, 139.6 ppm.

Preparative Example D

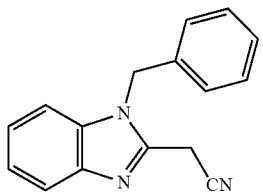 [SMILES: N#CCc1nc2ccccc2n1Cc1ccccc1]

Ethyl 2-cyanoacetate (2.20 g, 20.0 mmol) followed by methanesulfonic acid (0.1 mL) were afdded to a solution of compound from Preparative Example C (2.58 g, 13.0 mmol) in ethylene glycol (15 mL). The solution was refluxed for 4 hrs under N₂, poured into a mixture of water (100 mL) with saturated aqueous NaHCO₃ (25 mL), and extracted with EtOAc (3×50 mL). The organic extracts were washed with water (100 mL), brine (25 mL), then dried over MgSO₄, filtered, and the solvent was evaporated. The residue was purified by column chromatography on silica gel (eluent: hexane/EtOAc—10:1) to yield the product as a white crystalline solid (2.43 g, 75%).
MP=135.0-136.0° C.
¹H NMR (500 MHz, CDCl₃): δ 3.93 (s, 2H), 5.46 (s, 2H), 7.12-7.05 (m, 2H), 7.39-7.30 (m, 6H), 7.91-7.73 (m, 1H) ppm.
¹³C NMR (125 MHz, CDCl₃): δ 18.5, 47.7, 110.0, 114.3, 120.4, 123.2, 124.1, 126.6, 128.8, 129.6, 134.9, 136.1, 142.3, 143.5 ppm.
HRMS calculated for C₁₆H₁₂N₃ [M−H]⁻ 246.1037, found 246.1037.

Preparative Example E

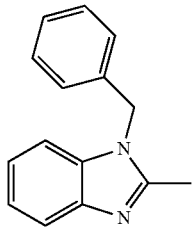 [SMILES: Cc1nc2ccccc2n1Cc1ccccc1]

Compound from Preparative Example C (387 mg, 1.95 mmol) was dissolved in CH₃COOH (2 mL) and EtOH (2 mL), and diethyl malonate (0.35 mL, 2.34 mmol) was added. The mixture was refluxed for 18 hrs and then poured into a mixture of saturated aqueous solution of NaHCO₃ (25 mL) and H₂O (25 mL). The mixture was extracted with EtOAc (3×25 mL). The combined organic extracts were washed with brine (25 mL), dried over MgSO₄, and concentrated. The residue was purified by column chromatography on silica gel (hexane/EtOAc: 1/1 to 0/1) to afford the product as a red solid (256 mg, 60%).

¹H NMR (500 MHz, CDCl₃): δ 2.59 (s, 3H), 5.34 (s, 2H), 7.09-7.06 (m, 2H), 7.85-7.69 (m, 3H), 7.36-7.19 (m, 3H), 7.75 (s, 1H) ppm.
¹³C NMR (126 MHz, CDCl₃): δ 14.1, 47.3, 109.5, 119.3, 122.2, 122.5, 126.4, 128.1, 129.2, 135.5, 136.0, 142.7, 152.0 ppm.

Preparative Example F

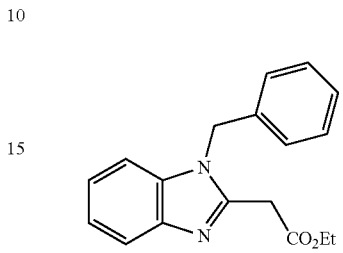

Compound from Preparative Example E (610 mg, 2.74 mmol) was dissolved in dry THF (5 mL). To the solution was added DIPEA (1.5 mL 8.22 mmol) and methyl chloroformate (0.45 mL, 5.76 mmol). The reaction mixture was stirred at 25° C. for 18 hrs, then it was poured into water (50 mL) and extracted with EtOAc (3×25 mL). The combined organic extracts were washed by brine (25 mL), dried over MgSO₄ and concentrated. The residue was purified by column chromatography on silica gel (EtOAc) to afford the product as a yellow solid (657 mg, 86%).
¹H NMR (500 MHz, CDCl₃): δ 3.55 (s, 3H), 3.88 (s, 2H), 5.32 (s, 2H), 6.97 (d, J=6.4 Hz, 2H), 7.32-7.09 (m, 6H), 7.70 (d, J=7.7 Hz, 1H) ppm.
¹³C NMR (126 MHz, CDCl₃): δ 34.7, 47.5, 52.6, 110.0, 120.0, 122.5, 123.1, 126.4, 128.1, 129.1, 135.7, 135.8, 142.7, 147.9, 168.7 ppm.
HRMS calculated for C₁₈H₁₉N₂O₂ [M+H]⁺ 281.1285, found 281.1291.

Preparative Example G

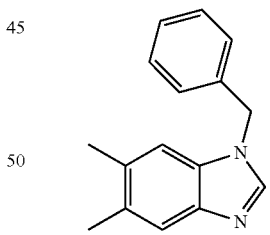

NaH (0.91 g, 22.5 mmol) was suspended in dry DMF (10 mL) and the mixture was cooled to 0° C. A solution of 5,6-dimethyl-1H-benzo[d]imidazole (3.0 g, 20.5 mmol) in DMF (10 mL) was added and the mixture was stirred at 25° C. for 50 min. Then, benzyl bromide (2.7 mL, 22.5 mmol) was added and the mixture was stirred at 25° C. for 16 hrs. The precipitate was collected by filtration and washed with Et₂O (3×25 mL). The crude product was obtained as a light brown solid (4.52 g, 93%) and used in the next step without further purification.
¹H NMR (500 MHz, DMSO-d₆): δ 2.27 (s, 3H), 2.28 (s, 3H), 5.43 (s, 1H), 7.30-7.22 (m, 4H), 7.34-7.36 (m, 2H), 7.42 (s, J=22.5 Hz, 1H), 8.23 (s, 1H) ppm.

<sup>13</sup>C NMR (126 MHz, DMSO-d$_6$): δ 19.8, 20.0, 47.4, 110.5, 119.5, 127.1, 127.5, 128.6, 129.8, 130.9, 132.2, 137.2, 142.2, 143.3 ppm.

HRMS calculated for C$_{16}$H$_{17}$N$_2$ [M+H]$^+$ 237.1386, found 237.1390.

Preparative Example H

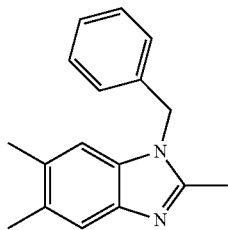

Compound from Preparative Example G (0.5 g, 2.11 mmol) was suspended in anhydrous THF (4 mL) and dioxane (2 mL). The mixture was cooled to −40° C. and 2.7 M n-BuLi in heptane (4.7 mL, 1.26 mmol) was added. The mixture was stirred at −40° C. for 40 min, then MeI (0.08 mL, 1.26 mmol) was added and the mixture was stirred at 25° C. for 12 hrs. The mixture was poured into saturated aqueous solution of NH$_4$Cl (20 mL) and extracted with EtOAc (3×20 mL). The combined organic extracts were dried over MgSO$_4$ and concentrated. The residue was purified by column flash chromatography on silica gel (EtOAc) to afford the product as a white solid (0.16 g, 61%).

$^1$H NMR (500 MHz, CDCl$_3$): δ 2.24 (s, 3H) 2.28 (s, 3H), 2.43 (s, 3H), 5.18 (s, 2H), 6.90 (s, 1H), 6.94 (s, 1H), 7.26-7.17 (m, 4H), 7.40 (s, 1H) ppm.

$^{13}$C NMR (126 MHz, CDCl$_3$): δ 13.9, 20.2, 20.5, 47.0, 109.6, 119.3, 126.2, 127.8, 129.0, 130.7, 131.2, 134.1, 136.2, 141.3, 151.0 ppm.

Preparative Example I

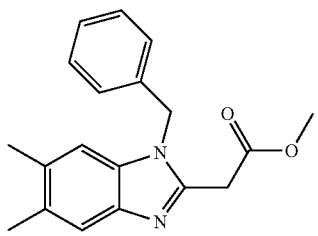

By essentially same procedure set forth in Preparative Example F, using the compound from Preparative Example H instead of the compound from Preparative Example E, compound I was prepared.

$^1$H NMR (500 MHz, CDCl$_3$): δ 2.24 (s, 3H), 2.28 (s, 3H), 3.51 (s, 3H), 3.83 (s, 2H), 5.26 (s, 2H), 6.92 (s, 1H), 6.98-6.93 (m, 2H), 7.22-7.17 (m, 3H), 7.45 (s, 1H) ppm.

$^{13}$CNMR (126 MHz, CDCl$_3$): δ 20.3, 20.6, 34.6, 47.3, 52.5, 110.1, 120.0, 126.3, 128.0, 129.0, 131.3, 132.2, 134.4, 141.2, 147.0, 168.8 ppm.

HRMS calculated for C$_{38}$H$_{40}$N$_4$O$_4$Na [2M+Na]$^+$ 639.2942, found 639.2938.

Preparative Example J

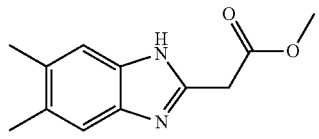

Compound from Preparative Example I (0.16 g, 0.52 mmol) was dissolved in degassed EtOH (5 mL). Pd(OH)$_2$/C (5 mg) was added and the mixture was refluxed under H$_2$ for 4 hrs. The mixture was filtered through Celite and the solvent was evaporated. The product was obtained as a white solid (96 mg, 84%).

$^1$H NMR (500 MHz, DMSO-d$_6$): δ 2.29 (s, 6H), 3.66 (d, J=8.1 Hz, 3H), 3.90 (d, J=10.7 Hz, 2H), 7.26 (s, 2H), 12.06 (s, 1H) ppm.

$^{13}$C NMR (126 MHz, DMSO-d$_6$): δ 19.9, 34.9, 21.0, 129.7, 146.6, 169.2 ppm.

HRMS calculated for C$_{12}$H$_{15}$N$_2$O$_2$ [M+H]$^+$ 219.1128, found 219.1131.

Preparative Example K

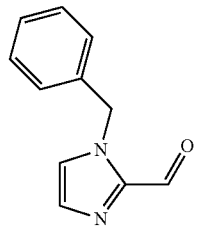 [SMILES: O=Cc1nccn1Cc1ccccc1]

1-benzylimidazole (4.2 g, 26.6 mmol) was dissolved in anhydrous THF (30 mL). The solution was cooled to −40° C. and n-BuLi (2.7 M in heptane) (10.75 mL, 29 mmol) was added and the mixture was stirred at at −40° C. for 40 min. Then, solution of DMF (40.0 mmol, 2.9 mL) and THF (3 mL) was added and the mixture was stirred at 25° C. for 8 hrs. The mixure was poured into saturated aqueous solution of NH$_4$Cl (50 mL) and extracted with EtOAc (3×25 mL). The organic phase was dried with MgSO$_4$, the solvent was evaporated and the residue was purified by column chromatography on silica gel (EtOAc). The product was isolated as a yellow wax (3.42 g, 69%).

$^1$H NMR (500 MHz, CDCl$_3$): δ 5.63 (s, 2H), 7.15 (s, 1H), 7.22 (d, J=6.7 Hz, 2H), 7.31 (s, 1H), 7.38-7.32 (m, 3H), 9.87 (d, J=0.7 Hz, 1H) ppm.

$^{13}$C NMR (126 MHz, CDCl$_3$): δ 51.0, 126.3, 127.9, 128.5, 129.1, 132.0, 135.9, 143.5, 182.3 ppm. HRMS calculated for C$_{11}$H$_{11}$N$_2$O [M+H]$^+$ 187.0866, found 187.0870.

Preparative Example L

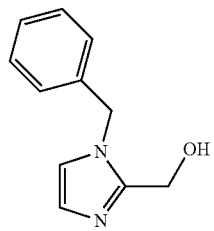 [SMILES: OCc1nccn1Cc1ccccc1]

Compound from Preparative example K (3.42 g, 18.4 mmol) was dissolved in ethanol (20 mL). The solution was cooled to 0° C., NaBH$_4$ (0.35 g, 9.19 mmol) was added and the mixture was stirred at 25° C. for 10 hrs. The resulting mixture was poured into a mixture of water (50 mL) with saturated solution of NH$_4$Cl (10 mL) and then it was extracted with EtOAc (3×25 mL). The combined organic phases were dried over MgSO$_4$ and concentrated. The product was obtained as a white solid (3.32 g, 96%).

$^1$H NMR (500 MHz, CDCl$_3$): δ 4.66 (d, J=7.0 Hz, 2H), 5.25 (s, 2H), 6.08 (s, 1H), 6.83 (d, J=9.2 Hz, 1H), 6.91 (d, J=14.3 Hz, 1H), 7.17 (d, J=7.1 Hz, 2H), 7.39-7.29 (m, 3H) ppm.

$^{13}$C NMR (126 MHz, CDCl$_3$): δ 49.8, 56.0, 120.7, 127.0, 127.4, 128.2, 129.0, 136.5, 148.3 ppm.

HRMS calculated for C$_{11}$H$_{13}$N$_2$O [M+H]$^+$ 189.1022, found 189.1022.

Preparative Example M

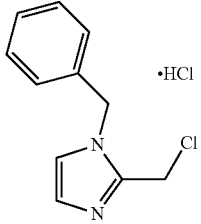 [SMILES: ClCc1nccn1Cc1ccccc1 ; Cl]

Compound from Preparative Example L (1.94 g, 10.32 mmol) was dissolved in anhydrous dichloromethane (15 mL) and the solution was cooled to 0° C. SOCl$_2$ (753 mg, 6.38 mmol) was added slowly and the mixture was stirred at 25° C. for 16 hrs. Et$_2$O (15 mL) was added and the resulting precipitate was collected by filtration and washed with Et$_2$O (20 mL). The product was obtained as a white solid (2.28 g, 91%).

$^1$H NMR (500 MHz, DMSO-d$_6$): δ 5.25 (s, 2H), 5.51 (s, 2H), 7.56-7.29 (m, 3H), 7.90-7.65 (m, 2H) ppm.

$^{13}$C NMR (126 MHz, DMSO-d$_6$): δ 31.6, 50.1, 120.3, 123.5, 128.1, 128.5, 128.8, 134.3, 141.7 ppm.

Preparative Example N

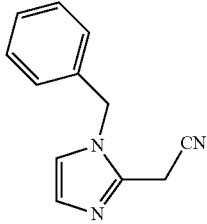

Compound from Preparative example M (77 mg, 0.37 mmol) was dissolved in anhydrous DMSO (1.5 mL) and KCN (50 mg, 0.74 mmol) was added. The mixture was stirred at 25° C. for 18 hrs; then it was poured into water (20 mL) and extracted with EtOAc (3×15 mL). The organic extracts were washed with brine (25 mL), dried over MgSO$_4$ and concentrated. The product was isolated as a yellow solid (66 mg, 89%).

$^1$H NMR (500 MHz, CDCl$_3$): δ 3.74 (s, 2H), 5.20 (s, 2H), 6.98 (s, 1H), 7.06 (s, 1H), 7.13 (d, J=7.8 Hz, 2H), 7.43-7.34 (m, 3H) ppm.

$^{13}$C NMR (126 MHz, CDCl$_3$): δ 17.5, 50.4, 114.8, 122.4, 127.1, 128.6, 128.8, 129.4, 135.0, 136.8 ppm.

HRMS calculated for C$_{12}$H$_{12}$N$_3$ [M+H]$^+$ 198.1026, found 198.1023.

Preparative Example O

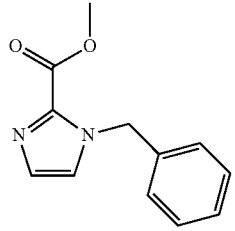 [SMILES: COC(=O)c1nccn1Cc1ccccc1]

Compound from Preparative Example K (1.02 g, 5.48 mmol) was dissolved in MeOH (10 mL). K$_2$CO$_3$ (1.51 g, 10.1 mmol) and I$_2$ (2.38 g, 10.1 mmol) were added and the mixture was refluxed for 18 hrs. The mixture was poured into 10% aqueous solution of Na$_2$S$_2$O$_3$ (50 mL) and extracted with EtOAc (3×25 ml). The combined organic extracts were dried over MgSO$_4$ and the solvent was evaporated. The residue was purified by column chromatography on silica gel (EtOAc). The product was obtained as a white solid (0.83g, 70%).

$^1$H NMR (500 MHz, CDCl$_3$): δ 3.93 (s, 3H), 5.64 (s, 2H), 7.10-7.05 (m, 1H), 7.24-7.15 (m, 3H), 7.38-7.28 (m, 3H) ppm.

$^{13}$C NMR (126 MHz, CDCl$_3$): δ 51.7, 52.4, 125.4, 127.5, 128.2, 129.0, 130.0, 136.3, 136.4, 159.7, 159.7 ppm.

HRMS calculated for C$_{12}$H$_{13}$N$_2$O$_2$ [M+H]$^+$ 217.0972, found 217.0972.

Preparative Example 1A

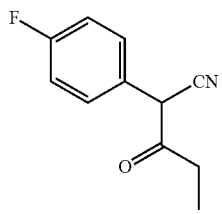

A solution of 2-(4-fluorophenyl)acetonitrile (1.13 g, 8.3 mmol) in anhydrous THF (4 mL) was added under N$_2$ to NaH (60% suspension in mineral oil, 0.67 g, 16.7 mmol). The mixture was stirred for 20 min, then methyl propionate (0.73 g, 8.3 mmol) was added and the reaction mixture was stirred at 25° C. for additional two hrs. The mixture was cooled to 0° C. and saturated aqueous solution of NH$_4$Cl (50 mL) was added. The mixture was extracted with EtOAc (3×75 mL). The organic extracts were dried over MgSO$_4$, filtered, and the solvent was evaporated. The residue was purified by flash chromatography on silica gel (hexane/EtOAc—3:1) to yield the product as a yellow-orange oil (1.46 g, 92%).

$^1$H NMR (500 MHz, CDCl$_3$): δ 1.06 (t, 2H, J=7.2 Hz). 2.74-2.56 (m, 1H), 4.68 (s. 1H), 7.17-7.09 (m, 1H), 7.42-7.35 (m, 1H) ppm.

$^{13}$C NMR (125 MHz, CDCl$_3$): δ 7.8, 32.5, 49.9, 116.4, 116.9 (d, J=22.0 Hz), 126.0 (d, J=3.4 Hz), 130.0 (d, J=8.3 Hz), 163.3 (d. J=249.6 Hz), 199.4 ppm.

HRMS calculated for C$_{11}$H$_9$FNO [M−H]$^-$ 190.0674, found 190.0672.

Preparative Example 1B

By essentially same procedure set forth in Preparative Example 1A, using methyl isobutyrate instead of methyl propionate, compound 1B given below was prepared.

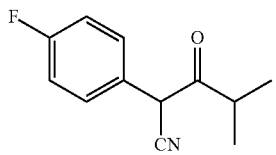

White solid.

MP=58.5-59.8° C.

$^1$H NMR (500 MHz, CDCl$_3$): δ 1.25 (d, 1H, J=7.0 Hz), 3.05 (hept, 1H. J=7.0 Hz), 4.98 (s, 1H), 7.15-7.10 (m, 1H), 7.31-7.27 (m, 1H) ppm.

$^{13}$C NMR (125 MHz, CDCl$_3$): δ 18.8, 19.0, 39.0, 48.5, 116.4, 116.9 (d, J=21.1 Hz), 125.9 (d, J=3.1 Hz), 130.2 (d, J=8.6 Hz), 163.2 (d, J=249.6 Hz), 202.5 ppm.

HRMS calculated for C$_{12}$H$_{11}$FNO [M−H]$^-$ 204.0830, found 204.0838.

Preparative Example 1C

By essentially same procedure set forth in Preparative Example 1A, using ethyl formate instead of methyl propionate, compound 1C given below was prepared in 60% yield.

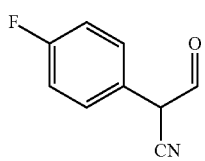

Off-white solid.

MP=145.0-146.0° C.

$^1$H NMR (500 MHz, DMSO-d$_6$): δ (ppm) 7.16-7.21 (m, 2H), 7.20-7.27 (m, 2H), 7.44 (ddd, J=6.6, 5.2, 2.1 Hz, 2H), 7.65 (s, 1H), 7.69 (ddd, J=8.6, 5.4, 2.7 Hz, 2H), 7.97 (s, 1H), 12.14 (s, 2H).

$^{13}$C NMR (125 MHz, DMSO-d$_6$): δ (ppm) 88.5, 88.8, 115.4 (d, J=21.7 Hz), 115.7 (d, J=21.8 Hz), 116.7, 120.1, 126.1 (d, J=8.1 Hz), 128.0 (d, J=3.5 Hz), 128.4 (d, J=8.1 Hz), 128.6 (d, J=2.8 Hz), 157.8, 160.5 (d, J=244.2 Hz), 160.9 (d, J=243.4 Hz).

HRMS calculated for C$_9$H$_5$FNO [M−H]$^-$ 162.0361, found 162.0360.

Preparative Example 2A

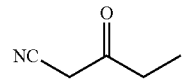

A solution of methyl propionate (3.82 g, 43.3 mmol) and acetonitrile (5.33 g, 130.0 mmol) in anhydrous THF (25 mL) was added under nitrogen to NaH (60% suspension in mineral oil, 5.20 g, 130.0 mmol) and the mixture was refluxed for 4 hrs. The reaction mixture was cooled to 0° C., quenched with saturated aqueous solution NH$_4$Cl (100 mL), and extracted with EtOAc (3×75 mL). The organic extracts were dried over MgSO$_4$, filtered, and the solvent was evaporated. The residue was purified by column chromatography on silica gel (hexane/EtOAc—4:1) to yield the product as a colorless liquid (3.5 g, 90%).

$^1$H NMR (500 MHz, CDCl$_3$): δ 1.14 (t, 3H, J=7.2 Hz), 2.66 (q, 2H, J=7.2 Hz), 3.46 (s, 2H) ppm.

$^{13}$C NMR (125 MHz, CDCl$_3$): δ 7.6, 31.8, 35.8, 114.0, 198.1 ppm.

HRMS calculated for C$_5$H$_6$NO [M−H]$^-$ 96.0455, found 96.0462.

Preparative Examples 2B-2K

By essentially same procedure set forth in Preparative Example 2A, using the indicated esters instead of methyl propionate, compounds given below were prepared.

Preparative Example 2B

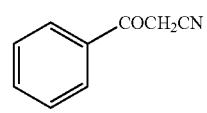

Prepared from methyl benzoate.

White solid.

MP=72.0-73.2° C.

$^1$H NMR (500 MHz, CDCl$_3$): δ 4.09 (s, 2H), 7.54 (t, 2H, J=7.80 Hz), 7.67 (t, 1H, J=7.50 Hz), 7.93 (d, 2H, J=7.3 Hz).

$^{13}$C NMR (125 MHz, CDCl$_3$): δ 29.6, 113.9, 128.7, 129.4, 130.4, 133.8, 134.5, 134.9, 187.3 ppm.

HRMS calculated for C$_9$H$_6$NO [M−H]$^-$ 144.0455, found 144.0457.

Preparative Example 2C

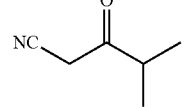

Prepared from methyl isobutyrate.

Pale yellow oil.

$^1$H NMR (500 MHz, CDCl$_3$): δ 1.19 (d, 6H, J=6.90 Hz), 2.82 (hept, 1H, J=6.90 Hz), 3.52 (s, 2H) ppm.

$^{13}$C NMR (125 MHz, CDCl$_3$): δ 18.0, 30.2, 40.7, 114.0, 201.3 ppm.

HRMS calculated for C$_6$H$_8$NO [M+H]$^+$ 110.0611, found 110.1618.

Preparative Example 2D

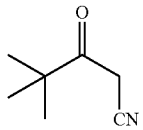

Prepared from methyl pivalate.
White solid.
MP=67.5-68.4° C.
$^1$H NMR (500 MHz, CDCl$_3$): δ 1.20 (s, 9H), 3.63 (s, 2H) ppm.
$^{13}$C NMR (125 MHz, CDCl$_3$): δ 26.3, 27.6, 44.8, 114.2, 202.9 ppm.
HRMS calculated for C$_7$H$_{10}$NO [M−H]$^−$ 124.0768, found 124.0774.

Preparative Example 2E

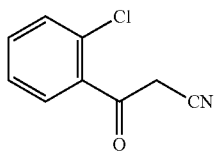 [SMILES: N#CCC(=O)c1ccccc1Cl]

Prepared from methyl 2-chlorobenzoate.
Yellow solid.
MP=57.0-58.1° C.
$^1$H NMR (500 MHz, CDCl$_3$): δ 4.15 (s, 2H), 7.39-7.44 (m, 1H), 7.46-7.54 (m, 2H), 7.65 (dd, 1H, J=7.7, 1.4 Hz) ppm;
13C NMR (500 MHz, CDCl3): δ 33.1, 113.5, 127.7, 130.6, 131.2, 131.9, 133.9, 135.9, 189.6 ppm.
HRMS calculated for C$_7$H$_5$ClON [M−H]$^−$ 178.0065, found 178.0067.

Preparative Example 2F

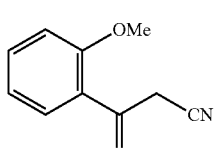

Prepared from methyl 2-methoxybenzoate.
White solid.
MP=88.9-89.7° C.
$^1$H NMR (500 MHz, CDCl$_3$): δ 3.98 (s, 3H), 4.09 (s, 2H), 7.03 (d, 1H, J=8.4), 7.09-7.05 (m, 1H), 7.65-7.53 (m, 1H), 7.87 (dd, 1H, J=7.8, 1.8) ppm.
$^{13}$C NMR (125 MHz, CDCl$_3$): δ 34.3, 56.0, 112.0, 114.8, 121.5, 124.8, 131.6, 135.9, 159.4, 188.2 ppm.

HRMS calculated for C$_{10}$H$_7$NO$_2$ [M−H]$^−$ 174.0561, found 174.0565.

Preparative Example 2G

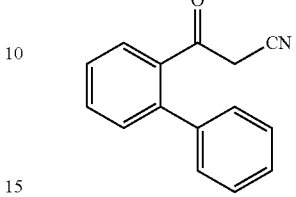

Prepared from methyl ester of biphenyl-2-carboxylic acid.
Yellow oil.
$^1$H NMR (500 MHz, CDCl$_3$): δ 3.21 (s, 2H), 7.40-7.35 (m, 2H), 7.55-7.45 (m, 5H), 7.66-7.59 (m, 2H) ppm.
$^{13}$C NMR (125 MHz, CDCl$_3$): δ 14.4, 32.3, 60.6, 113.8, 128.2, 129.1, 129.6, 130.7, 132.5, 137.6, 139.8, 141.0, 193.7 ppm.
HRMS calculated for C$_{15}$H$_{10}$NO [M−H]$^−$ 220.0768, found 220.0765.

Preparative Example 2H

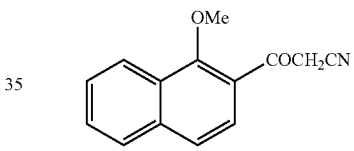

Prepared from methyl 1-methoxy-2-naphthoate.
$^1$H NMR (500 MHz, CDCl$_3$): δ 4.08 (s, 3H), 4.29 (s, 2H), 7.68-7.61 (m, 2H), 7.69 (d, J=8.5 Hz, 1H), 7.80 (d, J=8.7 Hz, 1H), 7.91 (d, J=7.5 Hz, 1H), 8.22 (d, J=8.1 Hz, 1H) ppm.
$^{13}$C NMR (126 MHz, CDCl$_3$): δ 33.3, 64.7, 114.6, 123.8, 125.2, 125.2, 125.3, 127.4, 127.8, 128.7, 129.6, 159.0, 188.9 ppm.
HRMS calculated for C$_{12}$H$_{13}$N$_2$O$_2$ [M+H]$^+$ 226.0862, found 226.0862.

Preparative Example 2I

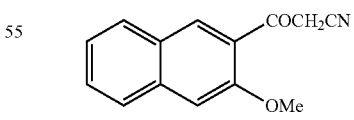

Prepared from methyl 3-methoxy-2-naphthoate.
$^1$H NMR (500 MHz, CDCl$_3$): δ 4.08 (s, 3H), 4.18 (s, 2H), 7.43 (m, 1H), 7.59 (m, 1H), 7.78 (d, J=8.3 Hz, 1H), 7.90 (d, J=8.2 Hz, 1H), 8.39 (s, 1H) ppm.
$^{13}$C NMR (126 MHz, CDCl$_3$): δ 34.1, 55.9, 107.0, 114.6, 125.2, 126.2, 126.6, 128.1, 129.6, 129.8, 133.5, 137.2, 155.3, 188.8 ppm.

HRMS calculated for $C_{14}H_{12}NO_2$ [M+H]$^+$ 226.0862, found 226.0867.

Preparative Example 2J

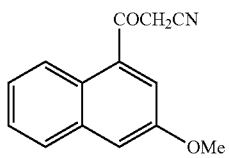

Prepared from methyl 3-methoxy-1-naphthoate.

$^1$H NMR (500 MHz, CDCl$_3$): δ 4.05 (s, 2H), 4.07 (s, 3H), 7.32 (d, J=9.1 Hz, 1H), 7.47-7.40 (m, 1H), 7.60-7.53 (m, 1H), 7.83 (d, J=8.2 Hz, 1H), 7.97 (d, J=8.7 Hz, 1H) 8.02 (d, J=9.1 Hz, 1H) ppm.

$^{13}$C NMR (126 MHz, CDCl$_3$): δ 34.4, 56.6, 112.2, 114.7, 120.3, 123.7, 124.9, 128.5, 198.0, 129.1, 130.9, 134.5, 156.4, 192.5 ppm.

HRMS calculated for $C_{14}H_{12}NO_2$ [M+H]$^+$ 226.0863, found 226.0867.

Preparative Example 2K

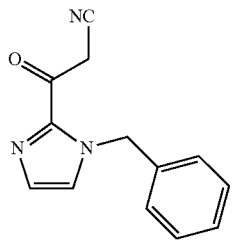 [SMILES: N#CCC(=O)c1nccn1Cc1ccccc1]

Prepared from the compound from Preparative Example O.

$^1$H NMR (500 MHz, CDCl$_3$): δ 4.31 (s, 2H), 5.61 (s, 2H), 7.20 (d, J=3.5 Hz, 1H), 7.25-7.21 (m, 3H), 7.40-7.33 (m, 3H) ppm.

$^{13}$C NMR (126 MHz, CDCl$_3$): δ 29.7, 52.0, 114.1, 127.7, 127.9, 128.6, 129.2, 130.8, 135.6, 140.6, 179.2 ppm.

HRMS calculated for $C_{13}H_{12}N_3O$ [M+H]$^+$ 226.0975, found 226.0977.

Preparative Example 3A

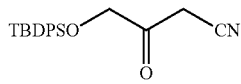

n-BuLi solution in hexane (2.7 M, 0.6 ml, 1.62 mmol) was added under nitrogen to a solution of acetonitrile (93.0 mg, 2.28 mmol) in anhydrous THF (5 mL) at −78° C. The reaction mixture was stirred at −78° C. for 30 min, then a solution of compound from Preparative Example A (0.50 g, 1.52 mmol) in anhydrous THF (10 mL) was added dropwise and the mixture was stired at −78° C. for 2 hrs. The reaction mixture was quenched with saturated aqueous solution NH$_4$Cl (10 mL) and extracted with CH$_2$Cl$_2$ (3×75 mL). The organic extracts were dried over MgSO$_4$, filtered, and the solvent was evaporated. The residue was purified by flash chromatography on silica gel (eluent: hexane/EtOAc—5:1) to yield the product as a colorless oil (365 mg, 71%).

$^1$H NMR (500 MHz, CDCl$_3$): δ 1.13 (s, 9H), 3.74 (s, 2H), 4.28 (s, 2H), 7.46-7.41 (m, 4H), 7.51-7.47 (m, 2H), 7.66-7.62 (m, 4H) ppm.

$^{13}$C NMR (125 MHz, CDCl$_3$): δ 19.3, 26.9, 29.6, 69.2, 113.5, 128.3, 130.6, 131.8, 135.6, 198.3 ppm.

HRMS calculated for $C_{20}H_{22}NO_2Si$ [M−H]$^-$ 336.1425, found 336.1429.

Preparative Examples 3B-3G

By essentially same procedure set forth in Preparative Example 3A, using the indicated esters instead of compound from Preparative Example A, compounds given below were prepared.

Preparative Example 3B

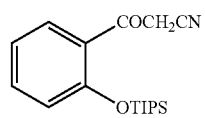

Prepared from compound from Preparative Example B.

Colorless oil.

$^1$H NMR (125 MHz, CDCl$_3$): δ 1.15 (d, 18H, J=7.5 Hz), 1.44-1.34 (m, 3H), 4.15 (s, 2H), 6.92 (d, 1H, J=8.3 Hz), 7.04 (t, 1H, J=7.5 Hz), 7.47-7.39 (m, 1H), 7.74 (dd, 1H, J=7.8, 1.8 Hz) ppm.

$^{13}$C NMR (125 MHz, CDCl$_3$): δ 13.6, 18.1, 35.5, 114.4, 119.8, 121.7, 127.3, 131.3, 135.1, 156.0, 189.3 ppm.

HRMS calculated for $C_{18}H_{29}NO_2Si$ [M+H]$^+$ 318.1884, found 318.1886.

Preparative Example 3C

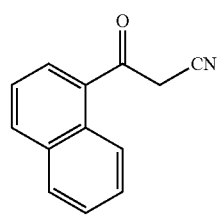 [SMILES: N#CCC(=O)c1cccc2ccccc12]

Prepared from methyl 1-naphthoate.

Yellow solid.

MP=99.0-101.0° C.

$^1$H NMR (500 MHz, CDCl$_3$): δ 4.20 (s, 2H), 7.58-7.54 (m, 1H), 7.64-7.58 (m, 1H), 7.72-7.66 (m, 1H), 7.92 (t, 2H, J=8.2 Hz), 8.12 (d, 1H, J=8.2 Hz), 8.82 (d, 1H, J=8.7 Hz) ppm.

$^{13}$C NMR (125 MHz, CDCl$_3$): δ 32.0, 114.2, 124.4, 125.8, 127.4, 128.9, 129.4, 129.7, 130.6, 131.8, 134.3, 135.4, 189.7 ppm.

Preparative Example 3D

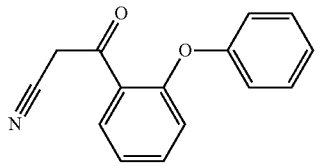 [SMILES: N#CCC(=O)c1ccccc1Oc1ccccc1]

Prepared from methyl 2-phenoxybenzoate.

$^1$H NMR (500 MHz, CDCl$_3$): δ 4.16 (s, 2H), 6.85 (dd, J=8.4, 1.0 Hz, 1H), 7.10 (dt, J=7.7, 1.1 Hz, 2H), 7.16-7.21 (m, 1H), 7.22-7.28 (m, 1H), 7.40-7.46 (m, 2H), 7.49 (ddd, J=8.4, 7.3, 1.8 Hz, 1H), 7.96 (dd, J=7.9, 1.8 Hz, 1H) ppm.

$^{13}$C NMR (125 MHz, CDCl$_3$): δ 34.2, 114.4, 117.9, 120.1, 123.5, 125.4, 126.2, 130.6, 131.6, 135.6, 154.9, 157.7, 187.8 ppm.

HRMS calculated for C$_{15}$H$_{12}$NO$_2$ [M+H]$^+$ 238.0863, found 238.0865.

Preparative Example 3E

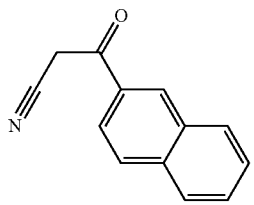 [SMILES: N#CCC(=O)c1ccc2ccccc2c1]

Prepared from methyl 2-naphthoate.

$^1$H NMR (500 MHz, CDCl$_3$): δ 4.21 (s, 2H), 7.61 (ddd, J=8.1, 6.9, 1.3 Hz, 1H), 7.67 (ddd, J=8.2, 6.9, 1.3 Hz, 1H), 7.91 (dd, J=8.2, 1.1 Hz, 1H), 7.93-8.02 (m, 3H), 8.37-8.47 (m, 1H) ppm.

$^{13}$C NMR (125 MHz, CDCl$_3$): δ (ppm) 29.6, 114.0, 123.6, 127.6, 128.1, 129.4, 129.7, 129.9, 130.9, 131.8, 132.5, 136.3, 187.1 ppm.

HRMS calculated for C$_{13}$H$_8$NO [M−H]$^-$ 194.0611, found 194.0605.

Preparative Example 3F

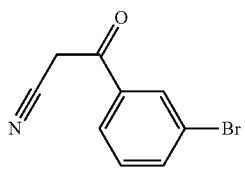 [SMILES: N#CCC(=O)c1cccc(Br)c1]

Prepared from methyl 3-bromobenzoate.
Yellow wax.

$^1$H NMR (500 MHz, CDCl$_3$): δ 4.06 (s, 2H), 7.42 (t, J=7.9 Hz, 1H), 7.79 (ddd, J=8.0, 2.0, 1.0 Hz, 1H), 7.84 (ddd, J=7.8, 1.8, 1.0 Hz, 1H), 8.05 (t, J=1.9 Hz, 1H) ppm.

$^{13}$C NMR (125 MHz, CDCl$_3$): δ 29.6, 113.4, 123.7, 127.1, 130.8, 131.6, 136.1, 137.8, 186.0 ppm.

Preparative Example 3G

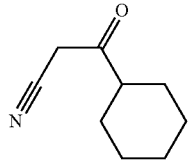 [SMILES: N#CCC(=O)C1CCCCC1]

Prepared from methyl cyclohexanecarboxylate.

$^1$H NMR (500 MHz, CDCl$_3$): δ 1.14-1.45 (m, 5H), 1.65-1.73 (m, 1H), 1.77-1.86 (m, 2H), 1.85-1.96 (m, 2H), 2.55 (tt, J=11.1, 3.5 Hz, 1H), 3.49 (s, 2H) ppm.

$^{13}$C NMR (125 MHz, CDCl$_3$): δ 25.4, 25.7, 28.3, 30.4, 50.1, 114.0, 200.5.

HRMS calculated for C$_9$H$_{12}$NO [M−H]$^-$ 150.0956, found 150.0951.

Preparative Example 3H

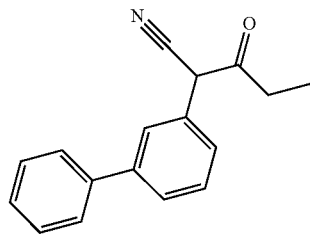 [SMILES: CCC(=O)C(C#N)c1cccc(-c2ccccc2)c1]

Under atmosphere of nitrogen, degassed anhydrous DMF (3 mL) was added to a mixture of compound from Preparative Example 2A (0.113 g, 1.02 mmol), 3-bromobiphenyl (0.25 g, 1.07 mmol), Pd(OAc)$_2$ (6 mg, 0.025 mmol), PPh$_3$ (27 mg, 0.1 mmol) and Cs$_2$CO$_3$ (0.99 g, 3.05 mmol). The mixture was stirred at 150° C. for 1 hr, then it was cooled to 25° C. and saturated aqueous solution of NH$_4$Cl (10 mL) and EtOAc (20 mL) were added. The organic phase was separated, washed with brine (10 mL), dried over MgSO$_4$, filtered, and concentrated. The residue was purified by column chromatography on silica gel (hexane:EtOAc, 1:0 to 1:2) to afford the product as a pale yellow oil (116 mg, 46%).

$^1$H NMR (500 MHz, CDCl$_3$): δ 1.06 (t, J=7.2 Hz, 3H), 2.57-2.68 (m, 1H), 2.68-2.79 (m, 1H), 4.75 (s, 1H), 7.36-7.42 (m, 2H), 7.44-7.53 (m, 3H), 7.56-7.66 (m, 4H) ppm.

$^{13}$C NMR (126 MHz, DMSO-d$_6$): δ 7.8, 33.4, 50.8, 116.5, 126.8, 127.3, 128.1, 129.1, 130.1, 130.6, 140.0, 143.0, 199.5 ppm.

HRMS calculated for C$_{17}$H$_{16}$NO [M+H]$^+$ 250.1226, found 250.1222.

Preparative Example 3I

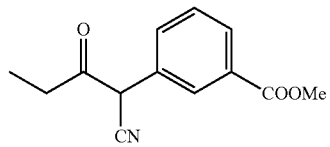 [SMILES: CCC(=O)C(C#N)c1cccc(C(=O)OC)c1]

By essentially same procedure set forth in Preparative Example 3H, using methyl 3-bromobenzoate instead of 3-bromobiphenyl, compound 3I was prepared in 33% yield.

$^1$H NMR (500 MHz, CDCl$_3$): δ 1.08 (t, J=7.2 Hz, 3H), 2.76-2.59 (m, 2H), 3.96 (s, 3H), 4.76 (s, 1H), 7.55 (t, J=7.7 Hz, 1H), 7.63-7.61 (m, 1H), 8.12-8.07 (m, 2H) ppm.

$^{13}$C NMR (126 MHz, CDCl$_3$): δ 7.7, 33.7, 50.3, 52.6, 116.1, 129.3, 129.9, 130.5, 130.6, 131.8, 132.4, 166.1, 199.0 ppm.

HRMS calculated for C$_{13}$H$_{14}$NO$_3$ [M+H]$^+$ 232.0968, found 232.0965.

Preparative Example 4A

To a solution of compound from Preparative Example 1A (1.4 g, 7.3 mmol) in ethanol (25 mL) were added aqueous 64% hydrazine hydrate (0.8 g, 14.6 mmol) and methanesulfonic acid (0.1 g, 0.7 mmol). The mixture was refluxed under N$_2$ for 4 hrs; then the solvent was evaporated. Saturated aqueous solution of NaHCO$_3$ (100 mL) was added to the residue and the mixture was extracted with EtOAc (3×50 mL). The organic extracts were dried over MgSO$_4$, filtered, and the solvent was evaporated. The residue was purified by flash chromatography on silica gel (eluent: hexane/EtOAc— 1:1) to yield the product as a white solid (365 mg, 71%).

$^1$H NMR (500 MHz, DMSO-d$_6$): δ 1.23 (q, 3H, J=7.5 Hz), 2.69 (q, 2H, J=7.5 Hz), 3.48 (s, 2H, J=77.8 Hz), 7.27-7.40 (m, 2H), 7.42-7.52 (m, 2H), 8.51 (s, 1H) ppm.

$^{13}$C NMR (125 MHz, DMSO-d$_6$): δ 13.2, 18.4, 102.7, 115.2 (d, J=21.2 Hz), 129.9 (d, J=7.9 Hz), 130.2 (d, J=2.8 Hz), 143.3, 150.5, 160.1 (d, J=241.7 Hz) ppm.

HRMS calculated for C$_{11}$H$_{11}$FN$_3$ [M+H]$^-$ 204.0942, found 204.0948.

Preparative Examples 4B-4W

By essentially same procedure set forth in Preparative Example 4A, compounds given below were prepared from the indicated ketonitriles.

Preparative Example 4B

Prepared from compound from Preparative Example 2A. Brown oil.

$^1$H NMR (500 MHz, DMSO-d$_6$): δ 1.11 (t, 3H, J=7.57 Hz), 2.40 (q, 2H, J=7.57 Hz), 5.18 (s, 1H) ppm.

$^{13}$C NMR (125 MHz, DMSO-d$_6$): δ 13.5, 19.1, 88.9, 146.5, 153.7 ppm.

HRMS calculated for C$_5$H$_{10}$N$_3$ [M+H]$^+$ 112.0869, found 112.0874.

Preparative Example 4C

Prepared from compound from Preparative Example 2B. White solid.

MP=106.7-107.5° C.

$^1$H NMR (500 MHz, DMSO-d$_6$): δ 4.78 (s, 2H), 5.75 (s, 1H), 7.25 (t, 1H, J=7.3 Hz), 7.36 (t, 2H, J=7.6 Hz), 7.64 (d, 2H, J=7.3 Hz), 11.73 (s, 1H) ppm.

Preparative Example 4D

Prepared from compound from Preparative Example 1B. White solid.

$^1$H NMR (500 MHz, CDCl$_3$): δ 1.25 (d, 1H, J=7.0 Hz), 3.05 (kept, 1H, J=7.0 Hz), 4.98 (s, 1H), 7.15-7.10 (m, 1H), 7.31-7.27 (m, 1H) ppm.

$^{13}$C NMR (125 MHz, CDCl$_3$): δ 22.1, 25.4, 104.5, 116.1 (d, J=21.5 Hz), 131.3 (d, J=8.1 Hz), 148.4, 151.7, 175.2, 162.1 (d, J=246.9 Hz) ppm.

HRMS calculated for C$_5$H$_{10}$N$_3$ [M+H]$^+$ 112.0869, found 112.0874.

Preparative Example 4E

Prepared from compound from Preparative Example 2C. Dark brown wax.

MP=76.9-77.8° C.

$^1$H NMR (500 MHz, DMSO-d$_6$): δ 1.24 (d, 6H, J=6.90 Hz), 2.88 (hept, 1H, J=6.90 Hz), 5.31-5.58 (m, 4H, J=2.5 Hz).

$^{13}$C NMR (125 MHz, DMSO-d$_6$): δ 22.4, 26.3, 90.0, 90.1, 152.3, 154.6 ppm.

HRMS calculated for C$_6$H$_8$NO [M+H]$^+$ 110.0611, found 110.1618.

Preparative Example 4F

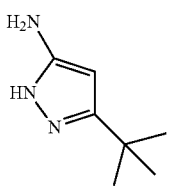

Prepared from compound from Preparative Example 2D.
Pink solid.
MP=77.0-77.5° C.
$^1$H NMR (500 MHz, DMSO-d$_6$): δ 1.18 (s, 9H), 4.51 (s, 2H), 5.18 (s, 1H), 10.91 (s, 2H) ppm.
$^{13}$C NMR (125 MHz, DMSO-d$_6$): δ 30.0, 30.6, 87.4, 153.3, 154.0 ppm.
HRMS calculated for C$_7$H$_{14}$N$_3$ [M+H]$^+$ 140.1182, found 140.1191.

Preparative Example 4G

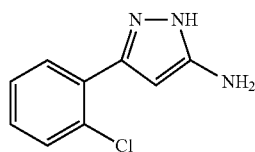 [SMILES: Nc1cc(-c2ccccc2Cl)n[nH]1]

Prepared from compound from Preparative Example 2E.
Yellow wax.
$^1$H NMR (500 MHz, DMSO-d$_6$): δ 4.82 (s, 1H), 5.84 (s, 1H), 7.31 (t, 1H, J=7.6 Hz), 7.36 (t, 1H, J=7.0 Hz), 7.48 (d, 1H, J=7.7 Hz), 7.67 (d, 1H, J=6.0 Hz) ppm.
$^{13}$C NMR (500 MHz, DMSO-d$_6$): δ 17.6, 24.7, 59.7, 127.1, 128.8, 129.9, 130.2, 130.6, 159.1 ppm.
HRMS calculated for C$_9$H$_9$ClN$_3$ [M+H]$^+$ 194.0480, found 140.0476.

Preparative Example 4H

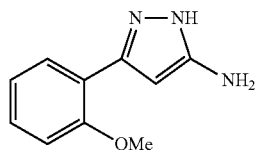 [SMILES: COc1ccccc1-c1cc(N)[nH]n1]

Prepared from compound from Preparative Example 2F.
Colorless wax.
$^1$H NMR (500 MHz, DMSO-d$_6$): δ 3.85 (s, 3H), 4.54 (s, 2H), 5.88 (s, 1H), 7.03-6.85 (m, 1H), 7.13-7.02 (m, 1H), 7.27 (t, 1H, J=7.2 Hz), 7.76-7.52 (m, 1H), 11.61 (d, 1H, J=97.7 Hz) ppm.
$^{13}$C NMR (500 MHz, DMSO-d$_6$): δ 55.3, 59.7, 91.3, 110.4, 111.8, 120.5, 126.1, 127.1, 128.5, 155.6 ppm.
HRMS calculated for C$_{10}$H$_{12}$N$_3$O [M+H]$^+$ 190.0975, found 190.0977.

Preparative Example 4I

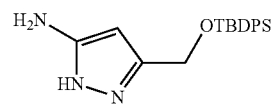

Prepared from compound from Preparative Example 3A.
Yellow wax.
$^1$H NMR (500 MHz, CDCl$_3$): δ 1.00 (s, 9H), 4.54 (s, 2H), 4.65 (s, 2H), 5.34 (s, 1H), 7.40-7.50 (m, 6H), 7.61-7.69 (m, 4H), 11.27 (s, 1H) ppm.
$^{13}$C NMR (500 MHz, CDCl$_3$): δ 14.0, 18.8, 20.7, 26.5, 26.6, 59.7, 127.8, 129.8, 133.0, 135.0 ppm.
HRMS calculated for C$_{20}$H$_{26}$N$_3$OSi [M+H]$^+$ 352.1840 found 352.1843.

Preparative Example 4J

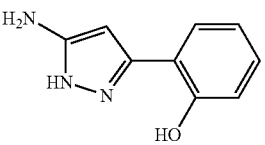 [SMILES: Nc1cc(-c2ccccc2O)n[nH]1]

Prepared from compound from Preparative Example 3B (the TIPS group was cleaved under the reaction conditions).
Colorless wax.
$^1$H NMR (300 MHz, CDCl$_3$): δ 5.17 (s, 1H), 6.89-6.76 (m, 1H), 7.39-7.28 (m, 2H), 7.54-7.42 (m, 2H), 7.65-7.55 (m, 1H), 7.90 (dd, 1H J=7.7, 1.6 Hz), 12.13-11.37 (m, 1H) ppm.

Preparative Example 4K

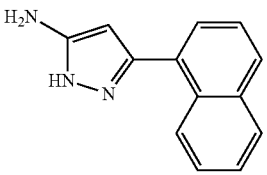 [SMILES: Nc1cc(-c2cccc3ccccc23)n[nH]1]

Prepared from compound from Preparative Example 3C.
White solid.
$^1$H NMR (500 MHz, DMSO-d$_6$): δ 4.83 (s, 2H), 5.71 (s, 1H), 7.56-7.51 (m, 3H), 7.60-7.56 (m, 1H), 7.90 (d, 1H, J=8.0 Hz), 7.95 (dd, 1H, J=6.0, 3.4 Hz), 11.75 (s, 1H) ppm.
$^{13}$C NMR (125 MHz, DMSO-d$_6$): δ 59,7, 125.4, 125.8, 126.2, 126.2, 127.8, 127.8, 128.2, 130.5, 133.5 ppm.
HRMS calculated for C$_{13}$H$_{12}$N$_3$ [M+H]$^+$ 210.1026, found 210.1028.

Preparative Example 4L

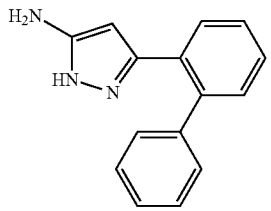 [SMILES: Nc1cc(-c2ccccc2-c2ccccc2)n[nH]1]

Prepared from compound from Preparative Example 2G. Dark brown wax.

$^1$H NMR (500 MHz, DMSO-d$_6$): δ 4.49 (s, 1H), 4.75 (s, 1H), 7.21 (t, 2H, J=7.4 Hz), 7.44-7.25 (m, 6H), 7.58 (s, 1H), 11.42 (s, 1H) ppm.

$^{13}$C NMR (125 MHz, DMSO d$_6$): δ 59.7, 91.0, 126.8, 127.2, 127.5, 127.9, 128.8, 128.9, 130.4, 137.8, 139.9, 141.4, 147.0 ppm.

HRMS calculated for C$_{15}$H$_{14}$N$_3$ [M+H]$^+$ 236.1182, found 236.1184.

Preparative Example 4M

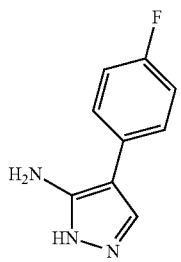 [SMILES: Nc1[nH]ncc1-c1ccc(F)cc1]

Prepared from compound from Preparative Example 1C. Yellow solid.
MP=150-152° C.

$^1$H NMR (500 MHz, DMSO-d$_6$): δ 4.71 (s, 2H), 7.09-7.20 (m, 2H), 7.51 (dd, J=8.7, 5.6 Hz, 2H), 7.63 (s, 1H), 11.68 (bs, 1H) ppm.

$^{13}$C NMR (125 MHz, DMSO-d$_6$): δ 115.1 (d, J=20.9 Hz), 127.2 (d, J=7.4 Hz), 130.5, 159.7 (d, J=241.4 Hz) ppm.

HRMS calculated for C$_9$H$_7$FN$_3$ [M−H]$^-$ 176.0629, found 176.0627.

Preparative Example 4N

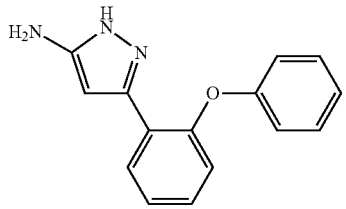 [SMILES: Nc1cc(-c2ccccc2Oc2ccccc2)n[nH]1]

Prepared from compound from Preparative Example 3D.
$^1$H NMR (500 MHz, DMSO-d$_6$): δ 4.66 (s, 2H), 5.78 (s, 1H), 6.88-6.97 (m, 3H), 7.08 (t, J=7.4 Hz, 1H), 7.21 (td, J=7.6, 1.3 Hz, 1H), 7.29 (td, J=7.7, 1.7 Hz, 1H), 7.32-7.39 (m, 2H), 7.86 (s, 1H), 11.69 (s, 1H) ppm.

$^{13}$C NMR (125 MHz, DMSO-d$_6$): δ 117.4, 120.6, 122.7, 124.2, 127.7, 128.6, 129.9, 152.1, 157.1 ppm.

HRMS calculated for C$_{15}$H$_{14}$N$_3$O [M+H]$^+$ 252.1131, found 252.1138.

Preparative Example 4O

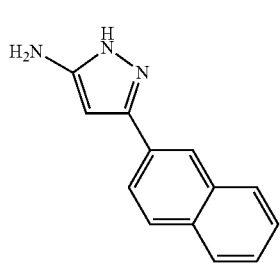 [SMILES: Nc1cc(-c2ccc3ccccc3c2)n[nH]1]

Prepared from compound from Preparative Example 3E.
$^1$H NMR (500 MHz, DMSO-d$_6$): δ 4.83 (d, J=5.3 Hz, 2H), 5.90 (s, 1H), 7.23-7.65 (m, 2H), 7.79-7.94 (m, 4H), 8.15 (d, J=1.3 Hz, 1H), 11.81 (s, 1H) ppm.

$^{13}$C NMR (125 MHz, DMSO-d$_6$): δ 122.8, 123.4, 125.7, 126.3, 127.5, 127.8, 128.0, 132.2, 133.1 ppm.

HRMS calculated for C$_{13}$H$_{12}$N$_3$ [M+H]$^+$ 210.1026, found 210.1031.

Preparative Example 4P

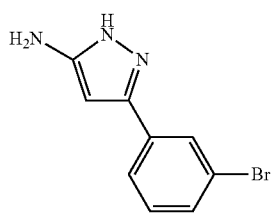 [SMILES: Nc1cc(-c2cccc(Br)c2)n[nH]1]

Prepared from compound from Preparative Example 3F.
$^1$H NMR (500 MHz, DMSO-d$_6$): δ 4.87 (s, 2H), 5.78 (s, 1H), 7.32 (t, J=7.8 Hz, 1H), 7.43 (d, J=8.0 Hz, 1H), 7.65 (d, J=7.7 Hz, 1H), 7.84 (d, J=1.9 Hz, 1H), 11.74 (s, 1H) ppm.

$^{13}$C NMR (125 MHz, DMSO-d$_6$): δ 122.0, 123.7, 127.0, 129.6, 130.7 ppm.

HRMS calculated for C$_9$H$_9$BrN$_3$ [M+H]$^+$ 237.9974, found 237.9979.

Preparative Example 4Q

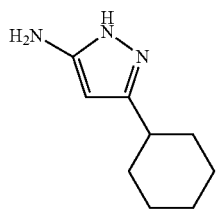 [SMILES: Nc1cc(C2CCCCC2)n[nH]1]

Prepared from compound from Preparative Example 3G.
$^1$H NMR (500 MHz, CDCl$_3$): δ 1.11-1.47 (m, 5H), 1.63-1.85 (m, 3H), 1.86-2.00 (m, 2H), 2.43-2.65 (m, 1H), 5.13 (s, 3H), 5.42 (s, 1H) ppm.

$^{13}$C NMR (125 MHz, CDCl$_3$): δ 26.0, 26.1, 32.7, 35.8, 90.1, 151.2, 154.5 ppm.

HRMS calculated for C$_9$H$_{16}$N$_3$ [M+H]$^+$ 166.1339, found 166.1335.

Preparative Example 4R

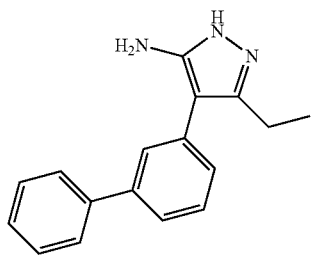 [SMILES: CCc1n[nH]c(N)c1-c1cccc(-c2ccccc2)c1]

Prepared from compound from Preparative Example 3H. Pale yellow wax.

$^1$H NMR (500 MHz, CDCl$_3$): δ 1.24 (t, J=7.6 Hz, 3H), 2.73 (d, J=7.6 Hz, 2H), 5.60 (s, 3H), 7.31-7.39 (m, 2H), 7.43-7.51 (m, 4H), 7.57-7.65 (m, 3H) ppm.

$^{13}$C NMR (126 MHz, CDCl$_3$): δ 13.3, 18.8, 105.9, 125.2, 127.3, 127.5, 127.7, 127.8, 129.4, 133.8, 141.2, 141.9, 143.9, 152.2 ppm.

HRMS calculated for C$_{17}$H$_{18}$N$_3$ [M+H]$^+$ 264.1495, found 264.1496.

Preparative Example 4S

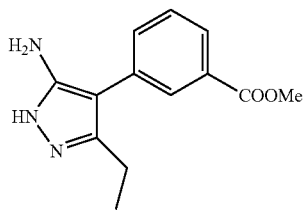 [SMILES: CCc1n[nH]c(N)c1-c1cccc(C(=O)OC)c1]

Prepared from compound from Preparative Example 3I. Colorless wax.

$^1$H NMR (500 MHz, DMSO-d$_6$): δ 1.11 (t, J=7.6 Hz, 3H), 2.56 (q, J=7.6 Hz, 2H), 3.86 (s, 3H), 4.52 (s, 2H), 7.51 (t, J=7.7 Hz, 1H), 7.59 (dt, J=7.7, 1.5 Hz, 1H), 7.77 (dt, J=7.7, 1.5 Hz, 1H), 7.91 (t, J=1.8 Hz, 1H), 11.47 (s, 2H) ppm.

$^{13}$C NMR (126 MHz, DMSO-d$_6$): δ 13.2, 30.6, 52.1, 125.7, 128.5, 128.9, 129.9, 132.7, 134.7, 166.4 ppm.

Preparative Example 4T

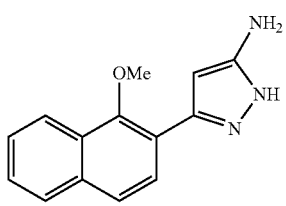 [SMILES: COc1c(-c2cc(N)[nH]n2)ccc2ccccc12]

Prepared from compound from Preparative Example 2H. Colorless wax.

$^1$H NMR (500 MHz, DMSO-d$_6$): δ 3.79 (s, 3H), 4.82 (s, 2H), 6.05 (s, 1H), 7.54-7.48 (m, 1H), 7.60-7.54 (m, 1H), 7.70 (d, J=8.7 Hz, 1H), 7.91 (d, J=7.9 Hz, 2H), 8.10 (d, J=8.3 Hz, 1H), 11.76 (s, 1H) ppm.

$^{13}$C NMR (126 MHz, DMSO-d$_6$): δ 60.9, 122.0, 125.3, 123.9, 126.2, 126.4, 127.8, 128.0, 133.7, 151.8 ppm.

HRMS calculated for C$_{14}$H$_{14}$N$_3$O [M+H]$^+$ 240.1131, found 240.1137.

Preparative Example 4U

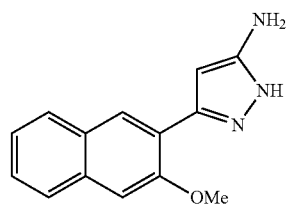 [SMILES: COc1cc2ccccc2cc1-c1cc(N)[nH]n1]

Prepared from compound from Preparative Example 2I. Colorless wax.

$^1$H NMR (500 MHz, DMSO-d$_6$): δ 3.97 (s, 3H), 4.63 (s, 2H), 5.99 (s, 1H), 7.38-7.32 (m, 1H), 7.41 (s, 1H), 7.47-7.41 (m, 1H), 7.81 (t, J=8.6 Hz, 2H), 8.16 (s, 1H), 11.71 (s, 1H) ppm.

$^{13}$C NMR (126 MHz, DMSO-d$_6$): δ 55.5, 91.7, 106.1, 123.9, 126.3, 127.5, 128.1, 133.3, 154.4, 154.4 ppm.

HRMS calculated for C$_{14}$H$_{14}$N$_3$O [M+H]$^+$ 240.1131, found 240.1137.

Preparative Example 4V

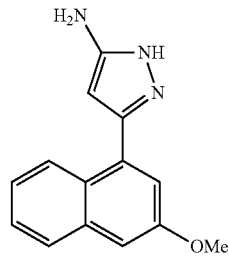 [SMILES: COc1cc(-c2cc(N)[nH]n2)c2ccccc2c1]

Prepared from compound from Preparative Example 2J.

$^1$H NMR (500 MHz, DMSO-d$_6$): δ 3.84 (s, 3H) 4.61 (s, 2H), 5.51 (s, 1H), 7.35 (t, J=7.4 Hz, 1H), 7.44-7.39 (m, 1H), 7.49 (d, J=9.1 Hz, 1H), 7.70 (d, J=8.3 Hz, 1H), 7.88 (d, J=8.0 Hz, 1H), 7.98 (d, J=9.0 Hz, 1H), 11.50 (s, 1H) ppm.

$^{13}$C NMR (126 MHz, DMSO-d$_6$): δ 56.3, 114.0, 123.5, 123.7, 124.6, 124.7, 126.5, 127.8, 127,9, 127.9, 128.3, 129.9, 133.3, 154.8 ppm.

HRMS calculated for C$_{14}$H$_{14}$N$_3$O [M+H]$^+$ 240.1131, found 240.1129.

Preparative Example 4W

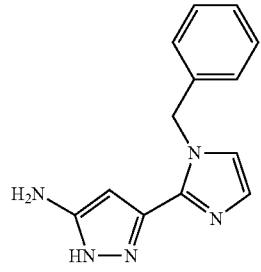 [SMILES: Nc1cc(-c2nccn2Cc2ccccc2)n[nH]1]

Prepared from compound from Preparative Example 2K.

$^1$H NMR (500 MHz, DMSO-d$_6$): δ 5.19 (s, J=71.3 Hz, 1H), 5.66 (s, J=109.4 Hz, 2H), 6.93 (d, J=8.8 Hz, 1H), 7.19-7.13 (m, 4H), 7.32-7.27 (m, 3H), 7.76 (s, J=19.5 Hz, 1H), 11.67 (s, 2H) ppm.

$^{13}$C NMR (126 MHz, DMSO-d$_6$): δ 49.4, 113.3, 119.6, 127.0, 127.2, 127.4, 127.7, 128.4, 128.5, 128.6, 137.3 ppm.

HRMS calculated for C$_{13}$H$_{14}$N$_5$ [M+H]$^+$ 240.1244, found 240.1250.

Preparative Example 5A

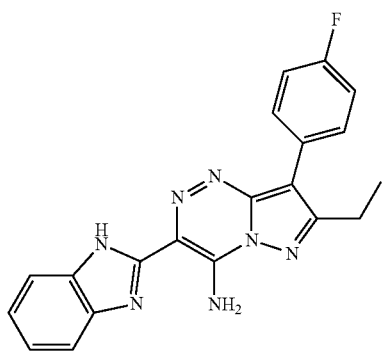

Compound from Preparative Example 4A (0.4 g, 1.95 mmol) was dissolved in EtOH (10 mL) and H$_2$O (10 mL) and 35% aqueous HCl (0.7 mL, 7.8 mmol) was added. The solution was cooled to −10° C. and a pre-cooled (−5° C.) solution of NaNO$_2$ (0.3 g, 3.9 mmol) in EtOH (5 mL) and H$_2$O (5 mL) was added. The reaction mixture was stirred for 20 min., then a pre-cooled solution (−5° C.) of KOAc (1.2 g, 11.7 mmol) plus 2-(cyanomethyl)-benzimidazole (0.36 g, 2.3 mmol) in EtOH (10 mL) and H$_2$O (10 mL) was added. The resulting mixture was stirred at 25° C. for 3 hrs. The precipitate was filtered and washed on filter with water (25 mL). The product was dried in a vacuum to yield a green solid, which was used directly for the next step without additional purification.

The solid was dissolved in anhydrous DMF (10 mL) and the mixture was refluxed under N$_2$ for 3 hrs. The solution was poured into water (100 mL), the precipitate was collected by filtration, dissolved in dioxane (10 mL) at 50° C., and the solution was poured into water (100 mL). The precipitate was collected by filtration, washed on filter with water (10 mL), then with Et$_2$O (15 mL) and dried in a vacuum to yield the product as a yellow solid (200 mg, 70%).

MP>250° C.

$^1$H NMR (500 MHz, DMSO-d$_6$): δ 1.35 (t, 3H, J=7.6 Hz), 3.05 (q, 2H, J=7.6 Hz), 7.30-7.21 (m, 2H), 7.40-7.32 (m, 2H), 7.56 (d, 1H, J=7.5 Hz), 7.75 (d, 1H, J=7.6 Hz), 7.90-7.83 (m, 2H), 9.34 (s, 1H), 9.95 (s, 1H), 13.35 (s, 1H) ppm.

$^{13}$C NMR (125 MHz, DMSO-d$_6$): δ 13.1, 20.9, 107.3, 111.5, 115.5 (d, J=21.5 Hz), 118.3, 119.2, 121.9, 122.9, 127.7, 130.9 (d, J=8.1 Hz), 133.7, 138.7, 142.7, 146.3, 150.1, 158.1, 161.1 (d, J=244.2 Hz) ppm.

HRMS calculated for C$_{20}$H$_{17}$FN$_7$ [M+H]$^+$ 374.1524, found 374.1529.

Preparative Examples 5B-5O

By essentially same procedure set forth in Preparative Example 5A, compounds given below were prepared from the indicated aminopyrazoles.

Preparative Example 5B

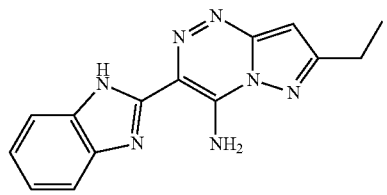 [SMILES: CCc1cc2nnc(-c3nc4ccccc4[nH]3)c(N)n2n1]

Prepared from compound from Preparative Example 4B.

Orange solid.

MP=136.0-137.5° C.

$^1$H NMR (500 MHz, DMSO-d$_6$): δ 1.36 (t, 3H, J=7.59 Hz), 2.90 (q, 2H, J=7.64 Hz), 6.88 (s, 1H), 7.21-7.27 (m, 2H, J=6.79 Hz), 7.53 (d, 1H, J 6.95 Hz), 7.73 (d, 1H, J=7.76 Hz), 9.29 (s, 1H), 9.89 (s, 1H), 13.40 (s, 1H) ppm.

$^{13}$C NMR (125 MHz, DMSO-d$_6$): δ 13.4, 21.7, 94.5, 111.4, 118.2, 118.3, 121.8, 122.8, 133.7, 138.7, 142.6, 149.6, 150.2, 161.6 ppm.

HRMS calculated for C$_{14}$H$_{12}$N$_7$ [M+H]$^-$ 278.1160, found 278.1159.

Preparative Example 5C

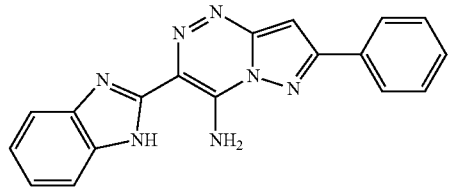 [SMILES: Nc1c(-c2nc3ccccc3[nH]2)nnc2cc(-c3ccccc3)nn12]

Prepared from compound from Preparative Example 4C.

Slightly green solid.

MP>250° C.

$^1$H NMR (500 MHz, DMSO-d$_6$): δ 7.26 (s, 2H), 7.50 (t, 1H, J=7.3 Hz), 7.62-7.54 (m, 4H), 7.75 (s, 1H), 8.19 (d, 2H, J=7.4 Hz), 9.34 (s, 1H), 9.95 (s, 1H), 13.46 (s, 1H) ppm.

$^{13}$C NMR (125 MHz, DMSO-d$_6$): δ 93.4, 111.5, 118.3, 118.9, 121.8, 122.9, 126.6, 128.9, 129.6, 138.8, 150.0, 150.3, 156.3 ppm.

HRMS calculated for C$_{18}$H$_{14}$N$_7$ [M+H]$^+$ 328.1305, found 328.1306.

Preparative Example 5D

Prepared from compound from Preparative Example 4D.
Green-brown solid.
MP>250° C.
$^1$H NMR (500 MHz, DMSO-d$_6$): δ 1.40 (d, 6H, J=6.9 Hz), 3.45 (hept, 1H, J=6.9 Hz), 7.30-7.21 (m, 2H), 7.41-7.34 (m, 2H), 7.56 (d, 1H, J=7.0 Hz), 7.83-7.71 (m, 3H), 9.20 (s, 1H), 9.94 (s, 1H), 13.35 (s, 1H) ppm.
$^{13}$C NMR (125 MHz, DMSO-d$_6$): δ 22.3, 26.3, 107.0, 111.5, 115.5 (d, J=21.5 Hz), 118.3, 119.1, 121.8, 122.9, 127.6, 131.4 (d, J=7.9 Hz), 133.7, 138.7, 148.2 (d, J=465.7 Hz), 160.2, 160.2, 161.9, 162.1 ppm.
HRMS calculated for C$_{21}$H$_{19}$FN$_7$ [M+H]$^+$ 386.1535, found 386.1541.

Preparative Example 5E

Prepared from compound from Preparative Example 4E.
Orange solid.
MP>250° C.
$^1$H NMR (500 MHz, DMSO-d$_6$): δ 1.39 (d, 6H, J=6.9 Hz), 3.22 (hept, 1H, J=13.9, 7.0 Hz), 6.91 (s, 1H), 7.32-7.17 (m, 2H), 7.53 (d, 1H, J=7.2 Hz), 7.73 (d, 1H, J=7.6 Hz), 9.22 (s, 1H), 9.88 (s, 1H), 13.40 (s, 1H) ppm.
$^{13}$C NMR (125 MHz, DMSO-d$_6$): δ 22.4, 28.2, 93.2, 111.4, 118.2, 118.3, 121.8, 122.8, 133.7, 138.7, 142.7, 149.6, 150.2, 165.9 ppm.
HRMS calculated for C$_{15}$H$_{15}$N$_7$ [M+H]$^+$ 294.1462, found 294.1450.

Preparative Example 5F

Prepared from compound from Preparative Example 4F.
Yellow solid.
MP>250° C.
$^1$H NMR (500 MHz, DMSO-d$_6$): δ 1.45 (s, 9H), 6.95 (s, 1H), 7.30-7.18 (m, 2H), 7.53 (d, 1H, J=7.2 Hz), 7.74 (d, 1H, J=7.6 Hz), 9.05 (s, 1H), 9.85 (s, 1H), 13.39 (s, 1H) ppm.
$^{13}$C NMR (125 MHz, DMSO-d$_6$): δ 30.1, 33.7, 93.0, 111.4, 118.2, 118.2, 121.7, 122.8, 133.7, 138.7, 142.7, 149.5, 150.2, 168.6 ppm.
HRMS calculated for C$_{16}$H$_{16}$N$_7$ [M+H]$^-$ 306.1473, found 306.1478.

Preparative Example 5G

Prepared from compound from Preparative Example 4G.
Orange solid.
MP>250° C.
$^1$H NMR (500 MHz, DMSO-d$_6$): δ 7.26 (s, 2H), 7.46 (s, 1H), 7.59-7.52 (m, 3H), 7.71-7.64 (m, 1H), 7.76 (s, 1H), 8.07-7.99 (m, 1H), 9.50 (s, 1H), 10.01 (s, 1H), 13.50 (s, 1H) ppm.
$^{13}$C NMR (125 MHz, DMSO-d$_6$): δ 66.3, 97.2, 111.5, 118.3, 119.1, 121.9, 122.9, 127.4, 130.4, 130.9, 131.5, 132.0, 138.9, 142.6, 149.5, 149.9, 154.1 ppm.
HRMS calculated for C$_7$H$_{14}$N$_3$ [M+H]$^+$ 140.1182, found 140.1191.

Preparative Example 5H

Prepared from compound from Preparative Example 4H.
Yellow solid.
MP>250° C.
$^1$H NMR (500 MHz, DMSO-d$_6$): δ 3.99 (s, 3H), 7.14 (td, 1H, J=7.6, 0.9 Hz), 7.30-7.21 (m, 3H), 7.52-7.46 (m, 2H), 7.55 (d, 1H, J=7.4 Hz), 7.76 (d, 1H, J=7.6 Hz), 8.28 (dd, 1H, J=7.7, 1.8 Hz), 9.32 (s, 1H), 9.92 (s, 1H), 13.45 (s, 1H) ppm;

$^{13}$C NMR (125 MHz, DMSO-d$_6$): δ 55.6, 97.3, 111.5, 112.2, 118.3, 118.7, 120.0, 120.5, 121.8, 122.9, 128.9, 131.0, 133.7, 138.6, 142.7, 149.8, 150.1, 153.3, 157.4 ppm.

HRMS calculated for C$_{19}$H$_{16}$N$_7$O [M+H]$^+$ 358.1411, found 358.1412.

Preparative Example 5I

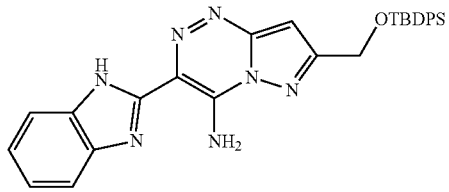

Prepared from compound from Preparative Example 4I.

The product was additionally purified by column chromatography on silica gel (CH$_2$Cl$_2$/MeOH—10:1).

Orange solid.

MP=233.5-234.0° C.

$^1$H NMR (500 MHz, DMSO-d$_6$): δ 1.07 (s, 9H), 5.02 (s, 2H), 6.97 (s, 1H), 7.29-7.19 (m, 2H), 7.49-7.43 (m, 6H), 7.54 (d, 1H, J=7.7 Hz), 7.70 (d, 4H, J=7.2 Hz), 7.74 (d, 1H. J=7.7 Hz), 9.34 (s, 1H), 9.94 (s, 1H), 13.45 (s, 1H) ppm.

$^{13}$C NMR (125 MHz, DMSO-d$_6$): δ 18.8, 26.6, 60.3, 94.5, 111.4, 118.3, 118.8, 121.8, 127.4, 128.0, 130.0, 132.5, 134.4, 135.0, 138.9, 149.5, 150.0, 158.8 ppm.

HRMS calculated for C$_{29}$H$_3$ON$_7$OSi [M+H]$^+$ 520.2276, found 520.2273.

Preparative Example 5J

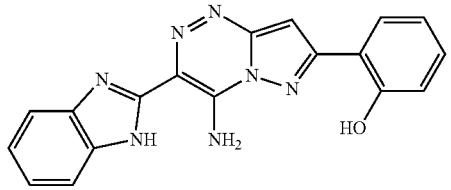 [SMILES: Nc1c(-c2nc3ccccc3[nH]2)nnc2cc(-c3ccccc3O)nn12]

Prepared from compound from Preparative Example 4J.

Orange solid.

MP>250° C.

$^1$H NMR (500 MHz, DMSO-d$_6$): δ 7.03-6.98 (m, 1H), 7.08-7.04 (m, 1H), 7.30-7.22 (m, 2H), 7.37-7.32 (m, 1H), 7.58-7.55 (m, 2H), 7.76 (d, 1H, J=7.5 Hz), 8.14 (dd, 1H, J=7.8, 1.6 Hz), 9.64 (s, 1H), 9.98 (s, 1H), 10.31 (s, 1H), 13.46 (s, 1H) ppm.

$^{13}$C NMR (125 MHz, DMSO-d$_6$): δ 94.7, 111.5, 116.6, 117.1, 118.3, 119.1, 119.4, 121.8, 122.9, 128.6, 130.9, 133.7, 138.6, 142.7, 149.4, 150.0, 155.0, 155.9 ppm.

HRMS calculated for C$_{13}$H$_{10}$N$_7$O [M+H]$^+$ 280.0941, found 280.0945.

Preparative Example 5K

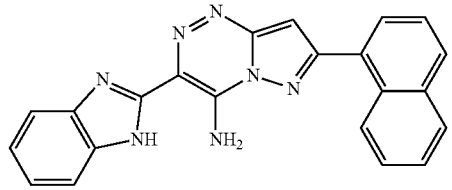 [SMILES: Nc1c(-c2nc3ccccc3[nH]2)nnc2cc(-c3cccc4ccccc34)nn12]

Prepared from compound from Preparative Example 4K.

Red solid.

MP>250° C.

$^1$H NMR (500 MHz, DMSO-d$_6$): δ 7.44 (s, 2H), 7.58 (s, 1H), 7.65-7.61 (m, 2H), 7.71-7.66 (m, 2H), 7.76 (s, 1H), 7.97 (dd, 1H, J=7.1, 1.1), 8.08-8.04 (m, 1H), 8.10 (d, 1H, J=8.2), 8.71-8.64 (m, 1H), 9.52 (s, 1H), 10.03 (s, 1H), 13.51 (s, 1H) ppm.

$^{13}$C NMR (125 MHz, DMSO-d$_6$): δ 97.2, 111.5, 114.1, 118.3, 119.0, 121.8, 122.9, 125.4, 125.8, 126.2, 127.0, 128.4, 128.4, 129.6, 129.8, 130.6, 133.4, 139.0, 142.7, 149.5, 150.1, 156.8 ppm.

HRMS calculated for C$_{22}$H$_{16}$N$_7$ [M+H]$^+$ 378.1462, found 378.1459.

Preparative Example 5L

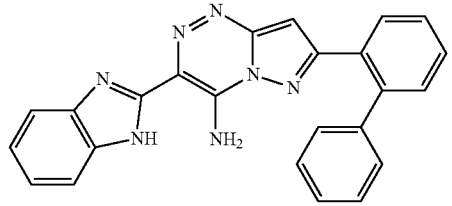 [SMILES: Nc1c(-c2nc3ccccc3[nH]2)nnc2cc(-c3ccccc3-c3ccccc3)nn12]

Prepared from compound from Preparative Example 4L.

Beige solid.

MP>250° C.

$^1$H NMR (500 MHz, DMSO-d$_6$): δ 6.11 (s, 1H), 7.25 (d, 2H, J=4.5 Hz), 7.33-7.28 (m, 2H), 7.43-7.35 (m, 3H), 7.49-7.44 (m, 1H), 7.63-7.50 (m, 3H), 7.74 (s, 1H), 8.07-8.00 (m, 1H), 9.41 (s, 1H), 9.97 (s, 1H), 13.43 (s, 1H) ppm.

$^{13}$C NMR (500 MHz, DMSO-d$_6$): δ 96.7, 109.5, 111.4, 118.3, 118.7, 121.8, 122.9, 127.4, 127.6, 128.3, 129.2, 129.3, 130.0, 130.5, 130.6, 138.7, 140.6, 141.3, 142.6, 149.0, 149.9, 156.7 ppm.

HRMS calculated for C$_{24}$H$_{18}$N$_7$ [M+H]$^+$ 404.1618, found 404.1615.

Preparative Example 5M

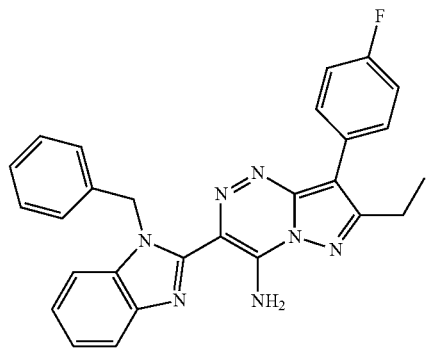 [SMILES: CCc1nn2c(N)c(-c3nc4ccccc4n3Cc3ccccc3)nnc2c1-c1ccc(F)cc1]

Prepared from compounds from Preparative Example 4A and Preparative Example D.

The product was additionally purified by column chromatography on silica gel (hexane/EtOAc—1:1).

Yellow solid.

MP>250° C.

$^1$H NMR (500 MHz, DMSO-d$_6$): δ 1.34 (t, 3H, J=7.5 Hz) 3.05 (q, 2H, J=7.5 Hz), 6.30 (s, 2H), 7.20 (d, 3H, J=7.3 Hz), 7.27-7.23 (m, 2H), 7.32-7.28 (m, 2H), 7.36-7.31 (m, 2H), 7.61-7.55 (m, 1H), 7.86-7.78 (m, 3H), 9.37 (s, 1H), 10.37 (s, 1H) ppm.

$^{13}$C NMR (125 MHz, DMSO-d$_6$): δ 13.1, 20.8, 48.9, 107.1, 110.8, 115.4 (d, J=21.4 Hz), 118.6, 120.5, 122.7, 122.9 (d, J=67.5 Hz), 126.6, 127.1, 127.5, 128.4, 130.8 (d, J=8.1 Hz), 135.3, 137.6, 139.5, 141.1, 145.5, 148.0, 158.0, 161.0 (d, J=244.1 Hz) ppm.

HRMS calculated for C$_{27}$H$_{23}$N$_7$F [M+H]$^+$ 464.1993, found 464.1997.

Preparative Example 5N

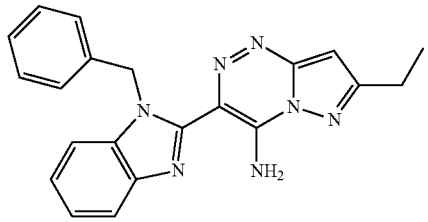 [SMILES: CCc1cc2nnc(-c3nc4ccccc4n3Cc3ccccc3)c(N)n2n1]

Prepared from compounds from Preparative Example 4B and Preparative Example D.

The product was additionally purified by column flash chromatography on silica gel (EtOAc/MeOH—10:1).

Brown solid.

MP=219.8-220.7° C.

$^1$H NMR (500 MHz, DMSO-d$_6$): δ 1.35 (t, 3H, J=7.6 Hz), 2.89 (q, 2H, J=7.6 Hz), 6.27 (s, 2H), 6.82 (s, 1H), 7.17-7.22 (m, 3H), 7.23-7.28 (m, 2H), 7.28-7.33 (m, 2H), 7.56-7.67 (m, 1H), 7.85-7.76 (m, 1H), 9.29 (s, 1H), 10.26 (s, 1H) ppm.

$^{13}$C NMR (125 MHz, DMSO-d$_6$): δ 13.4, 21.7, 48.9, 94.4, 110.7, 118.6, 119.6, 122.6, 123.2, 126.7, 127.1, 128.4, 135.4, 137.6, 139.5, 141.0, 148.1, 148.8, 161.7 ppm.

HRMS calculated for C$_{21}$H$_{20}$N$_7$ [M+H]$^+$ 370.1775, found 370.1776.

Preparative Example 5O

Prepared from 3-aminopyrazole.

Brown-orange solid.

MP>250° C. (dec.).

$^1$H NMR (500 MHz, DMSO-d$_6$): δ 7.06 (d, J=2.4 Hz, 1H), 7.13-7.39 (m, 2H), 7.54 (d, J=6.8 Hz, 1H), 7.75 (d, J=6.6 Hz, 1H), 8.42 (d, J=2.4 Hz, 1H), 9.46 (s, 1H), 9.96 (s, 1H), 13.45 (s, 1H) ppm.

$^{13}$C NMR (125 MHz, DMSO-d$_6$): δ 96.7, 111.4, 118.3, 118.4, 121.8, 122.9, 133.7, 139.2, 142.7, 146.1, 149.1, 150.1 ppm.

HRMS calculated for C$_{12}$H$_8$N$_7$ [M−H]$^-$ 250.0846, found 250.0844.

Preparative Example 5P

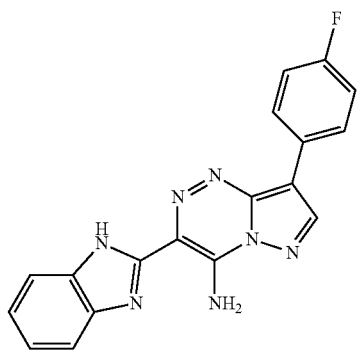 [SMILES: Nc1c(-c2nc3ccccc3[nH]2)nnc2c(-c3ccc(F)cc3)cnn12]

Compound from Preparative Example 4M (0.22 g, 1.25 mmol) was dissolved in EtOH (3 mL) and H$_2$O (3 mL) and 35% aqueous HCl (0.44 mL, 5.0 mmol) was added. The solution was cooled to −10° C. and a pre-cooled (−5° C.) solution of NaNO$_2$ (0.17 g, 2.5 mmol) in EtOH (2 mL) and H$_2$O (2 mL) was added. The reaction mixture was stirred for 20 min, then a pre-cooled solution (−5° C.) of KOAc (0.74 g, 7.52 mmol) plus 2-(cyanomethyl)benzimidazole (0.24 g, 1.5 mmol) in EtOH (3 mL) and H$_2$O (3 mL) was added. The resulting mixture was allowed to warm to 25° C. and was stirred for 3 hrs. The precipitated solid was filtered and washed on filter with cold water (20 mL). The product was dried in a vacuum to yield a yellow-grey solid, which was used directly for the next step without additional purification.

The solid was dissolved in anhydrous DMF (3 mL) and the mixture was refluxed under N$_2$ for 2 hrs. The solvent was evaporated. The residue was mixed with EtOAc (50 mL), washed with water (2×50 mL) and then with brine (2×50 mL). The organic phase was dried over MgSO$_4$, filtered, and the solvent was evaporated. To the residue were added CH$_2$Cl$_2$ (5 mL) and diethyl ether (10 mL) and after trituration the precipitate was filtered and rinsed with cold diethyl ether (20 mL). The solid was dried in a vacuum to give the product as a yellow solid (235 mg, 54%).

MP>350° C. (dec.).

$^1$H NMR (500 MHz, DMSO-d$_6$): δ 7.26 (s, 2H), 7.34 (t, J=8.9 Hz, 2H), 7.59 (s, 1H), 7.75 (s, 1H), 8.37 (dd, J=8.8, 5.5 Hz, 2H), 8.95 (s, 1H), 9.59 (s, 1H), 10.04 (s, 1H), 13.45 (s, 1H) ppm.

$^{13}$C NMR (125 MHz, DMSO—d$_6$): δ 108.9, 115.7 (d, J=21.6 Hz), 119.3, 127.9 (d, J=7.6 Hz), 139.4, 143.6, 145.0, 149.9, 160.9 (d, J=244.7 Hz) ppm.

HRMS calculated for C$_{18}$H$_{11}$FN$_7$ [M+H]$^+$ 344.1065, found 344.1069.

Preparative Examples 5Q-5Za

By essentially same procedure set forth in Preparative Example 5A, compounds given below were prepared from the indicated aminopyrazoles.

Preparative Example 5Q

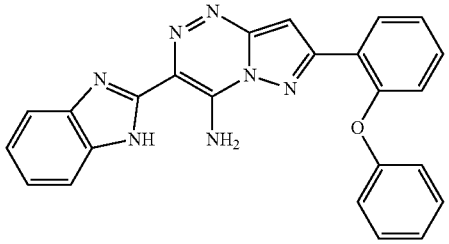 [SMILES: Nc1c(-c2nc3ccccc3[nH]2)nnc2cc(-c3ccccc3Oc3ccccc3)nn12]

Prepared from compound from Preparative Example 4N.
¹HNMR (500 MHz, DMSO-d₆): δ 6.93-7.19 (m, 4H), 7.19-7.34 (m, 3H), 7.40 (s, 3H), 7.53 (s, 2H), 7.75 (d, J=7.5 Hz, 1H), 8.39 (d, J=7.8 Hz, 1H), 9.37 (s, 1H), 9.96 (s, 1H), 13.46 (s, 1H) ppm.
¹³C NMR (125 MHz, DMSO-d₆): δ 96.6, 111.5, 117.5, 118.3, 118.9, 120.7, 121.8, 122.9, 123.2, 123.8, 124.4, 129.6, 130.1, 131.2, 133.7, 138.7, 142.7, 149.8, 150.0, 152.3, 153.8, 156.8 ppm.
HRMS calculated for $C_{24}H_{18}N_7O$ [M+H]⁺ 420.1567, found 420.1565.

Preparative Example 5R

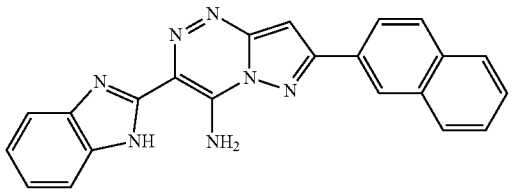 [SMILES: Nc1c(-c2nc3ccccc3[nH]2)nnc2cc(-c3ccc4ccccc4c3)nn12]

Prepared from compound from Preparative Example 4O.
NMR (500 MHz, DMSO-d₆): δ7.26 (p, J=7.4 Hz, 2H), 7.51-7.64 (m, 3H), 7.68 (s, 1H), 7.77 (d, J=7.6 Hz, 1H), 8.00 (d, J=6.4 Hz, 1H), 8.05 (d, J=6.5 Hz, 1H), 8.10 (d, J=8.6 Hz, 1H), 8.34 (d, J=8.4 Hz, 1H), 8.75 (s, 1H), 9.40 (s, 1H), 9.99 (s, 1H), 13.47 (s, 1H) ppm.
¹³C NMR (125 MHz, DMSO-d₆): δ 93.7, 111.5, 118.3, 119.0, 121.8, 122.9, 124.2, 125.9, 126.8, 126.9, 127.7, 128.3, 128.5, 129.2, 132.9, 133.4, 133.7, 138.8, 142.7, 150.0, 150.3, 156.2 ppm.
HRMS calculated for $C_{22}H_{16}N_7$ [M+H]⁺ 378.1462, found 378.1449.

Preparative Example 5S

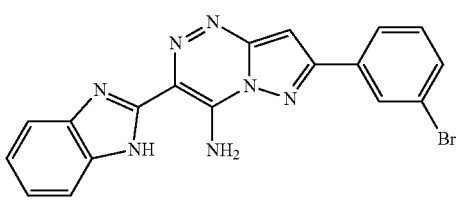 [SMILES: Nc1c(-c2nc3ccccc3[nH]2)nnc2cc(-c3cccc(Br)c3)nn12]

Prepared from compound from Preparative Example 4P.
¹H NMR (500 MHz, DMSO-d₆): δ 7.15-7.36 (m, 2H), 7.48-7.60 (m, 2H), 7.63 (s, 1H), 7.65-7.72 (m, 1H), 7.76 (s, 1H), 8.18 (d, J=7.8 Hz, 1H), 8.42 (t, J=1.7 Hz, 1H), 9.42 (s, 1H), 9.97 (s, 1H), 13.47 (s, 1H) ppm.
¹³C NMR (125 MHz, DMSO-d₆): δ 93.8, 111.5, 118.3, 119.2, 121.9, 122.3, 122.9, 125.6, 128.9, 131.1, 132.3, 133.7, 134.1, 138.8, 142.7, 149.9, 150.3, 154.6 ppm.
HRMS calculated for $C_{18}H_{13}BrN_7$ [M+H]⁺ 406.0410, found 406.0412.

Preparative Example 5T

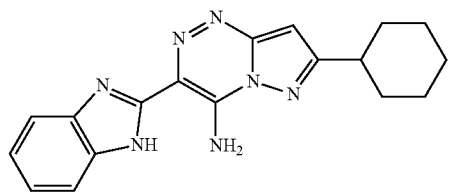 [SMILES: Nc1c(-c2nc3ccccc3[nH]2)nnc2cc(C3CCCCC3)nn12]

Prepared from compound from Preparative Example 4Q.
¹H NMR (500 MHz, DMSO-d₆): δ 1.25-1.36 (m, 1H), 1.36-1.50 (m, 2H), 1.60 (qd, J=12.5, 3.4 Hz, 2H), 1.69-1.77 (m, 1H), 1.78-1.89 (m, 2H), 2.06 (d, J=10.6 Hz, 2H), 2.89 (t, J=11.6 Hz, 1H), 6.88 (s, 1H), 7.23 (dt, J=15.2, 6.8 Hz, 2H), 7.53 (d, J=7.9 Hz, 1H), 7.73 (d, J=7.6 Hz, 1H), 9.19 (s, 1H), 9.87 (s, 1H), 13.40 (s, 1H) ppm.
¹³C NMR (125 MHz, DMSO-d₆): δ 25.5, 25.7, 32.4, 37.7, 93.5, 111.4, 118.2, 121.8, 122.8, 133.7, 138.7, 142.7, 149.5, 150.2, 164.8 ppm.
HRMS calcd for $C_{18}H_{20}N_7$ [M+H]⁺ 334.1775, found 334.1765.

Preparative Example 5U

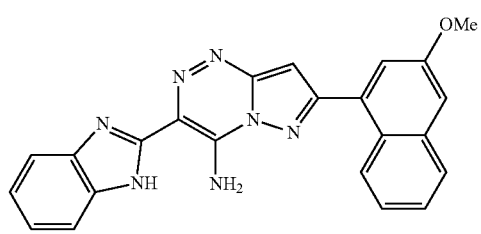 [SMILES: COc1cc(-c2cc3nnc(-c4nc5ccccc5[nH]4)c(N)n3n2)c2ccccc2c1]

Prepared from compound from Preparative Example 4V.
¹H NMR (500 MHz, DMSO-d₆): δ 3.89 (s, 1H), 7.17 (s, 1H), 7.31-7.22 (m, 1H), 7.46-7.37 (m, 1H), 7.57 (d, J=6.4 Hz, 1H), 7.62 (d, J=9.2 Hz, 1H), 7.68-7.63 (m, 1H), 7.76 (d, J=6.5 Hz, 1H), 7.99-7.93 (m, 2H), 8.14 (d, J=9.1 Hz, 2H), 9.51 (s, 1H), 9.99 (s, 1H), 13.50 (s, 3H) ppm.
¹³C NMR (126 MHz, DMSO-d₆): δ 56.4, 99.0, 111.4, 113.7, 115.3, 117.9, 118.3, 118.6, 121.8, 122.9, 123.7, 124.7, 127.0, 127.9, 128.2, 131.0, 133.0, 138.9, 149.5, 150.2, 153.4, 155.1 ppm.
HRMS calculated for $C_{23}H_{18}N_7O$ [M+H]⁺ 408.1567, found 408.1569.

Preparative Example 5V

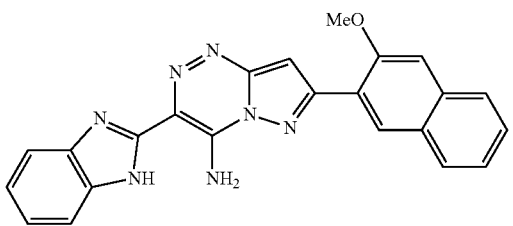 [SMILES: COc1cc2ccccc2cc1-c1cc2nnc(-c3nc4ccccc4[nH]3)c(N)n2n1]

Prepared from compound from Preparative Example 4U.
$^1$H NMR (500 MHz, DMSO-$d_6$): δ 4.09 (s, 3H), 7.27 (s, 2H), 7.44 (t, J=7.1 Hz, 1H), 7.66-7.49 (m, 4H), 7.76 (s, 1H), 8.02-7.86 (m, 2H), 8.77 (s, 1H), 9.43 (s, 1H), 9.97 (s, 1H), 13.48 (s, 1H) ppm.
$^{13}$C NMR (126 MHz, DMSO-$d_6$): δ 55.8, 66.3, 97.9, 106.7, 118.8, 121.9, 124.3, 126.5, 127.3, 127.9, 127.9, 128.8, 134.6, 138.7, 149.8, 150.1, 153.2, 155.2 ppm.
HRMS calculated for $C_{23}H_{18}N_7O$ [M+H]$^+$ 408.1567, found 408.1567.

Preparative Example 5W

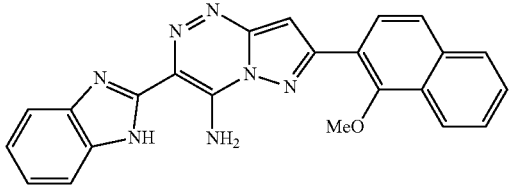 [SMILES: COc1c(-c2cc3nnc(-c4nc5ccccc5[nH]4)c(N)n3n2)ccc2ccccc12]

Prepared from compound from Preparative Example 4T.
$^1$H NMR (500 MHz, DMSO-$d_6$): δ 3.96 (s, 3H), 7.26 (s, 2H), 7.57 (s, 1H), 7.61 (s, 1H), 7.69-7.62 (m, 2H), 7.76 (s, 1H), 7.89 (t, J=9.7 Hz, 1H), 8.02 (d, J=7.6 Hz, 1H), 8.24 (d, J=8.0 Hz, 1H), 8.43 (d, J=8.6 Hz, 1H), 9.42 (s, 1H), 9.99 (s, J=46.1 Hz, 1H), 13.50 (s, 1H) ppm.
$^{13}$C NMR (126 MHz, DMSO-$d_6$): δ 61.8, 66.3, 96.5, 96.6, 111.5, 118.3, 118.9, 120.3, 122.3, 122.5, 124.1, 125.8, 126.0, 126.7, 127.3, 127.9, 135.0, 138.7, 150.1, 150.2, 153.0, 154.8 ppm.
HRMS calculated for $C_{23}H_{18}N_7O$ [M+H]$^+$ 408.1567, found 408.1568.

Preparative Example 5X

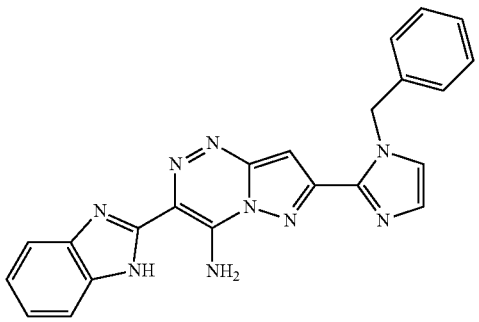 [SMILES: Nc1c(-c2nc3ccccc3[nH]2)nnc2cc(-c3nccn3Cc3ccccc3)nn12]

Prepared from compound from Preparative Example 4W.
$^1$H NMR (500 MHz, DMSO-$d_6$): δ 6.04 (s, 2H), 7.16 (s, 1H), 7.30-7.18 (m, 8H), 7.48 (s, 1H), 7.55 (d, J=7.4 Hz, 1H), 7.75 (d, J=7.7 Hz, 1H), 9.44 (s, 1H), 9.99 (s, 1H), 13.47 (s, 1H) ppm.
$^{13}$C NMR (126 MHz, DMSO-$d_6$): δ 60.2, 105.1, 121.5, 128.3, 129.2, 131.8, 132.9, 134.1, 137.4, 137.5, 138.5, 139.2, 143.8, 148.1, 148.8, 148.8, 152.7, 159.0, 159.5, 159.9 ppm.
HRMS calculated for $C_{22}H_{18}N_9$ [M+H]$^+$ 408.1680, found 408.1684.

Preparative Example 5Y

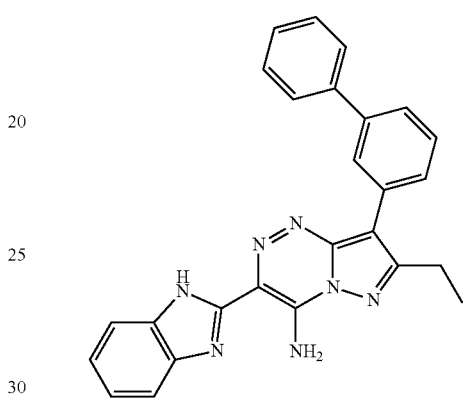

Prepared from compound from Preparative Example 4R.
$^1$H NMR (500 MHz, DMSO-$d_6$): δ 1.40 (t, J=7.6 Hz, 3H), 3.14 (q, J=7.5 Hz, 2H), 7.18-7.32 (m, 2H), 7.35-7.45 (m, 1H), 7.49-7.58 (m, 3H), 7.60-7.70 (m, 2H), 7.75 (dt, J=8.1, 2.1 Hz, 3H), 7.79-7.85 (m, 1H), 8.23 (t, J=1.8 Hz, 1H), 9.37 (s, 1H), 9.97 (s, 1H), 13.43 (s, 1H) ppm.
$^{13}$C NMR (126 MHz, DMSO-$d_6$): δ 13.1, 21.1, 107.9, 111.5, 118.3, 119.3, 121.8, 122.9, 125.0, 126.7, 127.4, 127.5, 127.6, 129.0, 129.2, 132.0, 133.7, 138.7, 140.2, 140.4, 142.7, 146.5, 150.1, 158.1 ppm.
HRMS calcd for $C_{26}H_{23}N_7$ [M+H]$^+$ 432.1931, found 432.1929.

Preparative Example 5Z

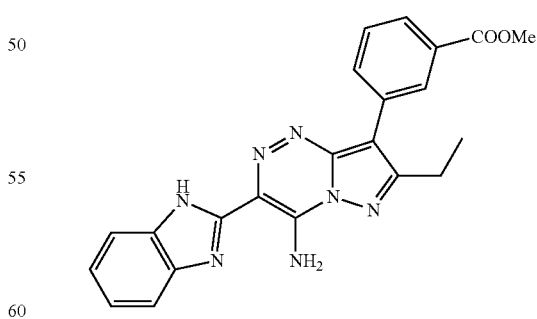

Prepared from compound from Preparative Example 4S.
$^1$H NMR (500 MHz, DMSO-$d_6$): δ 1.39 (t, J=7.5 Hz, 3H), 3.10 (q, J=7.7, Hz, 2H), 3.92 (s, 3H), 7.36-7.17 (m, 2H), 7.56 (d, J=7.7 Hz, 1H), 7.72-7.66 (m, 1H) 7.76 (d, J=7.7 Hz, 1H), 7.98-7.95 (m, 1H), 8.14-8.05 (m, 1H) 8.59 (s, 1H), 9.42 (s, 1H) 9.98 (s, 1H), 13.43 (s, 1H) ppm.

$^{13}$C NMR (126 MHz, DMSO-d$_6$): δ 13.0, 21.1, 52.2, 106.7, 111.4, 118.3, 119.6, 121.8, 122.9, 127.1, 129.1, 129.5, 130.0, 132.0, 133.0, 133.7, 138.7, 142.7, 146.4, 150.0, 158.1, 166.2 ppm.

Preparative Example 5Za

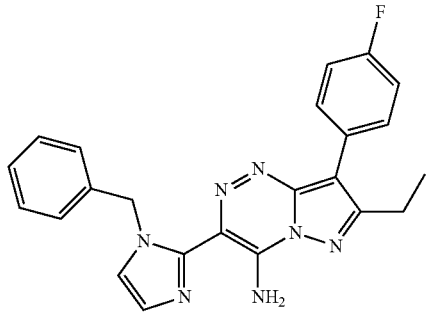 [SMILES: CCc1nn2c(N)c(-c3nccn3Cc3ccccc3)nnc2c1-c1ccc(F)cc1]

Prepared from compounds from Preparative Example 4A and Preparative Example N.

$^1$H NMR (500 MHz, DMSO-d$_6$): δ 1.32 (t, J=7.5 Hz, 3H), 3.02 (q, J=7.5 Hz, 2H), 5.97 (s, 2H), 7.20 (t, J=6.5 Hz, 3H), 7.23 (d, J=1.1 Hz, 1H), 7.28 (t, J=7.3 Hz, 2H), 7.36-7.30 (m, 2H), 7.48 (d, J=1.1 Hz, 1H), 7.89-7.75 (m, 2H), 9.02 (s, 1H), 10.10 (s, 1H) ppm.

$^{13}$C NMR (126 MHz, DMSO-d$_6$): δ 13.1, 20.8, 51.2, 106.1, 115.4 (d, J=21.4 Hz), 121.4, 126.8, 126.9, 123.4, 127.2, 127.8 (d, J=3.2 Hz), 128.4, 130.7 (d, J=8.1 Hz), 138.1 (d, J=21.7 Hz), 141.7, 145.6, 157.6, 159.9, 161.8 ppm.

$^{19}$F NMR (471 MHz, DMSO-d$_6$) δ −115.72 (s) ppm.

HRMS calculated for C$_{23}$H$_{21}$FN$_7$ [M+H]$^+$ 414.1837, found 414.1836.

Preparative Example 5Zb

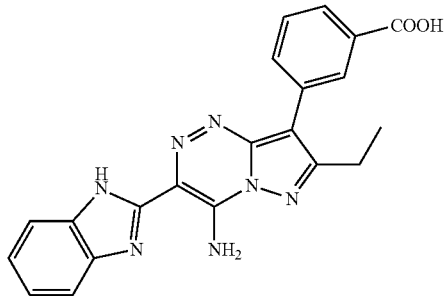 [SMILES: CCc1nn2c(N)c(-c3nc4ccccc4[nH]3)nnc2c1-c1cccc(C(=O)O)c1]

Compound from Preparative Example Z (45 mg, 0.11 mmol) was dissolved in EtOH (3 mL), aqueous solution of 3M NaOH (1.5 mL) was added and the mixture was stirred at 25° C. for 18 hrs. The solvent was removed in vacuo, then aqueous solution of 3M KHSO$_4$ (1.5 mL) was added to the residue. H$_2$O (50 mL) was added and the resulting solution was extracted with EtOAc (3×20 mL). The combined organic extracts were dried over MgSO$_4$, filtered, and solvent was evaporated. The residue was purified by column chromatography on silica gel (EtOAc) to give the product as a yellow solid (7 mg, 16%).

$^1$H NMR (500 MHz, DMSO-d$_6$): δ 1.39 (t, J=7.5 Hz, 3H), 3.11 (q, J=7.6 Hz, 2H), 7.31-7.23 (m, 2H), 7.58-7.54 (m, 1H), 7.67 (t, J=7.7 Hz, 1H), 7.80-7.74 (m, 1H), 7.97-7.93 (m, 1H), 8.13-8.07 (m, 1H), 8.58 (t, J=1.8 Hz, 1H), 9.41 (s, 1H), 9.97 (s, 1H), 12.99 (s, 1H), 13.42 (s, 1H) ppm.

$^{13}$C NMR (126 MHz, DMSO-d$_6$): δ 13.6, 21.6, 107.5, 112.0, 118.8, 120.0, 122.4, 123.5, 127.8, 129.4, 130.2, 137.8, 132.3, 133.2, 134.2, 139.2, 143.2, 147.0, 150.5, 158.6, 167.8 ppm.

HRMS calculated for C$_{21}$H$_{18}$N$_7$O$_2$ [M+H]$^+$ 400.1516, found 400.1514.

Preparative Example 5Zc

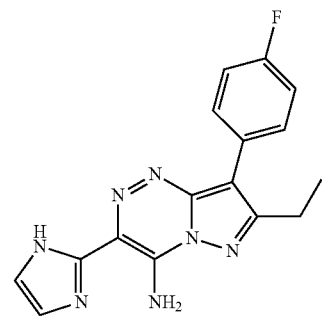 [SMILES: CCc1nn2c(N)c(-c3ncc[nH]3)nnc2c1-c1ccc(F)cc1]

Compound from Preparative Example 5Za (50 mg, 0.12 mmol) was dissolved in degassed EtOH (5 ml), Pd(OH)$_2$ (5 mg) was added and the mixture was refluxed under H$_2$ for 3 hrs. The solvent was evaporated and the residue was purified by column chromatography on silica gel (EtOAc:MeOH/10:1). The product was obtained as a yellow product (22.0 mg, 57%).

$^1$H NMR (500 MHz, DMSO-d$_6$): δ 1.35 (t, J=7.5 Hz, 3H), 3.04 (q, J=7.6 Hz, 2H), 7.19 (s, 1H), 7.30 (s, 1H), 7.38-7.32 (m, 2H), 7.91-7.79 (m, 2H), 9.04 (s, 1H), 9.77 (s, 1H), 13.09 (s, 1H) ppm.

$^{13}$C NMR (126 MHz, DMSO-d$_6$): δ 13.1, 20.8, 106.1, 115.4 (d, J=21.4 Hz), 117.5, 120.3, 127.9 (d, J=29.1 Hz), 130.6 (d, J=7.8 Hz), 137.1, 146.3, 143.9, 157.5, 159.9, 161.8 ppm.

$^{19}$F NMR (471 MHz, DMSO) δ −115.77 (s).

HRMS calculated for C$_{16}$H$_{13}$FN$_7$ [M−H]$^-$ 322.1222, found 322.1226.

Preparative Example 6

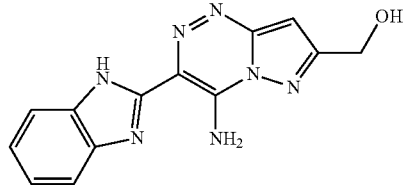 [SMILES: Nc1c(-c2nc3ccccc3[nH]2)nnc2cc(CO)nn12]

1M TBAF in THF (0.5 ml, 0.5 mmol) was added at 0° C. to a solution of compound from Preparative Example 5I (130.0 mg, 0.25 mmol) in THF (5 mL). The mixture was stirred at 25° C. for 2 hrs; then it was poured into water (50 mL). The precipitate was collected by filtration and purified by column chromatography on silica gel (CH$_2$Cl$_2$/: 7N NH$_3$ in MeOH—10:1) to yield the product as an orange solid (52 mg, 57%).

MP>250° C.

$^1$H NMR (500 MHz, DMSO-d$_6$): δ 4.77 (d, 2H, J=5.8 Hz), 5.54 (t, 1H, J=5.8 Hz), 6.94 (s, 1H), 7.20-7.30 (m, 2H), 7.54 (dd, 1H, J=6.9, 1.0 Hz), 7.73 (d, 1H. J=7.2 Hz), 9.42 (s, 1H), 9.93 (s, 1H), 13.43 (s, 1H) ppm.

¹³C NMR (125 MHz, DMSO-d₆): δ 57.7, 94.5, 111.4, 118.2, 118.5, 121.8, 122.8, 133.7, 138.9, 142.6, 149.5, 150.1, 160.8 ppm.

HRMS calculated for $C_{13}H_{12}N_7O$ [M+H]⁺ 282.1098, found 282.1102.

Preparative Example 7

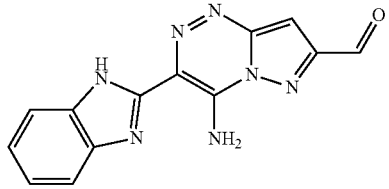 [SMILES: Nc1c(-c2nc3ccccc3[nH]2)nnc2cc(C=O)nn12]

A mixture of compound from Preparative Example 6 (50.0 mg, 0.2 mmol) and IBX (60.0 mg, 0.22 mmol) in wet DMSO (2 mL) was stirred at 50° C. for 16 hrs. The mixture was poured into water (7 mL), the precipitate was collected by filtration and dried in a vacuum to yield the product as a yellow solid (22 mg, 44%).

MP>250° C.

¹H NMR (500 MHz, DMSO-d₆): δ 7.33-7.22 (m, 2H), 7.52 (s, 1H),. 7.56 (d, 1H, J=6.7 Hz), 7.77 (d, 1H. J=6.9 Hz), 9.88 (s, 1H), 10.17 (s, 1H), 10.26 (s, 1H), 13.55 (s, 1H) ppm.

¹³C NMR (125 MHz, DMSO-d₆): δ 6.6, 111.6, 118.4, 119.9, 122.0, 123.1, 133.7, 139.5, 142.6, 149.6, 149.7, 153.2, 187.7 ppm.

HRMS calculated for $C_{13}H_{10}N_7O$ [M+H]⁺ 280.0941, found 280.0945.

Preparative Example 8A

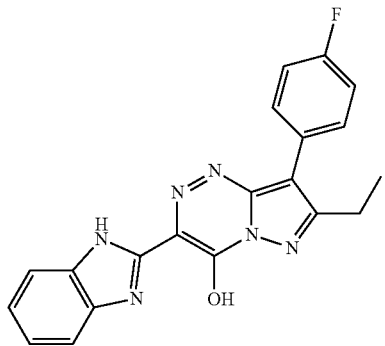 [SMILES: CCc1nn2c(O)c(-c3nc4ccccc4[nH]3)nnc2c1-c1ccc(F)cc1]

Compound from preparative Example 5A (50.0 mg, 0.14 mmol) was dissolved in 23% aqueous HCl (5 mL) and the solution was refluxed for 2 hrs. The reaction mixture was poured into water (20 mL) and neutralized by saturated aqueous solution of NaHCO₃ (150 mL). The precipitate was collected by filtration, washed on filter with water (20 mL), then with Et₂O (15 mL) and dried in a vacuum to yield the product as a yellow solid (35 mg, 70%).

MP>250° C.

¹H NMR (500 MHz, DMSO-d₆): δ 1.27 (t, 3H, J-7.5 Hz), 2.93 (q, 2H. J-7.5 Hz), 7.34 (q, 2H, J=8.9 Hz), 7.46 (m, 2H), 7.78 (m, 4H), 14.12 (s, 2H) ppm.

¹³C NMR (125 MHz, DMSO-d₆): δ 13.0, 20.7, 107.9, 113.4, 115.3 (d, J=21.1 Hz), 119.5, 124.9, 128.0, 130.9 (d, J=8.0 Hz), 131.1, 147.8, 148.8, 155.9, 161.0 (d. J=244.1 Hz) ppm.

HRMS calculated for $C_{20}H_{16}FN_6O$ [M+H]⁺ 375.1364, found 375.1366.

Preparative Example 8B

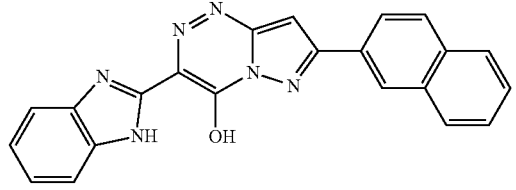 [SMILES: Oc1c(-c2nc3ccccc3[nH]2)nnc2cc(-c3ccc4ccccc4c3)nn12]

By essentially same procedure set forth in Preparative Example 8A, using compound from Preparative Example 5R instead of compound from preparative Example 5A, compound 8B was prepared.

¹H NMR (300 MHz, DMSO-d₆): δ 7.44 (s, 1H), 7.48-7.68 (m, 4H), 7.75-7.91 (m, 2H), 7.92-8.03 (m, 1H), 8.03-8.15 (m, 2H), 8.26 (d, J=8.6 Hz, 1H), 8.69 (s, 1H) ppm.

HRMS calculated for $C_{22}H_{15}N_6O$ [M+H]⁺ 379.1302, found 379.1299.

Preparative Example 9

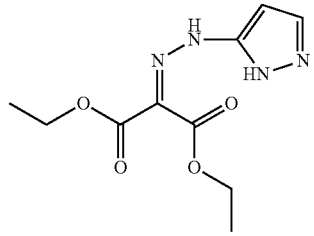 [SMILES: CCOC(=O)C(=NNc1ccn[nH]1)C(=O)OCC]

3-aminopyrazole (0.303 g, 3.65 mmol) was dissolved in H₂O (5 mL) and 35% aqueous HCl (1.29 mL, 14.6 mmol) was added. The solution was cooled to −10° C. and a pre-cooled (−5° C.) solution of NaNO₂ (0.3 g, 4.4 mmol) in H₂O (5 mL) was added. The yellow reaction mixture was stirred for 15 min at 0° C. and then it was added to a solution of KOAc (2.15 g, 21.9 mmol) plus diethylmalonate (0.66 mL, 4.4 mmol) in EtOH (5 mL) and H₂O (5 mL) at −10° C. The resulting mixture changed color to become red and was allowed to warm to 25° C. and then stirred for 6 hrs. Then, EtOAc (30 mL) was added followed by water (20 mL). The organic phase was separated and washed with brine (20 mL). The organic phase was dried over MgSO₄, filtered, and solvent was evaporated. The residue was purified by column chromatography on silica gel (hexane:EtOAc/gradient 2:1; 1:1; 1:2; 0:1) to give the product as a yellow solid (0.565 g, 61%).

MP=227° C. (dec.).

¹H NMR (500 MHz, CDCl₃): δ 135 (t, J=7.1 Hz, 3H), 1.37 (t, J=7.1 Hz, 3H), 4.32 (q, J=7.1 Hz, 2H), 4.35 (q, J=7.2 Hz, 2H), 6.34 (d, J=2.5 Hz, 1H), 7.49 (d, J=2.4 Hz, 1H), 12.78 (s, 1H) ppm.

¹³C NMR (125 MHz, CDCl₃): δ 14.2, 14.3, 61.4, 61.5, 93.8, 120.8, 130.5, 152.8, 163.1, 163.5 ppm.

HRMS calculated for $C_{10}H_{13}N_4O_4$ [M−H]⁻ 253.0942, found 253.0940.

Preparative Example 10

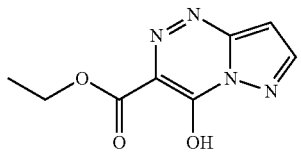

Compound from Preparative Example 9 (0.25 g, 1 mmol) was dissolved in glacial acetic acid (10 mL) and the mixture was refluxed under $N_2$ for 3 hrs. The solvent was evaporated. To the residue was added $CH_2Cl_2$ (5 mL) and after trituration the precipitate was filtered and rinsed with cold $CH_2Cl_2$ (5 mL). The product was dried in a vacuum to give the product as a yellow solid (190 mg, 91%).

MP>250° C. (dec.).

$^1$H NMR (500 MHz, DMSO-$d_6$): δ 1.31 (t, J=7.1 Hz, 3H), 4.32 (q, J=7.1 Hz, 2H), 6.48 (d, J=2.1 Hz, 1H), 8.10 (d, J=2.1 Hz, 1H) ppm.

$^{13}$C NMR (125 MHz, DMSO-$d_6$): δ 14.1, 61.1, 90.0, 127.1, 142.4, 144.9, 147.1, 161.5 ppm.

HRMS calculated for $C_8H_9N_4O_3$ [M+H]$^+$ 209.0669, found 209.0668.

Preparative Example 11

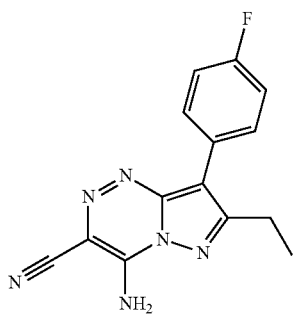 [SMILES: CCc1nn2c(N)c(C#N)nnc2c1-c1ccc(F)cc1]

Compound from Preparative Example 4A (0.36 g, 1.74 mmol) was dissolved in $H_2O$ (3 mL), EtOH (3 mL) and 35% aqueous HCl (0.62 mL, 7 mmol) was added. The solution was cooled to −10° C. and a pre-cooled (−5° C.) solution of NaNO$_2$ (0.24 g, 3.5 mmol) in $H_2O$ (2 mL) and EtOH (2 mL) was added. The yellow reaction mixture was stirred for 20 min at 0° C., then a pre-cooled solution (−10° C.) of KOAc (1.37 g, 14 mmol) plus malononitrile (0.14 g, 2.1 mmol) in EtOH (3 mL) and $H_2O$ (3 mL) was added. The resulting mixture was stirred at 10° C. for 1 hr, then it was allowed to warm to 25° C. and stirred for 10 hrs. EtOAc (50 mL) was added followed by water (20 mL). The organic phase was separated, washed with brine (20 mL), dried over MgSO$_4$, filtered, and the solvent was evaporated. To the residue was added $CH_2Cl_2$ (5 mL) and after trituration the precipitate was filtered and rinsed with cold $CH_2Cl_2$ (5 mL). The solid was dried in a vacuum to give the product as a yellow solid (250 mg, 51%).

MP>215° C. (dec.).

$^1$H NMR (500 MHz, DMSO-$d_6$): δ 1.29 (t, J=7.5 Hz, 3H), 3.00 (q, J=7.6 Hz, 2H), 7.23-7.44 (m, 2H), 7.67-7.87 (m, 2H), 9.27 (s, 2H) ppm.

$^{13}$C NMR (125 MHz, DMSO-$d_6$): δ 12.8, 20.7, 105.3, 109.5, 115.5 (d, J=21.7 Hz), 115.9, 126.8 (d, J=3.6 Hz), 131.1 (d, J=8.1 Hz), 142.5, 145.5, 158.4, 161.3 (d, J=244.4 Hz) ppm.

HRMS calculated for $C_{14}H_{10}FN_6$ [M−H]$^-$ 281.0956, found 281.0956.

Preparative Example 12

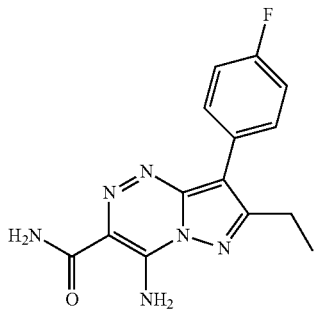 [SMILES: CCc1nn2c(N)c(C(N)=O)nnc2c1-c1ccc(F)cc1]

Compound from Preparative Example 11 (0.075 g, 0.27 mmol) was dissolved in EtOH (1 mL) and NaOH (0.06 g, 1.06 mmol) was added. The mixture was stirred at 85° C. for 24 hrs. The solvent was evaporated and EtOAc (20 mL) was added to the residue followed by water (10 mL). The organic phase was separated, washed with brine (10 mL), dried over MgSO$_4$, filtered, and the solvent was evaporated. The residue was purified by column chromatography on silica gel (hexane:EtOAc/gradient 2:1; 1:1; 1:2; 0:1) to give an orange-yellow solid (0.061 g) containing two compounds (acid and amide) as revealed by NMR. This solid was purified by reverse phase flash chromatography on silica gel C$_{18}$ ($H_2O$:$CH_3CN$:HCOOH/gradient 2:1:0.1; 1:1:0.1; 4:6:0.1; 3:7:0.1; 1:4:0.1; 0:1:0.1) to give the product as an orange solid (0.05 g, 63%).

MP>250° C. (dec.).

$^1$H NMR (500 MHz, DMSO-$d_6$): δ 1.31 (t, J=7.5 Hz, 3H), 3.02 (q, J=7.5 Hz, 2H), 7.31-7.39 (m, 2H), 7.67 (s, 1H), 7.78-7.87 (m, 2H), 8.32 (s, 1H), 8.94 (s, 1H), 9.22 (s, 1H) ppm.

$^{13}$C NMR (125 MHz, DMSO-$d_6$): δ 12.9, 20.8, 107.9, 115.4 (d, J=21.2 Hz), 119.3, 127.4 (d, J=3.3 Hz), 130.8 (d, J=8.2 Hz), 140.5, 146.6, 158.1, 161.1 (d, J=244.0 Hz), 168.3 ppm.

HRMS calculated for $C_{14}H_{14}FN_6O$ [M+H]$^+$ 301.1208, found 301.1209.

Preparative Example 13

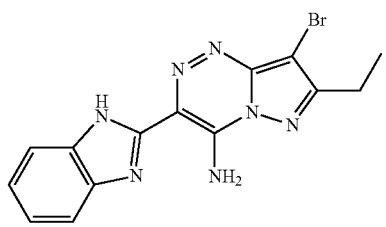 [SMILES: CCc1nn2c(N)c(-c3nc4ccccc4[nH]3)nnc2c1Br]

Compound from Preparative Example 5B (111 mg, 0.40 mmol) was suspended in acetonitrile (8 mL) under nitrogen and the suspension was cooled to 0° C. A solution of NBS (84 mg, 0.47 mmol) in acetonitrile (3 ml) was added dropwise, the mixture was stirred at 25° C. for 4 hrs and then poured into water (50 ml). The precipitate (which appeared in ca. 5 min) was filtered, washed on filter with water (10 mL) and then with Et$_2$O (5 mL). The solid was dried under vacuum to afford the product as an orange solid (102 mg, 73%).

MP>250° C.

$^1$H NMR (500 MHz, DMSO-d$_6$): δ 1.36 (t, 3H. J=7.59 Hz), 2.90 (q, 2H, J=7.60 Hz), 7.22-7.29 (m, 2H), 7.56 (d, 1H, J=7.64 Hz), 7.75 (d, 1H, J=7.66 Hz), 9.54 (s, 1H), 10.09 (s, 1H), 13.40 (s, 1H) ppm.

$^{13}$C NMR (125 MHz, DMSO-d$_6$): δ 12.6, 20.5, 82.5, 111.5, 118.3, 119.7, 121.9, 123.0, 133.7, 138.9, 142.6, 146.0, 149.7, 158.5 ppm.

HRMS calculated for C$_{14}$H$_{11}$BrN$_7$ [M−H]$^-$ 356.0265, found 356.0269.

Preparative Example 14

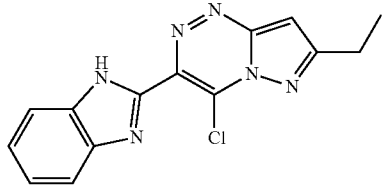 [SMILES: CCc1cc2nnc(-c3nc4ccccc4[nH]3)c(Cl)n2n1]

LiCl (90 mg, 2.12 mmol) and compound from Preparative Example 5B (150 mg, 0.53 mmol) were dissolved in DMF (5 mL) at 50° C. The solution was cooled to 0° C., then SOCl$_2$ (94 mg, 0.8 mmol) and isoamylnitrite (94 mg, 0.8 mmol) were added. The mixture was stirred at 25° C. for 5 hrs. Then, it was poured into saturated aqueous solution of NaHCO$_3$ (25 mL) and extracted with EtOAc (3×25 mL). The combined organic extracts were dried over MgSO$_4$ and the solvent was evaporated. The residue was purified by preparative TLC (EtOAc). The product was isolated as a red solid (10 mg, 6%).

$^1$H NMR (500 MHz, DMSO-d$_6$): δ 1.46 (t, 3H, J=7.6), 3.11 (q, 2H, J=7.6 Hz), 7.77 (t, 1H, J=7.6 Hz), 7.77 (t, 1H, J=7.6 Hz), 7.85 (t, 1H, J=7.7 Hz), 7.90 (s, 1H), 8.18 (d, 1H, J=8.1 Hz), 8.60 (d, 1H, J=8.1 Hz) ppm.

$^{13}$C NMR (125 MHz, DMSO-d$_6$): δ 13.8, 22.4, 102.8, 112.9, 120.7, 121.1, 125.6, 129.1, 129.2, 129.4, 136.0, 143.8, 153.6, 163.7 ppm.

Preparative Example 15

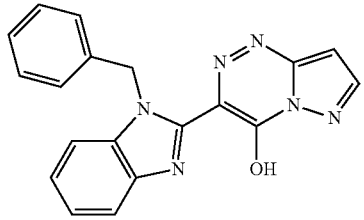 [SMILES: Oc1c(-c2nc3ccccc3n2Cc2ccccc2)nnc2ccnn12]

Compounds from Preparative Example C (0.532 g, 2.55 mmol) and Preparative Example 10 (0.482 g, 2.43 mmol) were suspended in EtOH (2 mL) and AcOH (2 mL). Upon heating, the mixture became homogeneous and then it was refluxed for 4 hours. After cooling to 25° C., a precipitate fromed. EtOH (4 mL) was added and the solid was filtered and washed on filter with EtOH (10 mL). The solid was dried under vacuum to give the product as a pale yellow solid (0.45 g, 54%).

$^1$H NMR (500 MHz, DMSO-d$_6$): δ 5.99 (s, 2H), 6.63 (d, J=2.1 Hz, 1H), 7.19-7.32 (m, 5H), 7.34-7.43 (m, 2H), 7.61 (d, J=7.3 Hz, 1H), 7.81-7.91 (m, 1H), 8.10 (d, J=2.1 Hz, 1H), 14.20 (s, 1H) ppm.

$^{13}$C NMR (126 MHz, DMSO-d$_6$): δ 48.6, 93.6, 111.6, 116.9, 123.9, 124.1, 126.9, 127.5, 128.5, 133.6, 136.4, 144.5, 146.7, 147.9, 149.5 ppm.

HRMS calculated for C$_{19}$H$_{15}$N$_6$O [M+H]$^+$ 343.1302, found 343.1299.

Preparative Example 16

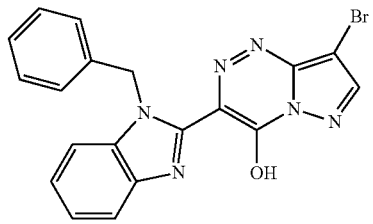 [SMILES: Oc1c(-c2nc3ccccc3n2Cc2ccccc2)nnc2c(Br)cnn12]

Compound from Preparative Example 15 (100 mg, 0.29 mmol) was suspended in DMF (20 mL) and acetonitrile (20 mL) under nitrogen and the suspension was cooled to 0° C. A solution of NBS (55 mg, 0.31 mmol) in DMF (2 ml) was added dropwise. After 10 min at 0° C., the mixture was allowed to warm up to 25° C. After 30 min, a precipitate appeared. The solvent was evaporated and the residue was triturated with cold EtOH (10 mL), collected by filtration, and then on filter washed with EtOH (10 ml) and dried under vacuum. The product was obtained as a yellow solid (114 mg, 93%).

$^1$H NMR (500 MHz, DMSO-d$_6$): δ 6.29 (s, 2H), 7.22-7.35 (m, 5H), 7.49 (p, J=7.3 Hz, 2H), 7.75 (d, J=7.8 Hz, 1H), 7.95 (d, J=7.6 Hz, 1H), 8.21 (s, 1H), 14.18 (s, 1H) ppm.

$^{13}$C NMR (126 MHz, DMSO-d$_6$): δ 49.6, 112,1, 115.0, 125.1, 126.9, 127.6, 128.6, 132.6, 135.8, 144.1, 146.2, 149.1 ppm.

HRMS calculated for C$_{19}$H$_{14}$BrN$_6$O [M+H]$^+$ 421.0407, found 421.0407.

Preparative Example 17A

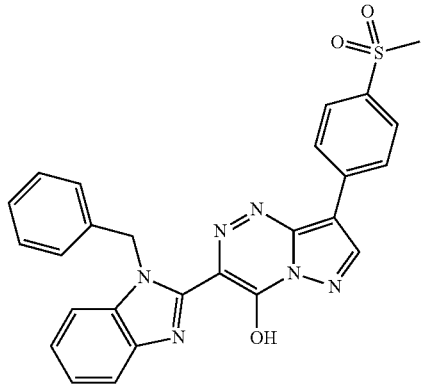 [SMILES: CS(=O)(=O)c1ccc(-c2cnn3c(O)c(-c4nc5ccccc5n4Cc4ccccc4)nnc23)cc1]

Degassed dioxane (4 mL) and H₂O (1 mL) were added to a mixture of compound from Preparative Example 16 (38 mg, 0.09 mmol), 4-methylsulfonephenylboronic acid (22 mg, 0.11 mmol), PdCl₂ (dppf) (3 mg, 0.0045 mmol) and K₃PO₄ (77 mg, 0.36 mmol). The mixture was stirred under N₂ at 120° C. for 4 hours, then it was filtered through a plug of Celite which was then rinsed with MeOH (200 mL). The solvents were evaporated in vacuo and the residue was triturated with EtOH (15 mL) at 60° C. The resulting solid was collected by filtration and washed on filter with EtOH (3×10 mL) to give the product as a yellow solid (44 mg, 98%).

¹H NMR (500 MHz, DMSO-d₆): δ 3.23 (s, 3H), 6.37 (s, 2H), 7.25-7.30 (m, 1H), 7.30-7.39 (m, 4H), 7.45-7.58 (m, 2H), 7.75 (d, J=8.0 Hz, 1H), 7.91-8.04 (m, 3H), 8.51 (d, J=8.3 Hz, 2H), 8.77 (s, 1H), 14.24 (s, 1H) ppm.

¹³C NMR (126 MHz, DMSO-d₆): δ 43.7, 49.6, 112.1, 126.1, 127.0, 127.4, 127.7, 128.7, 135.8, 137.1, 137.5, 142.7, 149.5 ppm.

HRMS calculated for C₂₆H₁₉N₆O₃S [M−H]⁻ 495.1245, found 495.1246.

Preparative Examples 17B-17E

By essentially same procedure set forth in Preparative Example 17A, compounds given below were prepared from the indicated precursors.

Preparative Example 17B

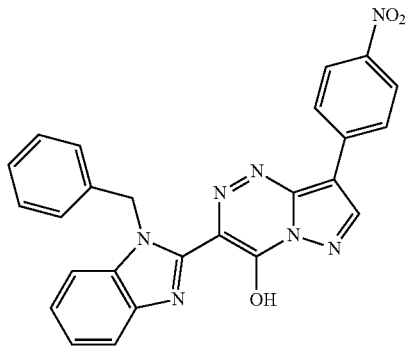 [SMILES: O=[N+]([O-])c1ccc(-c2cnn3c(O)c(-c4nc5ccccc5n4Cc4ccccc4)nnc23)cc1]

Prepared from compound from Preparative Example 16 and 4-nitrophenylboronic acid.

The product was additionally purified by column chromatography on silica gel (EtOAc/MeOH—from 9:1 to 5:1) and then by trituration with dichloromethane/hexane (1:1).

¹H NMR (500 MHz, DMSO-d₆): δ 5.78 (s, 2H), 7.09-7.38 (m, 5H), 7.51 (d, J=7.5 Hz, 1H), 7.79 (s, 1H), 8.27 (d, J=8.4 Hz, 2H), 8.53 (d, J=8.5 Hz, 2H), 8.69 (s, 1H) ppm.

¹³C NMR (126 MHz, DMSO-d₆): δ 111.0, 124.1, 125.3, 126.9, 127.3, 128.4 ppm.

HRMS calculated for C₂₅H₁₈N₇O [M+H]⁺ 464.1466, found 464.1462.

Preparative Example 17C

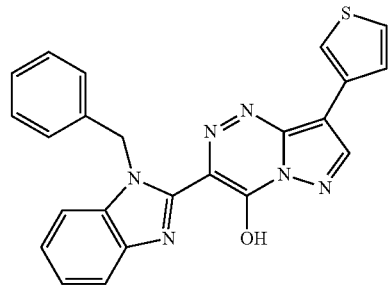 [SMILES: Oc1c(-c2nc3ccccc3n2Cc2ccccc2)nnc2c(-c3ccsc3)cnn12]

Prepared from compound from Preparative Example 16 and thiophene-3-boronic acid.

The product was additionally purified by column chromatography on silica gel (EtOAc/MeOH—from 9:1) and then by trituration with dichloromethane.

¹H NMR (500 MHz, DMSO-d₆): δ 6.32 (s, 2H), 7.21-7.38 (m, 5H), 7.39-7.55 (m, 2H), 7.59-7.68 (m, 1H), 7.67-7.77 (m, 1H), 7.85 (d, J=4.9 Hz, 1H), 7.95 (d, J=7.7 Hz, 1H), 8.08 (s, 1H), 8.52 (s, 1H) ppm.

¹³C NMR (126 MHz, DMSO-d₆): δ 111.8, 119.4, 124.8, 125.9, 126.2, 126.9, 127.6, 128.6, 142.0 ppm.

HRMS calculated for C₂₃H₁₅N₆OS [M−H]⁻ 423.1034, found 423.1033.

Preparative Example 17D

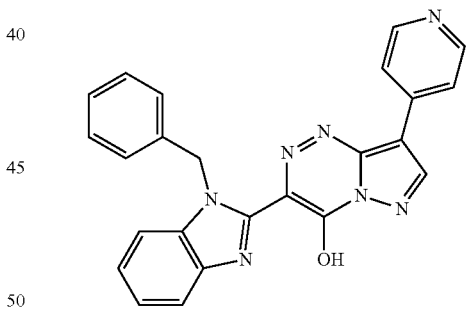

Prepared from compound from Preparative Example 16 and 4-pyridineboronic acid pinacol ester.

The product was additionally purified by column chromatography on silica gel (CH₂Cl₂/MeOH—from 9:1 to 5:1) and then by trituration with dichloromethane.

¹H NMR (500 MHz, DMSO-d₆): δ 6.24 (s, 2H), 7.19-7.41 (m, 5H), 7.41-7.58 (m, 2H), 7.71 (d, J=8.0 Hz, 1H), 7.95 (d, J=7.8 Hz, 1H), 8.38 (d, J=5.2 Hz, 2H), 8.62 (s, 2H), 8.84 (s, 1H) ppm.

¹³C NMR (126 MHz, DMSO-d₆): δ 49.3, 106.0, 112.1, 115.6, 120.2, 124.9, 125.1, 126.9, 127.6, 128.6, 132.8, 135.9, 143.1, 146.5, 146.8, 149.0, 149.2 ppm.

HRMS calculated for C₁₉H₁₅N₆O₃S [M+H]⁺ 405.0775, found 405.0772.

Preparative Example 17E

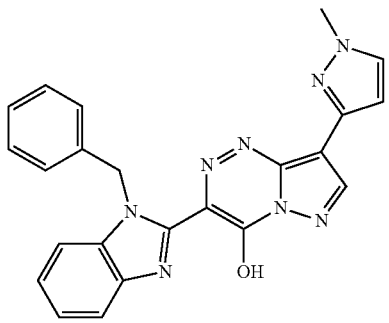 [SMILES: Cn1ccc(-c2cnn3c(O)c(-c4nc5ccccc5n4Cc4ccccc4)nnc23)n1]

Prepared from compound from Preparative Example 16 and 1-methylpyrazole-4-boronic acid pinacol ester.

The product was additionally purified by column chromatography on silica gel (CH$_2$Cl$_2$/MeOH—97:3).

$^1$H NMR (500 MHz, DMSO-d$_6$): δ 3.89 (s, 3H), 6.42 (s, 2H), 7.24-7.29 (m, 1H), 7.29-7.38 (m, 4H), 7.41-7.54 (m, 2H), 7.65-7.78 (m, 1H), 7.97 (d, J=14.9 Hz, 2H), 8.26 (s, 1H), 8.38 (s, 1H), 14.06 (s, 1H) ppm.

$^{13}$C NMR (126 MHz, DMSO-d$_6$): δ 38.5, 112.5, 127.4, 128.2, 128.3, 129.2, 136.8, 147.1.

HRMS calcd for C$_{23}$H$_{19}$N$_8$O [M+H]$^+$ 423.1676, found 423.1677 ppm.

Preparative Example 18A

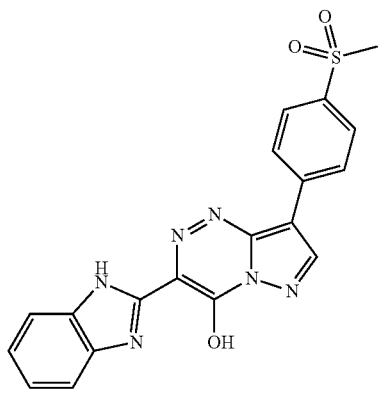 [SMILES: CS(=O)(=O)c1ccc(-c2cnn3c(O)c(-c4nc5ccccc5[nH]4)nnc23)cc1]

Compound from Preparative Example 17A (25 mg, 0.05 mmol) was suspended in degassed MeOH (10 mL), Pd/C (4 mg) was added and the mixture was stirred under H$_2$ at 80° C. for 16 hrs. The mixture was filtered through a plug of Celite, which was rinsed with 50 mL of a 1:1 mixture of CH$_2$Cl$_2$ and MeOH. The filtrate was evaporated. The solid was triturated with EtOH (2×5 mL) and then with CH$_2$Cl$_2$ (2×5 mL). The product was obtained as a yellow solid (10 mg, 50%).

$^1$H NMR (500 MHz, DMSO-d$_6$): δ 3.24 (s, 3H), 7.47 (dd, J=6.1, 3.2 Hz, 2H), 7.78 (dd, J=6.1, 3.2 Hz, 2H), 7.99 (d, J=8.6 Hz, 2H), 8.56 (d, J=8.6 Hz, 2H), 8.76 (s, 1H), 14.21 (s, 1H) ppm.

$^{13}$C NMR (126 MHz, DMSO-d$_6$): δ 43.7, 108.5, 113.6, 120.9, 124.8, 126.1, 127.5, 131.5, 137.3, 137.5, 142.5, 148.0, 148.9 ppm.

Preparative Example 18B

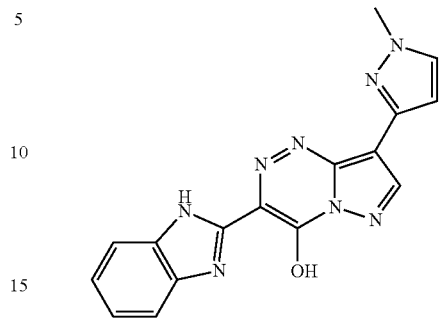

By essentially same procedure set forth in Preparative Example 18A, using the compound from Preparative Example 17 E instead of compound from Preparative Example 17A, compound 18B was prepared.

$^1$H NMR (500 MHz, DMSO-d$_6$): δ 3.92 (s, 3H), 7.45 (d, J=5.8 Hz, 2H), 7.63-7.90 (m, 2H), 8.06 (s, 1H), 8.23 (s, 1H), 8.35 (s, 1H), 14.08 (s, 1H) ppm.

$^{13}$C NMR (126 MHz, DMSO-d$_6$): δ 38.2, 112.7, 124.1, 127.2, 136.2, 140.8 ppm.

HRMS calcd for C$_{16}$H$_{13}$N$_8$O [M+H]$^+$ 333.1207, found 333.1207.

Preparative Example 19

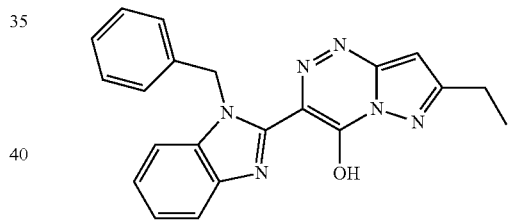

Compound from Preparative Example 4B (260 mg, 2.34 mmol) was dissolved in EtOH (5 mL) and H$_2$O (5 ml) and the mixture was cooled to −10° C. 35% HCl (0.80 ml, 9.36 mmol) was added, then a solution of NaNO$_2$ (36 mg, 4.5 mmol) in EtOH (1 mL) and H$_2$O (1 mL) was added dropwise. The resulting mixture was stirred at −10° C. for 30 min, then it was added to a solution of compound from Preparative Example F (657 mg, 2.34 mmol) in EtOH (5 mL) with KOAc (1.40 g, 14.04 mmol) at 0° C. The resulting mixture was stirred at −10° C. for 16 hrs and then at 25° C. for additional 2 hrs. The solvents were evaporated and DMF (10 mL) was added to the residue. The mixture was stirred at 150° C. for 3 hrs, then it was poured into water (100 mL). The precipitate was collected by filtration and dried under vacuum. The product was obtained as a yellow solid (0.71 g, 82%).

$^1$H NMR (500 MHz, DMSO-d$_6$): δ 1.28 (t, J=7.6 Hz, 3H), 2.74 (q, 6 Hz, 2H), 5.68 (s, 2H), 6.31 (s, 1H), 7.28-7.13 (m, 7H), 7.46 (d, J=7.0 Hz, 1H), 7.74 (d, J=7.4 Hz, 1H), 11.96 (s, 1H) ppm.

$^{13}$C NMR (126 MHz, DMSO-d$_6$): δ 13.5, 21.7, 47.7, 90.6, 110.9, 118.3, 122.2, 122.6, 125.4, 126.9, 127.3, 128.4, 134.4, 137.0, 149.1, 150.6, 158.4, 171.9 ppm.

HRMS calculated for $C_{21}H_{17}N_6O$ [M−H]⁻ 369.1555, found 369.1551.

Preparative Example 20

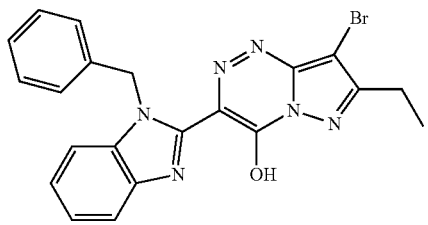 [SMILES: CCc1nn2c(O)c(-c3nc4ccccc4n3Cc3ccccc3)nnc2c1Br]

Compound from Preparative Example 19 (392 mg, 1.06 mmol) was suspended in DMF (10 mL) and the mixture was cooled to 0° C. A solution of NBS (200 mg, 1.11 mmol) in DMF (5 mL) was added dropwise and the mixture was stirred at 25° C. for 18 hrs. The resulting mixture was poured into water (50 mL) and extracted with EtOAc (3×30 mL). The organic phase was washed with brine (40 mL) and the solvent was evaporated. The residue was purified by column chromatography on silica gel (EtOAc). The product was isolated as a yellow solid (314 mg, 66%).

¹H NMR (500 MHz, DMSO-d₆): δ 1.28 (t, J=7.6 Hz, 3H), 2.75 (q, 2H), 5.90 (s, 2H), 7.41-7.15 (m, 7H), 7.57 (d, J=7.2 Hz, 1H), 7.83 (d, J=7.0 Hz, 1H), 14.18 (s, 1H) ppm.

HRMS calculated for $C_{21}H_{18}BrN_6O$ [M+H]⁺ 449.0846, found 449.0843.

Preparative Example 21

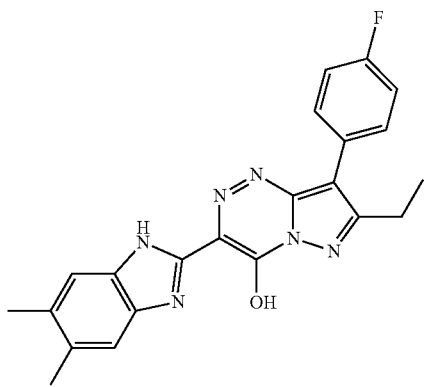 [SMILES: CCc1nn2c(O)c(-c3nc4cc(C)c(C)cc4[nH]3)nnc2c1-c1ccc(F)cc1]

By essentially same procedure set forth in Preparative Example 19, using the compounds from Preparative Example 4A and Preparative Example J, compound 21 was prepared.

¹H NMR (500 MHz, DMSO-d₆): δ 1.28 (t, J=7.5 Hz, 3H), 2.36 (s, 6H), 2.94 (q, J=7.5 Hz, 2H), 7.36-7.28 (m, 2H), 7.50 (s, 2H), 7.86-7.78 (m, 2H), 13.82 (s, 1H) ppm.

¹³C NMR (126 MHz, DMSO-d₆): δ 13.1, 19.9, 20.8, 107.8, 113.3, 115.2 (d, J=21.4 Hz), 119.7, 128.5 (d, J=3.2 Hz), 129.8, 130.7 (d, J=7.8 Hz), 133.5, 147.5, 148.8, 149.3, 155.5, 159.8, 161.7 ppm.

¹⁹F NMR (471 MHz, DMSO-d₆) δ −116.08 (s) ppm.

HRMS calculated for $C_{22}H_{20}FN_6O$ [M+H]⁺ 403.1677, found 403.1671.

Assays:

In vitro assays were used for the determination of compound's $IC_{50}$ values for inhibition of individual nucleases, i.e., MUS81/EME1, FEN1, EXO1, and MRE11. To generate $IC_{50}$ values, concentration of compound was plotted against relative nuclease activity (in %). The dose-response curves were generated from inhibition data, from 5 point serial dilutions of inhibitory compounds, each in triplicate and fitted to a standard sigmoid curve. $IC_{50}$ values were derived by standard nonlinear regression analysis.

All tested compounds were diluted in 100% DMSO (dimethylsulfoxide) to prepare working stocks with different concentrations. To keep the DMSO concentration constant in every reaction, always 0.5 µl of the compound stock was added to the reaction buffer. The reaction buffer differs depending on the enzyme tested. Also concentration of the compounds in the reaction depends on the particular enzyme, since the inhibitory effect of the compounds vary between the enzymes. Nevertheless, always doubling dilutions in the range 200-0.8 µM was used. The compound was added as the first component in the reaction buffer, followed by the enzyme addition. Short (15 minutes) pre-incubation step followed before the reaction was initiated by addition of DNA substrate (5 nM).

As a negative control, DNA substrate specific for each particular enzyme without the addition of the enzyme and the compound was used. The positive control contained all components of the reaction, except the compound of interest. However, to compensate for solvent effects, DMSO (at a final concentration of 2.5%) was included in the reaction.

Nuclease Inhibition Assay

For this experiment we prepared short fluorescently labeled oligonucleotide-based DNA substrates with specific structures reflecting the biochemical activities of tested individual nucleases (Table 1). These substrates were prepared by annealing of synthetic oligonucleotides purchased from VBC Biotech. Composition of each substrate is indicated below the table; the corresponding oligonucleotides were combined in equimolar ratios. For visualization, each substrate was labeled by fluorescent dye (fluorescein), which can be detected in the gel using appropriate imaging system (FLA-9000, Fuji) with filters for particular wavelengths (excitation: 485 nm, emission: 535 nm).

TABLE 1

| Oligo-nucleotide | Sequence |
|---|---|
| Oligo 1 | 5'-AGCTACCATGCCTGCACGAATTAAGCAATTCGTAATCATGGTCATAGCT-3' |
| Oligo 2 | 5'-AGCTATGACCATGATTACGAATTGCTTGGAATCCTGACGAACTGTAG-3' |
| Oligo 3 | 5'-AATTCGTGCAGGCATGGTAGCT-3' |
| Oligo 4 | 5'-AGCTATGACCATGATTACGAATTGCTT-3' |
| Oligo 5 | 5'-GATGTCAAGCAGTCCTAAGGAATTCGTGCAGGCATGGTAGCT-3' |
| Oligo 6 | 5'-AATTCGTGCAGGCATGGTAGCT-3' |

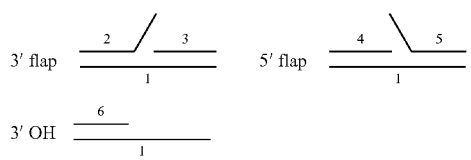

Nuclease assays were performed in reaction buffer specific for particular enzyme: MUS81/EME1 (50 mM Tris pH=7.5, 5 mM MgCl$_2$, 1 mM DTT a 100 μg/ml BSA), MRE11 (30 mM Bis-Tris pH=7.0, 50 μg/ml BSA, 1 mM DTT a 250 μM MnCl$_2$), EXO1 and FEN1 (50 mM Tris pH=7.5, 1 mM MgCl$_2$, 1 mM DTT a 100 μg/ml BSA). The individual reactions were prepared by mixing with highly purified enzyme (MUS81/EME1 (5 nM), MRE11 (5 nM), EXO1 (5 nM) or FEN1 (10 nM); purification protocols described below), and different concentration of inhibitor (mentioned above) in corresponding reaction buffer. The final volume of the reaction was 20 μl. After short pre-incubation (15 minutes at room temperature), the reaction was initiated by addition of 5 nM of corresponding fluorescently labeled DNA substrate (3' flap for MUS81/EME1, 5' flap for MRE11 and FEN1, 3' OH for EXO1; see FIG. 1) and incubated for 15 minutes at 30° C. Next, the reaction was stopped and deproteinized by addition of 2 μl of stop buffer, containing 0.1% SDS and 500 μg/ml proteinase K, and incubated for additional 5 minutes at 30° C. Then the loading dye, containing glycerol (60% glycerol, 10 mM Tris pH=7.4, 60 mM EDTA a 0.1% Orange G), was added to each reaction (1/10 of the reaction volume), and the whole mixture was subjected to electrophoresis in 10% polyacrylamide native gel (110 V, 40 min, 1× TBE). Fluorescently labeled DNA was detected by FLA-9000 scanner (Fuji) and the result was evaluated using Multi-Gauge V3.2 software (Fuji).

Expression and Purification of Mus81/Eme1

The Mus81/Eme1 expression construct was a kind gift from Dr. Steve West (Cancer Research UK). Briefly, the nuclease complex was purified as follows. Lysate was prepared from 40 g of E. coli cell paste using sonication in 50 ml of lysis buffer C (50 mM Tris-HCl, pH 7.5, 10% sucrose, 10 mM EDTA, 1 mM β-mercaptoethanol, 0.01% Nonidet P-40, protease inhibitors) containing 150 mM KCl. The cleared lysate was applied sequentially onto a 20-ml Q-Sepharose and 20-ml SP-Sepharose columns (GE Healthcare). Proteins were eluted from the SP-Sepharose column with a 200-ml gradient from 150 to 1000 mM KCl in buffer K (20 mM K$_2$HPO$_4$, pH 7.5, 10% sucrose, 10 mM EDTA, 1 mM β-mercaptoethanol, 0.01% Nonidet P-40). The peak fractions were pooled and mixed with 1 ml of His-Select nickel affinity gel (Sigma) for 1 h at 4° C. The beads were washed with 10 ml of buffer K containing 150 mM KCl and 10 mM imidazole. The bound proteins were eluted using 50, 150, 300, or 500 mM imidazole in buffer K containing 150 mM KCl. The 150, 300, and 500 mM imidazole fractions were loaded onto a 1-ml Heparin column (GE Healthcare) and proteins were eluted with a 10-ml gradient from 150 to 1000 mM KCl in buffer K. Peak fractions were pooled, loaded onto a 1-ml Mono S column (GE Healthcare), and eluted with a 10-ml gradient from 150 to 1000 mM KCl in buffer K. Pooled fractions were concentrated, flash-frozen in 5 μl aliquots and stored at −80° C.

Expression and Purification of Fen1

The Fen1 expression plasmid was a kind gift from Binghui Shen (City of Hope National Medical Center). Fen1 was expressed and purified according to the method we described elsewhere (J. Biol. Chem. 2009, 284, 7733.).

Briefly, 6 g of E. coli cell paste were break using sonication in 30 ml of buffer C (50 mM Tris-HCl, pH 7.5, 10% sucrose, 10 mM EDTA, 1 mM dithiothreitol, 0.01% Nonidet P-40, protease inhibitors) containing 150 mM KCl. The crude lysate was clarified by centrifugation (100,000×g, 90 min). The cleared lysate was applied sequentially onto a 7-ml Q-Sepharose column and a 7-ml SP-Sepharose column. The SP-Sepharose column was developed with a 70-ml gradient from 100 to 800 mM KCl in buffer K (20 mM K$_2$HPO$_4$, pH 7.5, 10% sucrose, 10 mM EDTA, 1 mM β-mercaptoethanol, 0.01% Nonidet P-40). The peak fractions were pooled and mixed with 0.5 ml of His-Select nickel affinity gel. The beads were washed with 10 column volumes of buffer K containing 150 mM KCl and 5 mM imidazole. The bound proteins were eluted from the affinity beads using 50, 150, 300, and 500 mM imidazole in buffer K containing 150 mM KCl. The 150, 300, and 500 mM imidazole fractions were pooled and further fractionated in a 0.5-ml MonoS column with a 5-ml gradient of 220 to 700 mM KCl in buffer K. Fractions with purified Fen1 were pooled, concentrated in a Vivaspin concentrator, and then stored in 5-μl aliquots at −80° C.

Expression and Purification of Mre11

The MRE11 gene was introduced into the vector pPM271 containing the galactose-inducible hybrid GAL-PGK promoter. The resulting plasmid was introduced into the protease-deficient strain BJ5464 (MATα ura3-52 trp1 leu2Δ1 his3Δ200 pep4::HIS3 prb1Δ1.6R can1). Cultures were grown overnight to the stationary phase in synthetic medium lacking leucine and diluted 8-fold into leucine dropout synthetic media with 3% glycerol, 3% lactic acid, and 2% galactose. After 24 h of growth at 30° C., cells were harvested by centrifugation.

The yeast Mre11 was purified as follows. Approximately 30 g of cell pellet was lysed using cryo-mill and the powder was then resuspended in 120 ml of lysis buffer C containing 100 mM KCl followed by sonication. The lysate was clarified by centrifugation and subjected to ammonium sulfate precipitation at 0.28 g/ml. The resulting precipitate was dissolved in 50 ml of K buffer (20 mM K$_2$HPO$_4$, pH 7.5, 10% sucrose, 10 mM EDTA) containing 0.01% NP40, 1 mM DTT and protease inhibitors and applied to a 20 ml Q-Sepharose column. The protein was eluted in 200-ml gradient from 100-1000 mM KCl. The fractions containing Mre11 were pooled and loaded on a 1-ml macro-hydroxyapatite column, and eluted with a gradient of 0-400 mM KH$_2$PO$_4$ in K buffer+100 mM KCl. The peak fractions were pooled and applied onto 1-ml MonoS column, which was developed with a 10-ml KCl gradient from 100 to 1000 mM KCl. The fractions with purified Mre11 were pooled and concentrated in Vivaspin micro concentrator to final concentration 10 μg/μl. Small (5 μl) aliquots were stored at 80° C.

Expression and Purification of Exo1

The plasmid for expression of human Exo1 was a kind gift from Pavel Janscak (Institute of Molecular cancer Research, University of Zurich).

The Escherichia coli strain BL21 (RIPL) transformed with plasmid containing EXO1 fusion with Mxe-CBD self-cleaving affinity tag was induced with 0.2 mM IPTG for 16 h at 16° C. The cells were pelleted and stored at −80° C. All steps of purification were carried out at 0-4° C. The cell pellet (40 g) was resuspended in 150 ml of buffer CH (50 mM Tris-HCl, pH 8.0, 500 mM NaCl, 1 mM EDTA, 10% glycerol, 0.1% Triton X-100 and protease inhibitors), sonicated and centrifuged (100 000 g, 60 min). Clarified supernatant was loaded onto 10-ml chitin-column (Chitin-agarose beads, New England Biolabs) pre-equilibrated with CH buffer. The column was subsequently flashed with 30 ml of CH buffer supplemented with 50 mM DTT and let overnight to induce protein cleavage. The cleaved hExo1 was eluted with 50 ml of buffer CH in 5 ml fractions. Pooled hExo1 fractions were loaded onto 1.0-ml MonoS column equilibrated with buffer K (20 mM $K_2HPO_4$, pH 7.5, 10% sucrose, 10 mM EDTA, 1 mM β-mercaptoethanol, 0.01% Nonidet P-40) containing 100 mM KCl and eluted with 10 ml gradient of 100-1000 mM KCl in buffer K. Peak fractions were pooled and concentrated in Vivaspin concentrator to final concentration 1 µg/µl. Small aliquots of hExo1 protein was stored at −80° C.

Table 2 shows $IC_{50}$ values (in µM) of different compounds for nucleases tested in our assay.

Results

A: $IC_{50}$<10 µM
B: $IC_{50}$<50 µM
C: $IC_{50}$>50 µM

TABLE 2

| compound from Prep. Example | MUS81/EME1 | MRE11 | FEN1 | EXO1 |
|---|---|---|---|---|
| 5A | A | C | C | C |
| 5B | B | | | |
| 5C | B | C | C | C |
| 5D | B | | | |
| 5F | B | | | |
| 5G | B | | | |
| 5K | A | B | C | C |
| 5M | B | | | |
| 5N | B | | | |
| 5O | C | | | |
| 5P | C | | | |
| 5Y | A | | | |
| 5Z | A | | | |
| 5Zb | A | | | |
| 6 | C | | | |
| 8A | A | | | |
| 11 | C | | | |
| 12 | C | | | |
| 17A | A | | | |
| 17B | A | | | |
| 17C | B | | | |
| 17D | A | | | |
| 17E | B | | | |
| 18A | A | | | |
| 18B | B | | | |
| 21 | A | | | |

The invention claimed is:

1. A compound according to formula (1a):

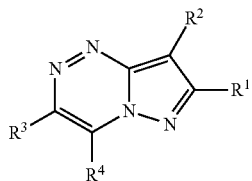

or a pharmaceutically acceptable salt, or solvate thereof, wherein:

R1 is selected from the group consisting of ethyl, propyl, isopropyl, butyl, isobutyl, tert-butyl, phenyl, naphthyl, and biphenyl; wherein each of the ethyl, propyl, isopropyl, butyl, isobutyl, tert-butyl, phenyl, naphthyl, and biphenyl can be unsubstituted or optionally substituted with one or more moieties which can be the same or different, each moiety being independently selected from the group consisting of F, Cl, Br, $C_1$-$C_6$-alkyl, O-phenyl, phenyl (alkyl, O-phenyl, phenyl being optionally substituted by F, Cl, Br, $C_1$-$C_6$-alkyl, OH, O—$C_1$-$C_6$-alkyl, SH, $SCH_3$, $S(O)C_1$-$C_6$-alkyl, $S(O)_2C_1$-$C_6$-alkyl, $CF_3$, $OCF_3$, $NH_2$, $NH(C_1$-$C_6$-alkyl), $N(C_1$-$C_6$-alkyl)$_2$, $NO_2$, COOH, $COO(C_1$-$C_6$-alkyl), $CONH_2$, $CONH(C_1$-$C_6$-alkyl), $CON(C_1$-$C_6$-alkyl)$_2$, $NHC(O)C_1$-$C_6$-alkyl, or $NHC(O)NH_2$), OH, O—$C_1$-$C_6$-alkyl, =O, SH, $SCH_3$, $S(O)C_1$-$C_6$-alkyl, $S(O)_2C_1$-$C_6$-alkyl, $CF_3$, $OCF_3$, $NH_2$, $NH(C_1$-$C_6$-alkyl), $N(C_1$-$C_6$-alkyl)$_2$, $NO_2$, COOH, $COO(C_1$-$C_6$-alkyl), $CONH_2$, $CONH(C_1$-$C_6$-alkyl), $CON(C_1$-$C_6$-alkyl)$_2$, $NHC(O)$ $C_1$-$C_6$-alkyl, $NHC(O)NH_2$, $N_3$, $SO_2NH(C_1$-$C_6$-alkyl), $SO_2N(C_1$-$C_6$-alkyl)$_2$;

R$^2$ is selected from the group consisting of H; alkyl; aryl; cycloalkyl; heterocyclyl; and heteroaryl; wherein each of the alkyl, aryl, cycloalkyl, heterocyclyl, and heteroaryl, can be unsubstituted or optionally substituted with one or more moieties which can be the same or different, each moiety being independently selected from the group consisting of F, Cl, Br, $C_1$-$C_6$-alkyl, O-phenyl, phenyl (alkyl, O-phenyl, phenyl being optionally substituted by F, Cl, Br, $C_1$-$C_6$-alkyl, OH, O—$C_1$-$C_6$-alkyl, SH, $SCH_3$, $S(O)C_1$-$C_6$-alkyl, $S(O)_2C_1$-$C_6$-alkyl, $CF_3$, $OCF_3$, $NH_2$, $NH(C_1$-$C_6$-alkyl), $N(C_1$-$C_6$-alkyl)$_2$, $NO_2$, COOH, $COO(C_1$-$C_6$-alkyl), $CONH_2$, $CONH(C_1$-$C_6$-alkyl), $CON(C_1$-$C_6$-alkyl)$_2$, $NHC(O)C_1$-$C_6$-alkyl, or $NHC(O)NH_2$), OH, O—$C_1$-$C_6$-alkyl, =O, SH, $SCH_3$, $S(O)C_1$-$C_6$-alkyl, $S(O)_2C_1$-$C_6$-alkyl, $CF_3$, $OCF_3$, $NH_2$, $NH(C_1$-$C_6$-alkyl), $N(C_1$-$C_6$-alkyl)$_2$, $NO_2$, COOH, $COO(C_1$-$C_6$-alkyl), $CONH_2$, $CONH(C_1$-$C_6$-alkyl), $CON(C_1$-$C_6$-alkyl)$_2$, $NHC(O)$ $C_1$-$C_6$-alkyl, $NHC(O)NH_2$, $N_3$, $SO_2NH(C_1$-$C_6$-alkyl), $SO_2N(C_1$-$C_6$-alkyl)$_2$;

R$^3$ is selected from the group consisting of benzimidazolyl and imidazolyl, wherein each of benzimidazolyl and imidazolyl can be unsubstituted or optionally substituted with one or more moieties which can be the same or different, each moiety being independently selected from the group consisting of F, Cl, Br, $C_1$-$C_6$-alkyl, O-phenyl, phenyl (alkyl, O-phenyl, phenyl being optionally substituted by F, Cl, Br, $C_1$-$C_6$-alkyl, OH, O—$C_1$-$C_6$-alkyl, SH, $SCH_3$, $S(O)C_1$-$C_6$-alkyl, $S(O)_2C_1$-$C_6$-alkyl, $CF_3$, $OCF_3$, $NH_2$, $NH(C_1$-$C_6$-alkyl), $N(C_1$-$C_6$-alkyl)$_2$, $NO_2$, COOH, $COO(C_1$-$C_6$-alkyl), $CONH_2$, $CONH(C_1$-$C_6$-alkyl), $CON(C_1$-$C_6$-alkyl)$_2$, $NHC(O)C_1$-$C_6$-alkyl, or $NHC(O)NH_2$), OH, O—$C_1$-$C_6$-alkyl, =O, SH, $SCH_3$, $S(O)C_1$-$C_6$-alkyl, $S(O)_2C_1$-$C_6$-alkyl, $CF_3$, $OCF_3$, $NH_2$, $NH(C_1$-$C_6$-alkyl), $N(C_1$-$C_6$-alkyl)$_2$, $NO_2$, COOH, $COO(C_1$-$C_6$-alkyl), $CONH_2$, $CONH(C_1$-$C_6$-alkyl), $CON(C_1$-$C_6$-alkyl)$_2$, $NHC(O)$ $C_1$-$C_6$-alkyl, $NHC(O)NH_2$, $N_3$, $SO_2NH(C_1$-$C_6$-alkyl), $SO_2N(C_1$-$C_6$-alkyl)$_2$;

R$^4$ is selected from the group consisting of OH; and $NH_2$; and when R$^2$ is ethyl, R$^1$ is not a fluorine-substituted phenyl.

2. A compound according to claim 1, wherein $R^1$ is substituted by at least one moiety selected from F, Cl, Br, $C_1$-$C_6$-alkyl, O-phenyl, phenyl, OH, O—$C_1$-$C_6$-alkyl, SH, $SCH_3$, $CF_3$, $OCF_3$, $NH_2$, and $N(CH_3)_2$.

3. A pharmaceutical composition comprising at least one compound according to claim 1 and at least one pharmaceutically acceptable auxiliary compound.

4. A compound according to claim 1, wherein $R^2$ is selected from H, alkyl, aryl, and heteroaryl, optionally substituted by one or more moieties selected from F, Cl, Br, $C_1$-$C_6$-alkyl, OH, O—$C_1$-$C_6$-alkyl, COOH, COO($C_1$-$C_6$-alkyl), $S(O)_2$($C_1$-$C_6$-alkyl), $NO_2$, SH, $SCH_3$, $CF_3$, $OCF_3$, $NH_2$, and $N(CH_3)_2$.

5. A compound according to claim 1, wherein $R^2$ is selected from H, methyl, ethyl, propyl, isopropyl, butyl, isobutyl, tert-butyl, phenyl, naphthyl, and biphenyl, optionally substituted by one or more moieties selected from F, Cl, Br, $C_1$-$C_6$-alkyl, phenyl, OH, O—$C_1$-$C_6$-alkyl, SH, $SCH_3$, $CF_3$, $OCF_3$, $NH_2$, and $N(CH_3)_2$.

\* \* \* \* \*

SEQUENCE LISTING

```
<160> NUMBER OF SEQ ID NOS: 6

<210> SEQ ID NO 1
<211> LENGTH: 49
<212> TYPE: DNA
<213> ORGANISM: Artificial
<220> FEATURE:
<223> OTHER INFORMATION: sequence used in nuclease inhibition assay

<400> SEQUENCE: 1
agctaccatg cctgcacgaa ttaagcaatt cgtaatcatg gtcatagct            49

<210> SEQ ID NO 2
<211> LENGTH: 47
<212> TYPE: DNA
<213> ORGANISM: Artificial
<220> FEATURE:
<223> OTHER INFORMATION: sequence used in nuclease inhibition assay

<400> SEQUENCE: 2
agctatgacc atgattacga attgcttgga atcctgacga actgtag              47

<210> SEQ ID NO 3
<211> LENGTH: 22
<212> TYPE: DNA
<213> ORGANISM: Artificial
<220> FEATURE:
<223> OTHER INFORMATION: sequence used in nuclease inhibition assay

<400> SEQUENCE: 3
aattcgtgca ggcatggtag ct                                         22

<210> SEQ ID NO 4
<211> LENGTH: 27
<212> TYPE: DNA
<213> ORGANISM: Artificial
```

```
<220> FEATURE:
<223> OTHER INFORMATION: sequence used in nuclease inhibition assay

<400> SEQUENCE: 4
agctatgacc atgattacga attgctt                                          27

<210> SEQ ID NO 5
<211> LENGTH: 42
<212> TYPE: DNA
<213> ORGANISM: Artificial
<220> FEATURE:
<223> OTHER INFORMATION: sequence used in nuclease inhibition assay

<400> SEQUENCE: 5
gatgtcaagc agtcctaagg aattcgtgca ggcatggtag ct                         42

<210> SEQ ID NO 6
<211> LENGTH: 22
<212> TYPE: DNA
<213> ORGANISM: Artificial
<220> FEATURE:
<223> OTHER INFORMATION: sequence used in nuclease inhibition assay

<400> SEQUENCE: 6
aattcgtgca ggcatggtag ct                                               22
```